(12) United States Patent
McCluskey et al.

(10) Patent No.: US 11,327,069 B2
(45) Date of Patent: May 10, 2022

(54) BLOOD TESTING SYSTEM AND METHOD

(71) Applicant: C A Casyso GmbH, Basel (CH)

(72) Inventors: Cory Lee McCluskey, Encinitas, CA (US); Robert S. Hillman, San Diego, CA (US); Michael Gorin, Incline Village, NV (US); Hubert Martin Schwaiger, Munich (DE)

(73) Assignee: CA CASYSO GMBH, Basel (CH)

( * ) Notice: Subject to any disclaimer, the term of this patent is extended or adjusted under 35 U.S.C. 154(b) by 0 days.

(21) Appl. No.: 16/201,522

(22) Filed: Nov. 27, 2018

(65) Prior Publication Data

US 2019/0113500 A1     Apr. 18, 2019

Related U.S. Application Data

(62) Division of application No. 14/500,248, filed on Sep. 29, 2014, now Pat. No. 10,175,225.

(51) Int. Cl.
*G01N 33/00* (2006.01)
*G01N 33/49* (2006.01)
(Continued)

(52) U.S. Cl.
CPC .......... *G01N 33/4905* (2013.01); *B01L 3/502* (2013.01); *B01L 3/561* (2013.01);
(Continued)

(58) Field of Classification Search
CPC .... G01N 33/4905; G01N 33/86; G01N 11/00; B01L 3/502; B01L 3/561; B01L 3/567; B01L 2300/087; B01L 2400/049; B01L 2200/0621; B01L 2200/0684; B01L 2200/10; B01L 2400/0694; B01L 2300/0627

See application file for complete search history.

(56) References Cited

U.S. PATENT DOCUMENTS 2,555,937 A  6/1951  Rosenthal
2,995,425 A  8/1961  Hans
(Continued)

FOREIGN PATENT DOCUMENTS

AU  2011237383 B2  10/2012
CN     1816306 A    8/2006
(Continued)

OTHER PUBLICATIONS

Anonymous: "Rotem® delta Whole Block Haemostasis System using Thromboelastometry US Operating Manual," [retrieved on Oct. 30, 2015]. Retrieved from the Internet: <URL:http://www.sfgh-poct.org/wp-content/uploads/2013/02/ROTEM-delta-US-Operating-Manual-Part-12.pdf>, 76 pages, Sep. 2012.
(Continued)

*Primary Examiner* — Samuel P Siefke
(74) *Attorney, Agent, or Firm* — Burns & Levinson LLP

(57) ABSTRACT

Some embodiments of a blood coagulation testing system include an analyzer console device and a single-use cartridge component configured to releasably install into the console device. In some embodiments, the blood coagulation testing system can operate as an automated thromboelastometry system that is particularly useful, for example, at a point-of-care site.

28 Claims, 17 Drawing Sheets

(51) Int. Cl.
*B01L 3/00* (2006.01)
*G01N 11/00* (2006.01)
*G01N 33/86* (2006.01)

(52) U.S. Cl.
CPC .............. *B01L 3/567* (2013.01); *G01N 11/00* (2013.01); *G01N 33/86* (2013.01); *B01L 2200/0621* (2013.01); *B01L 2200/0684* (2013.01); *B01L 2200/10* (2013.01); *B01L 2300/0627* (2013.01); *B01L 2300/087* (2013.01); *B01L 2400/049* (2013.01); *B01L 2400/0694* (2013.01)

(56) References Cited

U.S. PATENT DOCUMENTS

| | | |
|---|---|---|
| 3,714,815 A | 2/1973 | Hartert et al. |
| 3,803,903 A | 4/1974 | Lin |
| 3,903,903 A | 9/1975 | Matsumura |
| 4,112,740 A | 9/1978 | Brandestini |
| 4,148,216 A | 4/1979 | Do et al. |
| 4,193,293 A | 3/1980 | Cavallari |
| D260,428 S | 8/1981 | Fekete |
| 4,319,194 A | 3/1982 | Cardinal |
| 4,558,589 A | 12/1985 | Hemmes et al. |
| 4,599,219 A | 7/1986 | Cooper |
| 4,671,939 A | 6/1987 | Mintz |
| 4,695,956 A | 9/1987 | Leveen et al. |
| 4,705,756 A | 11/1987 | Spillert et al. |
| 4,726,220 A | 2/1988 | Feier et al. |
| 4,752,449 A | 6/1988 | Jackson et al. |
| 4,753,776 A | 6/1988 | Hillman et al. |
| 4,756,884 A | 7/1988 | Hillman et al. |
| 4,765,180 A | 8/1988 | Clifton |
| 4,767,600 A | 8/1988 | Vicario |
| 4,814,247 A | 3/1989 | Spillert et al. |
| D302,294 S | 7/1989 | Hillman et al. |
| 4,849,340 A | 7/1989 | Oberhardt |
| 4,852,577 A | 8/1989 | Smith et al. |
| 4,868,129 A | 9/1989 | Gibbons et al. |
| D305,360 S | 1/1990 | Fechtner |
| 4,900,679 A | 2/1990 | Spillert et al. |
| 4,948,961 A | 8/1990 | Hillman et al. |
| 4,956,089 A | 9/1990 | Hurst |
| 4,963,498 A | 10/1990 | Hillman et al. |
| 5,009,316 A | 4/1991 | Klein |
| 5,016,469 A | 5/1991 | Henderson |
| 5,028,142 A | 7/1991 | Ostoich et al. |
| 5,056,357 A | 10/1991 | Dymling et al. |
| 5,077,017 A | 12/1991 | Gorin et al. |
| 5,091,304 A | 2/1992 | La Duca et al. |
| 5,104,813 A | 4/1992 | Besemer et al. |
| 5,104,975 A | 4/1992 | McCormick et al. |
| D327,743 S | 7/1992 | Frenkel |
| 5,162,237 A | 11/1992 | Messenger et al. |
| 5,164,598 A | 11/1992 | Hillman et al. |
| 5,165,237 A | 11/1992 | Messenger |
| 5,204,525 A | 4/1993 | Hillman et al. |
| 5,205,159 A | 4/1993 | Carr, Jr. |
| 5,207,988 A | 5/1993 | Lucas |
| 5,222,808 A | 6/1993 | Sugarman et al. |
| 5,223,219 A | 6/1993 | Subramanian et al. |
| 5,223,227 A | 6/1993 | Zuckerman |
| 5,234,839 A | 8/1993 | McCormick et al. |
| 5,273,517 A | 12/1993 | Barone et al. |
| 5,287,732 A | 2/1994 | Sekiguchi |
| D347,067 S | 5/1994 | Shartle et al. |
| 5,311,908 A | 5/1994 | Barone et al. |
| 5,331,964 A | 7/1994 | Trahey et al. |
| 5,447,440 A | 9/1995 | Davis et al. |
| 5,473,536 A | 12/1995 | Wimmer |
| 5,487,387 A | 1/1996 | Trahey et al. |
| RE35,171 E | 3/1996 | McCormick et al. |
| 5,504,011 A | 4/1996 | Gavin et al. |
| 5,531,102 A | 7/1996 | Brookfield et al. |
| 5,534,226 A | 7/1996 | Gavin et al. |
| 5,605,154 A | 2/1997 | Ries et al. |
| 5,606,971 A | 3/1997 | Sarvazyan et al. |
| 5,629,209 A | 5/1997 | Braun, Sr. et al. |
| 5,655,535 A | 8/1997 | Friemel et al. |
| 5,657,760 A | 8/1997 | Ying et al. |
| 5,673,699 A | 10/1997 | Trahey et al. |
| 5,744,898 A | 4/1998 | Smith et al. |
| 5,777,212 A | 7/1998 | Sekiguchi et al. |
| 5,777,215 A | 7/1998 | Calatzis et al. |
| 5,788,928 A | 8/1998 | Carey |
| 5,800,781 A | 9/1998 | Gavin et al. |
| 5,810,731 A | 9/1998 | Sarvazyan et al. |
| 5,854,423 A | 12/1998 | Venegas |
| 5,888,826 A | 3/1999 | Ostgaard et al. |
| 5,899,861 A | 5/1999 | Friemel et al. |
| 5,902,937 A | 5/1999 | Amrani et al. |
| 5,921,928 A | 7/1999 | Greenleaf et al. |
| 5,952,560 A | 9/1999 | Collings et al. |
| 6,012,712 A | 1/2000 | Bernstein |
| 6,016,712 A | 1/2000 | Warden et al. |
| 6,039,691 A | 3/2000 | Walker et al. |
| 6,046,051 A | 4/2000 | Jina |
| 6,066,243 A | 5/2000 | Anderson et al. |
| 6,083,159 A | 7/2000 | Driscoll, Jr. et al. |
| 6,114,135 A | 9/2000 | Goldstein |
| 6,117,081 A | 9/2000 | Jago et al. |
| 6,135,957 A | 10/2000 | Cohen-bacrie et al. |
| 6,200,532 B1 | 3/2001 | Wu |
| 6,213,950 B1 | 4/2001 | Cespedes et al. |
| 6,221,672 B1 | 4/2001 | Baugh et al. |
| RE37,171 E | 5/2001 | Busche et al. |
| 6,225,126 B1 | 5/2001 | Cohen et al. |
| 6,232,127 B1 | 5/2001 | Lane et al. |
| 6,264,609 B1 | 7/2001 | Herrington et al. |
| 6,270,459 B1 | 8/2001 | Konofagou et al. |
| 6,277,074 B1 | 8/2001 | Chaturvedi et al. |
| 6,283,917 B1 | 9/2001 | Jago et al. |
| 6,318,191 B1 | 11/2001 | Chen |
| 6,371,912 B1 | 4/2002 | Nightinggale et al. |
| 6,402,704 B1 | 6/2002 | McMorrow |
| 6,412,344 B1 | 7/2002 | Danicich et al. |
| 6,436,722 B1 | 8/2002 | Clark et al. |
| 6,448,024 B1 | 9/2002 | Bruegger |
| 6,451,610 B1 | 9/2002 | Gorman et al. |
| 6,454,714 B1 | 9/2002 | Ng et al. |
| 6,494,834 B2 | 12/2002 | Konofagou et al. |
| 6,508,768 B1 | 1/2003 | Hall et al. |
| 6,514,204 B2 | 2/2003 | Alam et al. |
| 6,535,835 B1 | 3/2003 | Rubin et al. |
| 6,537,819 B2 | 3/2003 | Cohen et al. |
| 6,573,104 B2 | 6/2003 | Carr, Jr. et al. |
| 6,613,286 B2 | 9/2003 | Braun, Sr. et al. |
| 6,613,573 B1 | 9/2003 | Cohen |
| D481,133 S | 10/2003 | Blouin |
| 6,632,678 B2 | 10/2003 | Aiken et al. |
| D482,454 S | 11/2003 | Gebrian |
| 6,662,031 B1 | 12/2003 | Khalil et al. |
| 6,685,646 B2 | 2/2004 | Cespedes et al. |
| 6,687,625 B2 | 2/2004 | Srinivasan et al. |
| 6,692,439 B1 | 2/2004 | Walker et al. |
| 6,699,718 B1 | 3/2004 | Bruegger |
| 6,716,168 B2 | 4/2004 | Nock et al. |
| 6,726,629 B1 | 4/2004 | Frinking et al. |
| 6,750,053 B1 | 6/2004 | Widrig Opalsky |
| 6,764,448 B2 | 7/2004 | Trahey et al. |
| 6,787,363 B2 | 9/2004 | Cohen et al. |
| 6,797,519 B2 | 9/2004 | Cohen et al. |
| 6,838,055 B2 | 1/2005 | Sando et al. |
| 6,890,299 B2 | 5/2005 | Cohen et al. |
| 6,942,836 B2 | 9/2005 | Freudenthal et al. |
| 6,951,127 B1 | 10/2005 | Bi |
| 6,951,544 B2 | 10/2005 | Trahey et al. |
| 6,979,569 B1 | 12/2005 | Carver, Jr. et al. |
| 7,132,078 B2 * | 11/2006 | Rawson ............... G01N 33/558 422/403 |
| 7,179,652 B2 | 2/2007 | Cohen et al. |
| 7,192,726 B1 | 3/2007 | Carr, Jr. et al. |
| 7,202,048 B2 | 4/2007 | Carr, Jr. |

(56) References Cited

U.S. PATENT DOCUMENTS

| | | |
|---|---|---|
| 7,207,939 B2 | 4/2007 | Husher |
| 7,247,488 B2 | 7/2007 | Ghai et al. |
| 7,261,861 B2 | 8/2007 | Kautzky |
| 7,374,538 B2 | 5/2008 | Nightingale et al. |
| 7,399,637 B2 | 7/2008 | Wright et al. |
| 7,412,877 B1 | 8/2008 | Bi |
| 7,422,905 B2 | 9/2008 | Clague et al. |
| 7,439,069 B2 | 10/2008 | Nippoldt et al. |
| 7,491,175 B2 | 2/2009 | Ruether et al. |
| 7,497,997 B2 | 3/2009 | Glezer et al. |
| 7,524,670 B2 | 4/2009 | Cohen et al. |
| 7,595,169 B2 | 9/2009 | Swaim et al. |
| 7,674,616 B2 | 3/2010 | Farnam, III et al. |
| 7,732,213 B2 | 6/2010 | Cohen et al. |
| 7,745,223 B2 | 6/2010 | Schubert et al. |
| 7,811,792 B2 | 10/2010 | Cohen |
| 7,892,188 B2 | 2/2011 | Walker et al. |
| 7,901,629 B2 | 3/2011 | Calatzis et al. |
| 7,912,661 B2 | 3/2011 | Zeng et al. |
| 7,947,505 B2 | 5/2011 | Kawasaki et al. |
| 7,951,606 B2 | 5/2011 | Pei et al. |
| 7,972,271 B2 | 7/2011 | Johnson et al. |
| 8,003,401 B2 | 8/2011 | Tanaami et al. |
| D645,973 S | 9/2011 | Hoenes |
| 8,058,023 B2 | 11/2011 | Gurbel |
| 8,110,392 B2 | 2/2012 | Battrell et al. |
| 8,168,442 B2 | 5/2012 | Petersen et al. |
| 8,372,343 B2 | 2/2013 | Goldstein |
| 8,383,045 B2 | 2/2013 | Schubert et al. |
| 8,448,499 B2 | 5/2013 | Schubert et al. |
| 8,548,759 B2 | 10/2013 | Walker et al. |
| 8,740,818 B2 | 6/2014 | Walker et al. |
| 8,857,244 B2 | 10/2014 | Schubert et al. |
| 9,061,280 B2 | 6/2015 | Tanaami et al. |
| 9,086,423 B2 | 7/2015 | Schubert et al. |
| 9,110,084 B2 | 8/2015 | Schubert et al. |
| D737,993 S | 9/2015 | Tan |
| 9,272,280 B2 | 3/2016 | Viola et al. |
| 9,285,377 B2 | 3/2016 | Schubert |
| 9,410,971 B2 | 8/2016 | Viola et al. |
| D777,343 S | 1/2017 | Gorin et al. |
| 9,739,789 B2 | 8/2017 | Schubert et al. |
| 9,915,671 B2 | 3/2018 | Schubert et al. |
| 9,977,039 B2 | 5/2018 | Viola et al. |
| 10,031,144 B2 | 7/2018 | Viola et al. |
| 10,175,225 B2 | 1/2019 | McCluske et al. |
| 10,481,168 B2 | 11/2019 | Viola et al. |
| 10,746,750 B2 | 8/2020 | Schubert et al. |
| 2002/0013530 A1 | 1/2002 | Cespedes et al. |
| 2002/0040187 A1 | 4/2002 | Alam et al. |
| 2002/0081741 A1 | 6/2002 | Braun, Sr. |
| 2002/0177958 A1 | 11/2002 | Widrig Opalsky et al. |
| 2003/0013958 A1 | 1/2003 | Govari et al. |
| 2003/0073244 A1 | 4/2003 | Cohen et al. |
| 2003/0105398 A1 | 6/2003 | Vitek |
| 2003/0113929 A1 | 6/2003 | Baugh et al. |
| 2003/0170883 A1 | 9/2003 | Martin et al. |
| 2003/0171676 A1 | 9/2003 | Trahey et al. |
| 2003/0199082 A1 | 10/2003 | Miller |
| 2003/0204141 A1 | 10/2003 | Nock et al. |
| 2004/0065143 A1 | 4/2004 | Husher |
| 2004/0068184 A1 | 4/2004 | Trahey et al. |
| 2004/0072278 A1 | 4/2004 | Chou et al. |
| 2004/0072357 A1 | 4/2004 | Stiene et al. |
| 2004/0076546 A1 | 4/2004 | Bissett |
| 2004/0088317 A1 | 5/2004 | Fabrick et al. |
| 2004/0089616 A1 | 5/2004 | Kellogg et al. |
| 2004/0131500 A1 | 7/2004 | Chow |
| 2004/0167403 A1 | 8/2004 | Nightingale et al. |
| 2004/0189311 A1 | 9/2004 | Glezer et al. |
| 2004/0203163 A1 | 10/2004 | Cohen et al. |
| 2004/0214337 A1 | 10/2004 | Kautzky |
| 2005/0004463 A1 | 1/2005 | Chen et al. |
| 2005/0015001 A1 | 1/2005 | Lec et al. |
| 2005/0053305 A1 | 3/2005 | Li et al. |
| 2005/0123447 A1 | 6/2005 | Koike et al. |
| 2005/0136541 A1 | 6/2005 | De Haan |
| 2005/0148899 A1 | 7/2005 | Walker et al. |
| 2005/0164373 A1 | 7/2005 | Oldham et al. |
| 2005/0215901 A1 | 9/2005 | Anderson et al. |
| 2005/0216987 P1 | 9/2005 | Murakami |
| 2005/0220668 A1 | 10/2005 | Coville |
| 2005/0233460 A1 | 10/2005 | Clague et al. |
| 2005/0233466 A1 | 10/2005 | Wright |
| 2007/0038095 A1 | 2/2007 | Greenleaf et al. |
| 2007/0059840 A1 | 3/2007 | Cohen et al. |
| 2007/0078631 A1 | 4/2007 | Ariyoshi et al. |
| 2007/0099290 A1 | 5/2007 | Iido et al. |
| 2007/0105236 A1 | 5/2007 | Chang et al. |
| 2007/0140902 A1 | 6/2007 | Calatzis et al. |
| 2007/0184508 A1 | 8/2007 | Cohen et al. |
| 2007/0243105 A1 | 10/2007 | Kratzer et al. |
| 2007/0259348 A1 | 11/2007 | Phadke et al. |
| 2007/0266778 A1 | 11/2007 | Corey et al. |
| 2007/0276236 A1 | 11/2007 | Jong |
| 2008/0026476 A1 | 1/2008 | Howell |
| 2008/0038828 A1 | 2/2008 | Cohen et al. |
| 2008/0160500 A1 | 7/2008 | Fuller |
| 2008/0194041 A1 | 8/2008 | Guirguis |
| 2008/0194967 A1 | 8/2008 | Sliwa et al. |
| 2008/0200343 A1 | 8/2008 | Clemens |
| 2008/0227217 A1 | 9/2008 | Yamamoto et al. |
| 2008/0249408 A1 | 10/2008 | Palmeri et al. |
| 2008/0251383 A1 | 10/2008 | Sobek |
| 2008/0261261 A1 | 10/2008 | Grimes et al. |
| 2008/0280285 A1 | 11/2008 | Chen et al. |
| 2008/0297169 A1 | 12/2008 | Greenquist et al. |
| 2009/0112483 A1 | 4/2009 | Cohen |
| 2009/0130645 A1 | 5/2009 | Schubert et al. |
| 2009/0181411 A1 | 7/2009 | Battrell et al. |
| 2009/0269837 A1 | 10/2009 | Shevkoplyas et al. |
| 2010/0056383 A1 | 3/2010 | Ririe et al. |
| 2010/0154520 A1 | 6/2010 | Schubert |
| 2010/0184201 A1 | 7/2010 | Schubert et al. |
| 2010/0190193 A1 | 7/2010 | Calatzis et al. |
| 2010/0274130 A1 | 10/2010 | Anand et al. |
| 2010/0294767 A1 | 11/2010 | Catteau et al. |
| 2011/0034805 A1 | 2/2011 | Walker et al. |
| 2011/0151491 A1 | 6/2011 | Dennis et al. |
| 2011/0172661 A1 | 7/2011 | Designer et al. |
| 2011/0201099 A1 | 8/2011 | Anderson et al. |
| 2011/0237913 A1 | 9/2011 | Schubert et al. |
| 2011/0252352 A1 | 10/2011 | Viola et al. |
| 2012/0084022 A1 | 4/2012 | Giovangrandi et al. |
| 2012/0232803 A1 | 9/2012 | Viola et al. |
| 2012/0244392 A1 | 9/2012 | Kleiman |
| 2012/0252127 A1 | 10/2012 | Gregor et al. |
| 2012/0294767 A1 | 11/2012 | Viola |
| 2012/0329082 A1 | 12/2012 | Viola et al. |
| 2013/0137172 A1 | 5/2013 | Ririe et al. |
| 2013/0190584 A1 | 7/2013 | Walker et al. |
| 2013/0270113 A1 | 10/2013 | Huang |
| 2013/0323846 A1 | 12/2013 | Schubert et al. |
| 2013/0323847 A1 | 12/2013 | Schubert et al. |
| 2013/0323848 A1 | 12/2013 | Schubert et al. |
| 2013/0333448 A1 | 12/2013 | Schubert et al. |
| 2014/0004613 A1 | 1/2014 | Goldstein |
| 2014/0271409 A1 | 9/2014 | Knight |
| 2014/0328732 A1 | 11/2014 | Delmenico et al. |
| 2015/0253271 A1 | 9/2015 | Giridhar et al. |
| 2016/0091415 A1 | 3/2016 | Gorin |
| 2016/0091483 A1 | 3/2016 | McCluskey et al. |
| 2016/0091509 A1 | 3/2016 | Di Tullio et al. |
| 2016/0091511 A1 | 3/2016 | Di Tullio et al. |
| 2016/0091514 A1 | 3/2016 | Gorin et al. |
| 2016/0091515 A1 | 3/2016 | Gorin et al. |
| 2016/0091516 A1 | 3/2016 | Gorin |
| 2016/0091517 A1 | 3/2016 | Gorin |
| 2016/0195557 A1 | 7/2016 | Schubert |
| 2016/0313357 A1 | 10/2016 | Viola |
| 2016/0361715 A1 | 12/2016 | Shi et al. |
| 2016/0377638 A1 | 12/2016 | Bels et al. |

(56) References Cited

U.S. PATENT DOCUMENTS

| | | |
|---|---|---|
| 2017/0254318 A1 | 9/2017 | Lee et al. |
| 2018/0133714 A1 | 5/2018 | Wo et al. |
| 2018/0306774 A1 | 10/2018 | Viola et al. |

FOREIGN PATENT DOCUMENTS

| | | |
|---|---|---|
| CN | 1853104 | 10/2006 |
| CN | 1853104 A | 10/2006 |
| CN | 101035479 A | 9/2007 |
| CN | 101195112 | 6/2008 |
| CN | 101195112 A | 6/2008 |
| CN | 101301632 | 11/2008 |
| CN | 101301632 A | 11/2008 |
| CN | 101563562 | 10/2009 |
| CN | 102265151 | 11/2011 |
| CN | 103649751 B | 3/2017 |
| DE | 2740932 | 11/1978 |
| DE | 10135569 | 2/2003 |
| DE | 202014002289 | 9/2014 |
| DE | 202014002289 U1 | 9/2014 |
| EP | 0404456 | 12/1990 |
| EP | 1162457 A2 | 12/2001 |
| EP | 1347058 A2 | 9/2003 |
| EP | 1367392 | 12/2003 |
| EP | 1367392 B1 | 12/2003 |
| EP | 1394546 | 3/2004 |
| EP | 1627725 | 2/2006 |
| EP | 1884778 | 2/2008 |
| EP | 1901065 | 3/2008 |
| EP | 2208996 | 7/2010 |
| EP | 2208996 | 9/2010 |
| EP | 2202517 | 8/2012 |
| EP | 2555704 B1 | 2/2013 |
| EP | 2676143 A2 | 12/2013 |
| EP | 3001196 | 3/2016 |
| EP | 3001196 B1 | 9/2018 |
| GB | 2257256 | 1/1993 |
| JP | 1971-004947 | 11/1971 |
| JP | 1987-140047 | 6/1987 |
| JP | H01140047 A | 6/1987 |
| JP | 1991-031764 | 2/1991 |
| JP | 1997-159596 | 6/1997 |
| JP | 1997-507580 | 7/1997 |
| JP | 2001258868 | 9/2001 |
| JP | 2001-516880 | 10/2001 |
| JP | 2001-516880 A | 10/2001 |
| JP | 2006-053142 | 2/2006 |
| JP | 2007-532878 | 11/2007 |
| JP | 2010-078575 | 4/2010 |
| JP | 2010-266453 | 11/2010 |
| JP | 2010-266453 A | 11/2010 |
| JP | 2011-174952 | 9/2011 |
| JP | 2011-174952 A | 9/2011 |
| JP | 2012-513582 | 6/2012 |
| JP | 2012-513582 A | 6/2012 |
| JP | 2012-515340 | 7/2012 |
| JP | 2013-524176 | 6/2013 |
| JP | 2014-010109 | 1/2014 |
| JP | 2015-045642 | 3/2015 |
| WO | WO 1989/006803 | 7/1989 |
| WO | WO 1999/014595 | 3/1999 |
| WO | WO 2002/50535 | 6/2002 |
| WO | WO 2002/063273 | 8/2002 |
| WO | WO 2005/106467 | 11/2005 |
| WO | WO 2006/091650 | 8/2006 |
| WO | WO 2006/126290 | 11/2006 |
| WO | WO 2007/047961 | 4/2007 |
| WO | WO 2008/075181 | 6/2008 |
| WO | WO 2008/093216 | 8/2008 |
| WO | WO 2009/073851 | 6/2009 |
| WO | 2009152094 A2 | 12/2009 |
| WO | WO 2010/072620 | 7/2010 |
| WO | WO 2010072620 | 7/2010 |
| WO | 2011035162 A1 | 3/2011 |
| WO | WO 2011/117017 | 9/2011 |
| WO | 2011127436 A2 | 10/2011 |
| WO | 2012159021 A2 | 11/2012 |
| WO | 2013105987 A2 | 7/2013 |
| WO | WO 2013/172003 | 11/2013 |
| WO | WO 2014/103744 | 7/2014 |
| WO | WO 2014/115478 | 7/2014 |

OTHER PUBLICATIONS

Calatzis et al., "Strategies to Assess Individual Susceptibility to abciximab Therapy Using a New Functional Assay," *Annals of Hematology*, (Berlin, DE) vol. 76, No. Suppl 1, p. A61, XP009097526, 1998.

Chakroun et al., "The influence of fibrin polymerization and platelet-mediated contractile forces on citrated whole blood thromboelastography profile," *Thromb Haemost.*, 95(5):822-828, May 2006.

Chinese Office Action for Application No. 200980151858.5 dated May 21, 2013, 16 pages.

Chinese Office Action for Application No. 200980151858.5, dated Feb. 14, 2014, 4 pages.

European Extended Search Report for Application No. 13167983.9, dated Nov. 6, 2013, 3 pages.

European Office Action for Application No. 08172769.5, dated Jun. 1, 2011, 12 pages.

European Office Action for Application No. 12179576.9, dated May 22, 2013, 10 pages.

European Office Action for Application No. 13163014.7, dated Mar. 24, 2014, 12 pages.

European Office Action for Application No. 13167979.7, dated Nov. 15, 2016, 8 pages.

European Search Report and Opinion for Application No. 15187347.8, dated Jun. 1, 2016, 16 pages.

Greilich et al., "Near-site monitoring of the antiplatelet drug abciximab using the Hemodyne analyzer and modified thrombelastograph," *J Cardiothorac Vasc Anesth.*, 13(1):58-64, Feb. 1999.

Hartert, "Blood Coagulation Studies with Thromboelastography—A New Research Method," *Klin Wochenschrift*, 26:577-583, Oct. 1948 [English translation].

Healthpact, "Rotational thromboelastometry (ROTEM)—targeted therapy for coagulation management in patients with massive bleeding," Health Policy Advisory Committee on Technology. Retrieved from the Internet: <URL: https://www.health.qld.gov.au/healthpact/docs/briefs/WP024.pdf>, 30 pages, Nov. 2012.

International Preliminary Report on Patentability for PCT/EP2009/067181, dated Jun. 29, 2011, 9 pages.

International Search Report and Written Opinion for Application No. PCT/EP2009/067181, dated Mar. 22, 2010, 12 pages.

International Search Report and Written Opinion for International Application No. PCT/US2016/064790, dated Feb. 15, 2017, 17 pages.

International Search Report and Written Opinion for International Application No. PCT/US2016/064797, dated Feb. 15, 2017, 16 pages.

International Search Report and Written Opinion for International Application No. PCT/US2016/064806, dated Feb. 15, 2017, 18 pages.

International Search Report and Written Opinion for International Application No. PCT/US2016/64800, dated Feb. 16, 2017, 14 pages.

Japanes Office Action in International Application No. JP2015-191180, Dispatch Date: Nov. 17, 2017, (9 pages including English Translation).

Japanese Notification of Refusal for Application No. 2011-541392, dated Jun. 14, 2013, 4 pages.

Japanese Notification of Refusal for Application No. 2014-165975, dated Jul. 17, 2015, 8 pages.

Kawasaki et al., "The effects of vasoactive agents, platelet agonists and anticoagulation on thromboelastography," *Acta Anaesthesiol Scand.*, 51(9):1237-1244, Oct. 2007.

Khurana et al., "Monitoring platelet glycoprotein IIb/IIIa-fibrin interaction with tissue factor-activated thromboelastography," *J Lab Clin Med.*, 130(4):401-411, Oct. 1997.

(56) References Cited

OTHER PUBLICATIONS

Korean Office Action for Application No. 1020117017187, dated Mar. 28, 2016, 11 pages.
Korean Office Action for Application No. 1020167029191, dated Nov. 17, 2016, 5 pages.
Lang et al., "Evaluation of the new device ROTEM platelet" [retrieved on Oct. 28, 2015], Retrieved from the Internet: <URL: https://www.rotem.de/wp-content/uploads/2014/09/Lang-et-al-2014. pdf>, Jan. 1, 2014.
Nield et al., "MRI-based blood oxygen saturation measurements in infants and children with congenital heart disease," *Pediatr Radiol.*, 32(7):518-522. Epub Apr. 16, 2002.
Nielsen et al., "Evaluation of the contribution of platelets to clot strength by thromboelastography in rabbits: the role of tissue factor and cytochalasin D," *Anesth Analg.*, 91(1):35-39, Jul. 2000.
Noon et al., "Reduction of blood trauma in roller pumps for long-term perfusion" World J Surg., 9(1):65-71, Feb. 1985.
Notification of Reasons for Refusal for Application No. 2015-237571, dated Nov. 7, 2016, 5 pages.
Novotny et al., "Platelets secrete a coagulation inhibitor functionally and antigenically similar to the lipoprotein associated coagulation inhibitor," *Blood*, 72(6):2020-2025, Dec. 1988.
Prisco and Paniccia, "Point-of-Care Testing of Hemostasis in Cardiac Surgery", *Thromb J.*, 1(1):1, May 6, 2003.
Rodzynek et al., "The transfer test: a new screening procedure for thrombotic diseases," *J Surg Res.*, 35(3):227-233, Sep. 1983.
Rotem® "When Minutes Count to Stop the Bleeding," Pentapharm GmbH, www.rotem.de, 6 pages, Jun. 2007. [brochure].
ROTEM® delta, "Whole Blood Haemostasis System using Thromboelastomerty Operating Manual," 164 pages, Nov. 17, 2014 [brochure].
ROTEM®, "Targeted therapy for coagulation management in patients with massive bleeding," https://www.health.qld.gov.au/_data/assets/pdf_file/0023/427145/wp024.pdf, Nov. 2012, 30 pages, [brochure].
Rugeri et al., "Diagnosis of early coagulation abnormalities in trauma patients by rotation thromboelastography," *J Thromb Haemost.*, 5(2):289-295, Epub Nov. 16, 2006.
Salooja and Perry, "Thromboelastography," *Blood Coagul Fibrinolysis*, 12(5):327-37, Jul. 2001.
Shore-Lesserson et al., "Thromboelastography-guided transfusion algorithm reduces transfusions in complex cardiac surgery," *Anesth Analg.*, 88(2):312-319, Feb. 1999.
Soria et al., "Fibrin stabilizing factor (F XIII) and collagen polymerization," *Experientia*, 31(11):1355-1357, Nov. 15, 1975.
Spannagl et al., "Point-of-Care Analysis of the Homeostatic System," *Laboratoriumsmedizin*, (Kirchheim, DE), 26(1-2):68-76, Feb. 2002.
Srinivasa et al., "Thromboelastography: Where Is It and Where Is It Heading?" *Int'l Anesthesiology Clinics*, 39(1):35-49, Winter 2001.
Tanaka et al., "Thrombin generation assay and viscoelastic coagulation monitors demonstrate differences in the mode of thrombin inhibition between unfractionated heparin and bivalirudin," *Anesth Analg.*, 105(4):933-939, Oct. 2007.
CN Office Action in Chinese Appln. No. 201680074338.9, dated Feb. 3, 2019, 4 pages (without English translation).
Partial European Search Report in EP Appln. No. 18193752.5, dated Feb. 12, 2019, 15 pages.
Extended European Search Report in EP Appln. No. 18193752.5, dated May 13, 2019, 13 pages.
Extended European Search Report in EP Appln. No. 16871654.6, dated May 27, 2019, 7 pages.
CN Search Report in Chinese Appln. No. 201680074338.9, dated Jan. 25, 2019, 3 pages.
JP Office Action in Japanese Appln. No. 2018-528982 dated Jul. 2, 2019, 14 pages with English translation).
CN Office Action in Chinese Appln. No. 2016800743389 dated Aug. 12, 2019, 13 pages (with English translation).
AU Office Action in Australian Appln. No. 2016364931, dated Mar. 4, 2019, 4 pages.
CN Office Action in Chinese Appln. No. 201680074338.9, dated Feb. 3, 2019, 11 pages (with English translation).
Notification of Reasons for Refusal for JP Appln. No. 2019-001775, dated Jan. 31, 2020, 13 pages, with English translation.
The 510(k) Summary for ROTEM delta, FDA clearance No. K083842 ("the 510 (k) Summary for ROTEM delta"), 14 pages.
The 510(k) Substantial Equivalence Determination Decision Summary for ROTEM delta, FDA clearance No. K083842 (the "Decision Summary for ROTEM delta"), 11 pages.
Alsberg E, Feinstein E, Joy MP, Prentiss M, Ingber DE. Magnetically-guided self-assembly of fibrin matrices with ordered nano-scale structure for tissue engineering. Tissue Eng. Nov. 2006;12(11):3247-56. doi: 10.1089/ten.2006.12.3247. PMID: 17518638.
Berney, Helen & Riordan, J. (2008). Impedance measurement monitors blood coagulation. Analog Dialogue. 42, (3 pages).
Werner Blättler, P.Werner Straub, Andreas Peyer, Effect of in vivo produced fibrinogenfibrin intermediates on viscosity of human blood, Thrombosis Research, vol. 4, Issue 6, 1974, pp. 787-801.
Hemostasis and Thrombosis, Basic Principles and Clinical Practice. 3rd Edition. Eds. Colman R.W., Hirsh J., Marder V.J., Salzman E.W. (J.B. Lippincott Company, Philadelphia). Chapter 1 "Overview of Hemostasis" by R.W. Colman, V.J. Marder, E.W. Salzman, J. Hirsh. pp. 3-18 . 1994.
Crochemore T, Piza FMT, Rodrigues RDR, Guerra JCC, Ferraz LJR, Corrêa TD. A new era of thromboelastometry. Einstein (Sao Paulo). Jul.-Sep. 2017;15(3):380-385. doi: 10.1590/S1679-45082017MD3130. Epub Jun. 12, 2017. PMID: 28614427; PMCID: PMC5823059.
Cuisset T, Frere C, Poyet R, et al. Clopidogrel response: Head-to-head comparison of different platelet assays to identify clopidogrel non-responder patients after coronary stenting. Archives of Cardiovascular Diseases. 2010; 103 (1): 39-45.
Douning et al., "Temperature Corrected Thrombelastography in Hypothermic Patients". Anesthesia & Analgesia, Oct. 1995; 81 (3): 608-611.
Evans, et al., "Rheometry and associated techniques for blood coagulation studies," Medical Engineering and Physics, vol. 30, No. 6, Jul. 2008, pp. 671-679.
Ganter, et al., "Coagulation monitoring: current techniques and clinical use of viscoelastic point-of-care coagulation devices," Anesthesia and Analgesia, vol. 106, No. 5, May 2008, pp. 1366-1375.
Faulds, D. et al., "Abciximab (c7E3 Fab). A review of its pharmacology and therapeutic potential in ischaemic heart disease; Drugs 583-98 (1994)" PubMed P.M.I.D.: 7528131 ("Faulds 1994").
Görlinger, K., et al., "Perioperative Coagulation Management and Control of Platelet Transfusion by Point-of-Care Platelet Function Analysis," Transfus Med Hemother 34: 396-411 (2007).
Neil Harris, et al., ""Coagulation Test A Primer on Hemostasis for Clinical Chemists"," Clinical Laboratory News, Jan. 1, 2012, retrieved from: https://www.aacc.org/cln/articles/2012/january/coagulation-tests, (4 pages).
Harrison P. Assessment of platelet function in the laboratory. Hamostaseologie. Jan. 2009;29(1):25-31. PMID: 19151842, (7 pages).
Janmey PA, Erdile L, Bale MD, Ferry JD. Kinetics of fibrinoligomer formation observed by electron microscopy. Biochemistry. 1983; 22 (18): 4336-40.
Kuntamukkula MS, McIntire LV, Moake JL, Peterson DM, Thompson WJ. Rheological studies of the contractile force within platelet fibrin clots: effects of prostaglandin E1, dibutyryl-CAMP and dibutyryl CGMP. Thrombosis research. 1978; 13 (6): 957-69.
Plotkin, et al., The Journal of Trauma: Injury, Infection, and Critical Care. 2008.
Nielson V, A Comparison of the Thrombelastograph and ROTEM, Blood Coagulation and Fibrinolysis 18: 3, 247-252, 2007.
Hanecke, P and Klouche, M, Thrombelastography Today: Practicability and Analytical Power, Transfusion Medicine and Hemotherapy. 34. 421-428 (2007) ("Hanecke").
Multiplate® Analyzer Product Guide.
VerifyNow® Product Guide.
Thurston GB. Viscoelasticity of Human Blood. Biophysical Journal. 1972; 12: 1205-1217.

(56) References Cited

OTHER PUBLICATIONS

Liptak (CRC Press). Process Measurement and Analysis vol. 1, Chapter 8 Analytical Instrumentation. 8.53 Rheometers, 1628-1636, 2003.
Gottumukkala, Vijaya N., et al., "Assessing Platelet and Fibrinogen Contribution to Clot Strength Using Modified Thromboelastography in Pregnant Women," Anesth Analg, vol. 89, 1999, pp. 1453-1455.
Liu C, Mo YY, Chen ZG, Li X, Li OL, Zhou X. Dual fluorescence/contactless conductivity detection for microfluidic chip. Anal Chim Acta. Jul. 28, 2008;621(2):171-7. doi: 10.1016/j.aca.2008.05.040. Epub May 24, 2008. PMID: 18573381, (7 pages).
Ronalee Lo, Ellis Meng, Integrated and reusable in-plane microfluidic interconnects, Sensors and Actuators B: Chemical, vol. 132, Issue 2, 2008, pp. 531-539, ISSN 0925-4005.
Janus TJ, Lewis SD, Lorand L, Shafer JA. Promotion of thrombin catalyzed activation of factor XIII by fibrinogen. Biochemistry. 1983; 22 (26): 6269-72.
Niewiarowski S, Stewart GJ, Nath N, Sha AT, Lieberman GE. ADP, thrombin, and Bothropsatrox thrombinlike enzyme in platelet dependent fibrin retraction. The American Journal of physiology.1975; 229 (3): 737-45.
Weisel JW. The mechanical properties of fibrin for basic scientists and clinicians. Biophysical Chemistry. 2004; 112 (2-3): 267-276.
Wolberg AS. Plasma and cellular contributions to fibrin network formation , structure and stability. Haemophilia. May 16, 2010: 7-12.
Weiss HJ, Aledort LM, Kochwa S., The effect of salicylates on the hemostatic properties of platelets in man. J Clin Invest. Sep. 1968; 47 (9): 2169-80.
Rahe-Meyer, N. et al., Multicentric comparison of single portion reagents and liquid reagents for thromboelastometry. Blood Coagul Fibrinolysis Apr. 2009; 20 (3): 218-22. PubMed P.M.I.D.: 19657320.
Lang et al., "Multi-centre investigation on reference ranges of ROTEM thromboelastometry," Blood Coagulation and Fibrinolysis, 2005, 16: 301-310.
Lang et al., "Possibilities and limitations of thromboeleastometry/thromboelastography," Downloaded from www.haemostaseologieonline.com on Mar. 6, 2018 / IP: 24.163.60.123.
Lang, T., et al., "Different effects of abciximab and cytochalasin D on clot strength in thrombelastography," Journal of Thrombosis and Haemostasis, 2: 147-153 (2004), PubMed P.M.I.D.: 14717978.
Lang et al., "Evaluation of the new device ROTEM platelet" [retrieved on Dec. 28, 2015]. Retrieved from the Internet: <URL:https://www.rotem.de/wp-content/uploads/2014/09/Lang-et-al-2014.pdf>, Jan. 1, 2014.
Celanese CoolPoly@ E1201 Thermally Conductive Polypropylene; Cool Polymers, Inc., 2014. http://www.matweb.com/search/datasheet_print.aspx?matguid=fb2b886d487d4d15b0abc3d619930ed3, (accessed Feb. 22, 2019).
Stony Brook Portable Field Viscometer (For a quick 'Pass' or 'Fail' decision).
Americas Styrenics Styron® 666D Polystyrene; Dow Chemical, 2008. http://www.matweb.com/search/datasheet_print.aspx?matguid=dfc83225fec64437a9a3e9c7262badbe, (accessed Feb. 22, 2019).
Rugeri et al., "Diagnosis of early coagulation abnormalities in trauma patients by rotation thrombelastography," J Thromb Haemost., 5 (2): 289-295, Epub Nov. 16, 2006.
Viola, Francesco, et al., "A Novel Ultrasound-Based Method to Evaluate Hemostatic Function of Whole Blood," Clin Chim Acta, vol. 411, Nos. 1-2, 2010, pp. 106-113.
Viola, et al., "Sonorheometry: A new Method for Assessing coagulation potential," IEEE Ultrasonics Symposium, vol. 1, 2007, pp. 1001-1004.
Viola, et al., "Sonorheometry: A Noncontact Method for the Dynamic Assessment of Thrombosis," The Annals of Biomedical Engineering, vol. 32, 2004, pp. 696-705.
Tonal, B. Gutiérrez; de la Fuente Tornero, E.; Martinez, I. Garutti; Martinez, M. Villanueva; Huerta, A. Rodríguez Comparison of procoagulatory markers in function of anesthesic/analgesic technique used on the surgery of traumathology prosthesis replacement, European Journal of Anaesthesiology: May 2008—vol. 25—Issue—p. 84.
Van den Berg A., Lammerink T.S.J. (1998) Micro Total Analysis Systems: Microfluidic Aspects, Integration Concept and Applications. In: Manz A., Becker H. (eds) Microsystem Technology in Chemistry and Life Science. Topics in Current Chemistry, vol. 194. Springer, Berlin, Heidelberg, https://doi.org/10.1007/3-540-69544-3_2.
ROTEM® delta, "Targeted therapy stops the bleeding," 6 pages, Jan. 6, 2014, [brochure].
Fundamentals of biomechanics Equiolobrium, Motion, and Deformation. 2nd Edition. Eds. Nihat Özkaya and Margareta Nordin. (Springer Science +Business Media, Inc., New York, NY). Chapter 9 "Mechanical Properties of Biological Tissues." pp. 196-218. 1999.
Fundamentals of biomechanics Equiolobrium, Motion, and Deformation. 3rd Edition. Eds. Nihat Özkaya and Margareta Nordin. (Springer Science +Business Media, Inc., New York, NY). Chapter 15 "Mechanical Properties of Biological Tissues." pp. 221-236. 2012.
Libby G. Puckett et al. Monitoring blood coagulation with magnetoelastic sensors, Biosensors and Bioelectronics, vol. 18, Issues 5-6, 2003, pp. 675-681, ISSN 0956-5663.
Petitioner's Reply to Patent Owner's Response of U.S. Pat. No. 9,272,280 dated Mar. 1, 2018, 17 pages.
Petitioner's Reply to Patent Owner's Response of U.S. Pat. No. 9,410,971 dated Mar. 1, 2018, 25 pages.
Petition for Inter Partes Review of U.S. Pat. No. 9,410,971 B2, dated Nov. 30, 2017, 74 pages.
Petition for Inter Partes Review of U.S. Pat. No. 9,410,971 B2, dated Feb. 3, 2017, 51 Pages.
Petition for Inter Partes Review of U.S. Pat. No. 9,272,280 B2, dated Feb. 27, 2018, 28 pages.
Petition for Inter Partes Review for U.S. Pat. No. 9,915,671 dated Apr. 20, 2018, 76 pages.
Decision Denying Petitioner's Request for Rehearing for Inter Partes Review of U.S. Pat. No. 9,410,971, entered Nov. 3, 2017, 7 pages.
Conduct of Proceeding for Inter Partes Review of U.S. Pat . No. 9,272,280 B2 dated Apr. 26, 2018, 3 pages.
Conduct of Proceeding for Inter Partes Review of U.S. Pat. No. 9,410,971 dated Apr. 26, 2018, 3 pages.
Conduct of Proceeding for Inter Partes Review of U.S. Pat. No. 9,410,971 dated May 24, 2018, 5 pages.
Conduct of Proceeding for Inter Partes Review of U.S. Pat. No. 9,410,971 dated Mar. 9, 2018, 6 pages.
Conduct of Proceeding for Inter Partes Review of U.S. Pat. No. 9,410,971 dated May 5, 2017, 3 pages.
Conduct of Proceeding for Inter Partes Review of U.S. Pat. No. 9,410,971 dated Jul. 7, 2017, 7 pages.
Petitioner's Supplemental Reply for Inter Partes Review of U.S. Pat. No. 9,272,280 B2 dated May 18, 2018, 10 pp.
Patent Owner's Preliminary Response for Inter Partes Review for U.S. Pat. No. 9,272,280 dated Jun. 6, 2017, 34 pages.
Patent Owner's Preliminary Response to Petition Requesting Inter Partes Review of U.S. Pat. No. 9,410,971, dated Feb. 14, 2018, 33 pages.
Patent Owner's Preliminary Response for Inter Partes Review for U.S. Pat. No. 9,410,971 dated Jun. 7, 2017, 60 pages.
Patent Owner's Preliminary Response for Inter Partes Review for U.S. Pat. No. 9,915,671 dated Jul. 20, 2018, 14 pages.
Petition for Post-Grant Review of U.S. Pat. No. 10,031,144, dated Apr. 24, 2019, 104 pages.
Petition for Post-Grant Review of U.S. Pat. No. 9,977,039, dated Feb. 21 , 2019, 95 pages.
Decision to Institute for Inter Partes Review of U.S. Pat. No. 9,915,671, dated Oct. 5, 2018, 27 pages.
Final Written Decision for Inter Partes Review of U.S. Pat. No. 9,272,280, dated Feb. 13, 2019, 25 pages.
Final Written Decision for Inter Partes Review of U.S. Pat. No. 9,410,9710, dated Feb. 13, 2019, 55 pages.
Declaration of Patrick D. Mize, Ph.D., for Inter Partes Review of U.S. Pat. No. 9,272,280 dated Feb. 3, 2017, 83 pages.

(56) References Cited

OTHER PUBLICATIONS

Declaration of Patrick D. Mize, Ph.D., for Inter Partes Review of U.S. Pat. No. 9,410,971 dated Feb. 3, 2017, 124 pages.
Declaration of John Avila for Inter Partes Review of U.S. Pat. No. 9,915,671, dated Jan. 4, 2019, 38 pages.
Declaration of Scott Diamond, Ph.D., for Inter Partes Review of U.S. Pat. No. 9,915,671 dated Apr. 20, 2018, 148 pages.
Declaration of Scott Diamond, Ph.D., for Inter Partes Review of U.S. Pat. No. 9,915,671 dated Apr. 20, 2018, 8 pages.
Declaration of Scott Diamond, Ph.D., for Inter Partes Review of U.S. Pat. No. 9,272,280 dated Dec. 1, 2017, 48 pages.
Declaration of Scott Diamond, Ph.D., for Inter Partes Review of U.S. Pat. No. 9,410,971 dated Dec. 1, 2017, 70 pages.
Reply Declaration of Scott Diamond, Ph.D., for Inter Partes Review of U.S. Pat. No. 9,915,671 dated Apr. 3, 2019, 19 pages.
Declaration of Frank M. Laduca, Ph.D., for Inter Partes Review of U.S. Pat. No. 9,915,671 dated Jan. 4, 2019, 37 pages.
Declaration of Frank M. Laduca, Ph.D., for Inter Partes Review of U.S. Pat. No. 9,977,039 dated Feb. 21, 2019, 117 pages.
Declaration of James P. Landers, for Inter Partes Review of U.S. Pat. No. 9,977,039 dated May. 28, 2019, 51 pages.
Declaration of James P. Landers, for Inter Partes Review of U.S. Pat. No. 10,031,144 dated Jul. 29, 2019, 56 pages.
Deposition of Scott Diamond, Ph.D., for Inter Partes Review of U.S. Pat. No. 9,272,280 dated Jan. 18, 2018, 229 pages.
Deposition of Scott Diamond, Ph.D., for Inter Partes Review of U.S. Pat. No. 9,410,971 dated Jan. 18, 2018, 229 pages.
Deposition of Scott Diamond, Ph.D., for Inter Partes Review of U.S. Pat. No. 9,915,671 dated Apr. 26, 2019, 385 pages.
Deposition of Scott Diamond, Ph.D., for Inter Partes Review of U.S. Pat. No. 9,915,671 dated Nov. 15, 2018, 330 pages.
Deposition of Frank M. Laduca, Ph.D., for Inter Partes Review of U.S. Pat. No. 9,915,671 dated Feb. 13, 2019, 271 pages.
Deposition of John Avila for Inter Partes Review of U.S. Pat. No. 9,915,671, dated Feb. 5, 2019, 75 pages.
Deposition of Patrick D. Mize, Ph.D., for Inter Partes Review of U.S. Pat. No. 9,410,971 dated Oct. 5, 2017, 81 pages.
Patent Owner's Response for Inter Partes Review of U.S. Pat. No. 9,915,671, dated Jan. 4, 2019, 37 pages.
Patent Owner's Sur-Reply for Inter Partes Review of U.S. Pat. No. 9,915,671, dated May. 6, 2019, 34 pages.
Patent Owner's Response to the Decision to Institute Inter Partes Review of U.S. Pat. No. 9,272,280, dated Dec. 1, 2017, 39 pages.
Patent Owner's Response to the Decision to Institute Inter Partes Review of U.S. Pat. No. 9,410,971, entered Dec. 1, 2017, 59 pages.
Patent Owner's Preliminary Response to Petition for Post Grant Review for Inter Partes Review of U.S. Pat. No. 10,031,144, dated Jul. 29, 2019, 51 pages.
Patent Owner's Preliminary Response to Petition for Post Grant Review for Inter Partes Review of U.S. Pat. No. 9,977,039, dated May. 28, 2019, 53 pages.
Order Conduct of Proceeding for Inter Partes Review of U.S. Pat. No. 9,272,280 B2 dated Jul. 10, 2017, 7 pages.
Order Extending One-Year Pendency for Good Cause for Inter Partes Review of U.S. Pat. No. 9,272,280 B2 dated Aug. 28, 2018, 4 pages.
Order Trial Hearing for Inter Partes Review of U.S. Pat. No. 9,272,280 B2 dated Jun. 4, 2018, 6 pages.
Order Supplemental Trial Hearing for Inter Partes Review of U.S. Pat. No. 9,272,280 B2 dated Aug. 6, 2018, 6 pages.
Record of Oral Hearing for Inter Partes Review of U.S. Pat. No. 9,272,280 B2 dated Aug. 14, 2018, 34 pages.
Record of Oral Hearing for Inter Partes Review of U.S. Pat. No. 9,272,280 B2 dated Jun. 12, 2018, 46 pages.
Scheduling Order for Inter Partes Review of U.S. Pat. No. 9,272,280 B2 dated Sep. 1, 2017, 8 pages.
Decision Institution of Inter Partes Review for Inter Partes Review of U.S. Pat. No. 9,272,280 B2 dated Sep. 1, 2017, 13 pages.
Grant of Good Cause Extension for Inter Partes Review of U.S. Pat. No. 9,272,280 B2 dated Aug. 28, 2018, 3 pages.
Motion for Leave to File for Inter Partes Review of U.S. Pat. No. 9,272,280 B2 dated Jun. 26, 2017, 72 pages.
Notice of Filing Date for Inter Partes Review of U.S. Pat. No. 9,272,280 B2 dated Mar. 6, 2017, 5 pages.
Patent Owner's Objection to Petitioner's Motion to Submit Supplemental Information for Inter Partes Review of U.S. Pat. No. 9,272,280 B2, dated May 30, 2018, 10 pages.
Patent Owner's Objection to Petitioner's Demonstrative Exhibits for Inter Partes Review of U.S. Pat. No. 9,272,280 B2, dated Aug. 10, 2018, 4 pages.
Patent Owner's Request for Oral Argument for Inter Partes Review of U.S. Pat. No. 9,272,280 B2, dated Apr. 10, 2018, 3 pages.
Patent Owner's Request for Supplemental Oral Hearing for Inter Partes Review of U.S. Pat. No. 9,272,280 B2, dated Aug. 3, 2018, 3 pages.
Patent Owner's Mandatory Notices for Inter Partes Review of U.S. Pat. No. 9,272,280 B2, dated Feb. 23, 2017, 4 pages.
Patent Owner's Updated Mandatory Notices for Inter Partes Review of U.S. Pat. No. 9,272,280 B2, dated Jun. 5, 2018, 4 pages.
Patent Owner's Updated Mandatory Notices for Inter Partes Review of U.S. Pat. No. 9,272,280 B2, dated Jun. 22, 2017, 4 pages.
Patent Owner's Updated Mandatory Notices for Inter Partes Review of U.S. Pat. No. 9,272,280 B2, dated Jun. 8, 2017, 4 pages.
Patent Owner's Updated Exhibit List for Inter Partes Review of U.S. Pat. No. 9,272,280 B2, dated Jun. 30, 2017, 2 pages.
Patent Owner's Updated Exhibit List for Inter Partes Review of U.S. Pat. No. 9,272,280 B2, dated Dec. 1, 2017, 3 pages.
Petitioner's Motion to Submit Supplemental Information for Inter Partes Review of U.S. Pat. No. 9,272,280 B2, dated May 22, 2018, 11 pages.
Petitioner's Objections to Patent Owner's Demonstratives for Inter Partes Review of U.S. Pat. No. 9,272,280 B2, dated Jun. 8, 2018, 4 pages.
Petitioner's Objections to Patent Owner's Demonstratives for Inter Partes Review of U.S. Pat. No. 9,272,280 B2, dated Aug. 10, 2018, 6 pages.
Petitioner's Supplemental Request for Oral Argument for Inter Partes Review of U.S. Pat. No. 9,272,280 B2, dated Aug. 2, 2018, 3 pages.
Petitioner's Updated Mandatory Notices for Inter Partes Review of U.S. Pat. No. 9,272,280 B2, dated Jun. 8, 2018, 3 pages.
Petitioner's Updated Exhibit List for Inter Partes Review of U.S. Pat. No. 9,272,280 B2, dated Mar. 1, 2018, 4 pages.
Decision Denying Petitioner's Motion to Withdraw Grounds for Inter Partes Review of U.S. Pat. No. 9,410,971, dated Jul. 11, 2018, 9 pages.
Decision Denying Institution of Inter Partes Review for Inter Partes Review of U.S. Pat. No. 9,410,971, dated May 10, 2018, 15 pages.
Decision Granting Patent Owner's Motion to Submit Supplemental Information for Inter Partes Review of U.S. Pat. No. 9,410,971, dated Jul. 11, 2018, 10 pages.
Decision Institution of Inter Partes Review for Inter Partes Review of U.S. Pat. No. 9,410,971 dated Sep. 1, 2017, 27 pages.
Grant of Good Cause Extension for Inter Partes Review of U.S. Pat. No. 9,410,971 dated Aug. 28, 2018, 3 pages.
Notice of Filing Date for Inter Partes Review of U.S. Pat. No. 9,410,971 dated Dec. 12, 2017, 4 pages.
Notice of Refund for Inter Partes Review of U.S. Pat. No. 9,410,971 dated Jun. 4, 2018, 2 pages.
Patent Owner's Objection to Evidence for Inter Partes Review of U.S. Pat. No. 9,410,971, dated Sep. 18, 2017, 3 pages.
Patent Owner's Objection to Petitioner's Demonstratives for Inter Partes Review of U.S. Pat. No. 9,410,971, dated Aug. 10, 2018, 4 pages.
Patent Owner's Objection to Petitioner's Motion to Submit Supplemental Information for Inter Partes Review of U.S. Pat. No. 9,410,971, dated May. 30, 2018, 10 pages.
Patent Owner's Objection to Petitioner's Motion to Withdraw Grounds for Inter Partes Review of U.S. Pat. No. 9,410,971, dated Jun. 8, 2018, 11 pages.
Patent Owner's Request for Oral Argument for Inter Partes Review of U.S. Pat. No. 9,410,971, dated Apr. 10, 2018, 3 pages.

(56) References Cited

OTHER PUBLICATIONS

Patent Owner's Request for Supplemental Oral Hearing for Inter Partes Review of U.S. Pat. No. 9,410,971, dated Aug. 3, 2018, 3 pages.
Patent Owner's Mandatory Notices for Inter Partes Review of U.S. Pat. No. 9,410,971, dated Feb. 23, 2017, 4 pages.
Patent Owner's Updated Mandatory Notices for Inter Partes Review of U.S. Pat. No. 9,410,971, dated Jun. 8, 2017, 3 pages.
Patent Owner's Updated Mandatory Notices for Inter Partes Review of U.S. Pat. No. 9,410,971, dated Jun. 22, 2017, 4 pages.
Patent Owner's Updated Exhibit List for Inter Partes Review of U.S. Pat. No. 9,410,971, dated Jun. 30, 2017, 2 pages.
Patent Owner's Updated Exhibit List for Inter Partes Review of U.S. Pat. No. 9,410,971, dated Dec. 1, 2017, 3 pages.
Petitioner's Request for Oral Argument for Inter Partes Review of U.S. Pat. No. 9,410,971, dated Apr. 23, 2017, 3 pages.
Petitioner's Request for Refund for Inter Partes Review of U.S. Pat. No. 9,410,971, dated May 26, 2018, 3 pages.
Petitioner's Updated Exhibit List for Inter Partes Review of U.S. Pat. No. 9,410,971, dated Mar. 1, 2018, 3 pages.
Petitioner's Motion to Submit Supplemental Information for Inter Partes Review of U.S. Pat. No. 9,410,971, dated May 22, 2018, 11 pages.
Petitioner's Motion to Withdraw Grounds for Inter Partes Review of U.S. Pat. No. 9,410,971, dated Jun. 1, 2018, 6 pages.
Petitioner's Objection to Patent Owner's Demonstratives for Inter Partes Review of U.S. Pat. No. 9,410,971, dated Aug. 10, 2018, 6 pages.
Petitioner's Reply to Patent Owner's Objection to Motion to Withdraw for Inter Partes Review of U.S. Pat. No. 9,410,971, dated Jun. 15, 2018, 8 pages.
Petitioner's Request for Rehearing for Inter Partes Review of U.S. Pat. No. 9,410,971, dated Sep. 15, 2017, 18 pages.
Petitioner's Reply to Patent Owner's Response for Inter Partes Review of U.S. Pat. No. 9,410,971, dated Mar. 1, 2018, 25 pages.
Petitioner's Supplemental Reply in view of Apr. 26, 2018 Institution of Previously Non-Instituted Grounds for Inter Partes Review of U.S. Pat. No. 9,410,971, dated May. 18, 2018, 15 pages.
Order Extending One-Year Pendency for Good Cause for Inter Partes Review of U.S. Pat. No. 9,410,971, dated Aug. 28, 2018, 3 pages.
Response to Notice of Filing for Inter Partes Review for Inter Partes Review of U.S. Pat. No. 9,410,971, dated May 5, 2017, 7 pages.
Scheduling Order for Inter Partes Review of U.S. Pat. No. 9,410,971, dated Sep. 1, 2017, 8 pages.
Scheduling Order for Inter Partes Review of U.S. Pat. No. 9,915,671, dated Oct. 5, 2018, 8 pages.
Jointly Proposed Protective Order for Inter Partes Review of U.S. Pat. No. 9,915,671, dated Jan. 8, 2019, 14 pages.
Joint Request for Change of Oral Argument Location for Inter Partes Review of U.S. Pat. No. 9,915,671, dated Oct. 11, 2018, 2 pages.
Decision Granting Patent Owner's Motion to Seal & Enter Jointly Proposed Protective Order for Inter Partes Review of U.S. Pat. No. 9,915,671, dated May 15, 2019, 6 pages.
Decision Granting Patent Owner's Motion to Submit Supplemental Information for Inter Partes Review of U.S. Pat. No. 9,915,671, dated Jun. 12, 2019, 8 pages.
Notice of Filing Date for Inter Partes Review of U.S. Pat. No. 9,915,671, dated May 8, 2018, 5 pages.
Order Trial Hearing for Inter Partes Review of U.S. Pat. No. 9,915,671, dated Jun. 5, 2019, 6 pages.
Panel Change Order Conduct of the Proceeding for Inter Partes Review of U.S. Pat. No. 9,915,671, dated Jan. 10, 2019, 3 pages.
Patent Owner's Mandatory Notices for Inter Partes Review of U.S. Pat. No. 9,915,671, dated May 10, 2018, 3 pages.
Patent Owner's Updated Mandatory Notices for Inter Partes Review of U.S. Pat. No. 9,915,671, dated Jun. 8, 2018, 3 pages.
Patent Owner's Motion to Seal for Inter Partes Review of U.S. Pat. No. 9,915,671, dated Jan 4, 2019, 14 pages.
Patent Owner's Motion to Submit Supplemental Information for Inter Partes Review of U.S. Pat. No. 9,915,671, dated May 21, 2019, 35 pages.
Patent Owner's Request for Oral Argument for Inter Partes Review of U.S. Pat. No. 9,915,671, dated Jun. 3, 2019, 3 pages.
Petitioner's Request for Oral Argument for Inter Partes Review of U.S. Pat. No. 9,915,671, dated May 29, 2019, 3 pages.
Petitioner'Reply to Patent Owner's Response for Inter Partes Review of U.S. Pat. No. 9,915,671, dated Apr. 4, 2019, 32 pages.
Petitioner's Opposition to Patent Owner's Motion to Submit Supplemental Information for Inter Partes Review of U.S. Pat. No. 9,915,671, dated May 28, 2019, 71 pages.
Notice of Filing Date for Inter Partes Review of U.S. Pat. No. 9,977,039, dated Feb. 27, 2019, 5 pages.
Patent Owner's Mandatory Notices for Inter Partes Review of U.S. Pat. No. 9,977,039, dated Mar. 7, 2019, 4 pages.
Patent Owner's Mandatory Notices for Inter Partes Review of U.S. Pat. No. 10,031,144, dated May 28, 2019, 4 pages.
Notice of Filing Date for Inter Partes Review of U.S. Pat. No. 10,031,144, dated Apr. 29, 2019, 3 pages.
Notice concerning Alternative Dispute Resolution Date for Inter Partes Review of U.S. Pat. No. 10,031,144, dated Apr. 29, 2019, 2 pages.
*Instrumentation Laboratory Co. v. HemoSonics LLP*, for Inter Partes Review of U.S. Pat. No. 9,410,971, (IPR201700855 Conference Call Transcript), (PTAB May 22, 2018), 50 pages.
*Instrumentation Laboratory Co. v. HemoSonics LLP*, for Inter Partes Review of U.S. Pat. No. 9,410,971, (IPR201700855 Conference Call Transcript), (PTAB May 4, 2018), 72 pages.
Notice of Deposition for Patrick D. Mize, Ph.D., for Inter Partes Review of U.S. Pat. No. 9,272,280 dated Sep. 26, 2017, 3 pages.
Curriculum Vitae for Patrick D. Mize, Ph.D., for Inter Partes Review of U.S. Pat. No. 9,272,280 dated Sep. 26, 2017, 4 pages.
Notice of Deposition for Scott Diamond, Ph.D., for Inter Partes Review of U.S. Pat. No. 9,272,280 dated Jan. 9, 2018, 3 pages.
Curriculum Vitae for Scott Diamond, Ph.D., for Inter Partes Review of U.S. Pat. No. 9,272,280 dated Jan. 9, 2018, 15 pages.
Pertinent Materials reviewed & considered by Scott Diamond, Ph.D., for Inter Partes Review of U.S. Pat. No. 9,272,280 dated Jan. 9, 2018, 2 pages.
Pertinent Materials reviewed & considered by Scott Diamond, Ph.D., for Inter Partes Review of U.S. Pat. No. 9,410,971 dated Jan. 18, 2018, 2 pages.
Curriculum Vitae for Scott Diamond, Ph.D., for Inter Partes Review of U.S. Pat. No. 9,410,971 dated Jan. 18, 2018, 15 pages.
Notice of Deposition for Scott Diamond, Ph.D., for Inter Partes Review of U.S. Pat. No. 9,915,671 dated Apr. 15, 2019, 3 pages.
Pertinent Materials reviewed & considered by Scott Diamond, Ph.D., for Inter Partes Review of U.S. Pat. No. 9,915,671 dated Apr. 15, 2019, 2 pages.
Curriculum Vitae for Scott Diamond, Ph.D., for Inter Partes Review of U.S. Pat. No. 9,915,671 dated Apr. 15, 2019, 15 pages.
Notice of Deposition for Frank M. Laduca, Ph.D., for Inter Partes Review of U.S. Pat. No. 9,915,671 dated Jan. 30, 2019, 3 pages.
Curriculum Vitae for Frank M. Laduca, Ph.D., for Inter Partes Review of U.S. Pat. No. 9,915,671 dated Jan. 30, 2019, 4 pages.
Notice of Deposition for John Avila for Inter Partes Review of U.S. Pat. No. 9,915,671, dated Jan. 25, 2019, 3 pages.
Curriculum Vitae for James P. Landers, for Inter Partes Review of U.S. Pat. No. 9,977,039 dated May. 28, 2019, 25 pages.
Pertinent Materials reviewed & considered by James P. Landers, for Inter Partes Review of U.S. Pat. No. 9,977,039 dated May 28, 2019, 2 pages.
Curriculum Vitae for James P. Landers, for Inter Partes Review of U.S. Pat. No. 10,031,144 dated May 28, 2019, 25 pages.
Pertinent Materials reviewed & considered by James P. Landers, for Inter Partes Review of U.S. Pat. No. 10,031,144 dated May 28, 2019, 2 pages.
Exhibit 1009 as filed for Inter Partes Review of U.S. Pat. No. 9,272,280 dated Dec. 1, 2017, 907 pages.
Exhibit 1003 as filed for Inter Partes Review of U.S. Pat. No. 9,410,971 dated Dec. 1, 2017, 123 pages.

(56) References Cited

OTHER PUBLICATIONS

Exhibit 1003 as filed for Inter Partes Review of U.S. Pat. No. 9,977,039 dated May 28, 2019, 699 pages.
User Manual (2007) for TEG 5000 Thrombelastograph Hemostasis System with TEG Analytical Software (TAS) Version 4.2.3 including 8 pshrd. an addendum (2008) for TEG Analytical Software (TAS) Version 4.3 (the "TEG 5000 User Manual"), 278 pages.
Exhibit 1003 as filed for Inter Partes Review of U.S. Pat. No. 10,031,144 dated Oct. 2, 2018, 472 pages.
Exhibit 1002 as filed for Inter Partes Review of U.S. Pat. No. 10,031,144 dated Oct. 2, 2018, 130 pages.
Exhibit 1074 as filed for Inter Partes Review of U.S. Pat. No. 9,915,671 dated May 28, 2019, 1 page.
Exhibit 1020 as filed for Inter Partes Review of U.S. Pat. No. 9,410,972 dated Jul. 26, 2019, 7 pages.
Exhibit 1069 as filed for Inter Partes Review of U.S. Pat. No. 9,915,671 dated May 28, 2019, 1 page.
IPR2018-00950 Papers as filed for Inter Partes Review of U.S. Pat. No. 9,915,671 dated May 28, 2019, 70 pages.
IPR2018-00950 Preliminary Amendment as filed for Inter Partes Review of U.S. Pat. No. 9,915,671 dated May 28, 2019, 34 pages.
Exhibit 1012 as filed for Inter Partes Review of U.S. Pat. No. 9,272,280 dated Jan. 26, 2017, 4 pages.
Provisional Application as filed for Inter Partes Review of U.S. Pat. No. 9,977,039 dated May 28, 2019, 46 pages.
EPO Communication Pursuant to Article 94(3) EPC for European Application No. 12865280.7, 4 pages as filed Oct. 8, 2018 for Inter Partes Review of U.S. Pat. No. 9,915,671.
Response to EPO Communication Pursuant to Article 94(3) EPC for European Application No. 12865280.7, 13 pages as filed Feb. 18, 2019 for Inter Partes Review of U.S. Pat. No. 9,915,671.
Straub, Andreas, et al. "Using reagent-supported thromboelastometry (ROTEMW) to monitor haemostatic changes in congenital head surgery employing deep hypothermic circulatory arrest" European Journal of Cardio-thoracic Surgery 34 (2008) 641-647. Year: 2008).
Non-Final Office Action received in U.S. Appl. No. 17/182,502, dated Apr. 14, 2021, (12 pages).
Examination Report No. 1 issued in Australian Application No. 2021200600, dated Mar. 17, 2021, 5 pages.
Japanese Notice of Rejection dated Jul. 20, 2021, Application No. 2019-215835 (8 pgs.).
International Search Report & Written Opinion for International Application No. PCT/US2018/040120, dated Sep. 20, 2018, 13 pages.
International Search Report & Written Opinion for International Application No. PCT/US2016/034501, dated Aug. 31, 2016, 17 pages.
International Search Report & Written Opinion for International Application No. PCT/US2017/049505, dated Nov. 2, 2017, 17 pages.
Examiner Requisition for Canadian Patent Application No. 3,033,000, dated Apr. 15, 2020, 4 pages.
Office Action in Chinese Application No. 201880056029.8, dated Sep. 15, 2020, 12 pages (with concise explanation of relevance).
Extended European Search Report for European Patent Application No. 17847520.8, dated Feb. 27, 2020, 7 pages.
Official Notice of Rejection for Japanese Patent Application No. 2020-501278, dated Jul. 14, 2020, 8 pages.
Non-Final Office Action for U.S. Appl. No. 14/958,889, dated May 31, 2019, 10 pages.
Final Office Action for U.S. Appl. No. 14/958,889, dated Feb. 1, 2019, 10 pages.
Non-Final Office Action for U.S. Appl. No. 14/958,889, dated Jul. 5, 2018, 10 pages.
Final Office Action for U.S. Appl. No. 14/500,248, dated Mar. 15, 2018, 12 pages.
Non-Final Office Action for U.S. Appl. No. 14/500,248, dated Aug. 23, 2017, 10 pages.
Final Office Action for U.S. Appl. No. 14/958,889, dated Sep. 13, 2019, 18 pages.

Office Action for Chinese Application No. 2016800743389, dated Apr. 23, 2020, 16 pages, (with English translation).
Office Action in Australian Application. No. 2016364931, dated Mar. 4, 2019, 4 pages.
Advisory Action received in co-pending U.S. Appl. No. 15/202,059, dated Sep. 21, 2017.
Amukele, et al., "Comparison of plasma with whole blood prothrombin time and fibrinogen on the same instrument," American Journal of Clinical Pathology, vol. 133, No. 4, Apr. 2010, pp. 550-556.
Anderson, "Multi-Dimensional Velocity Estimation with Ultrasound Using Spatial Quadrature," IEEE Transactions on Ultrasonics Ferroelectrics & Frequency Control, vol. 45, No. 3, 1998, pp. 852-861.
Anderson, "Preventing Deep Vein Thrombosis and Pulmonary Embolism," Center for Outcomes Research, UMass Med Center, 1998, 23 pages.
Azar et al., "Abciximab in Primary Coronary Angioplasty for Acute Myocardial Infarction Improves Short-and Medium-Term Outcomes", J. Am. Coll. Cardiol., Dec. 1998; 32 (7): 1996-2002. PubMed P.M.I.D.: 9857884.
Becker, R., "Cell-based models of coagulation: a paradigm in evolution," Journal of Thrombosis and Thrombolysis, vol. 20, No. 1, Aug. 2005, pp. 65-68.
Beer: Center for Reproductive Immunology & Genetics, "Thrombophilia: Inherited and Acquired," 6 pages, http://repro-med.net/papers/thromb.php. Mar. 30, 2005.
Bell, et al., "Thrombelastographic evaluation of coagulation in transurethral prostatectomy," British Journal of Urology, vol. 78, No. 5, 1996, pp. 737-741.
Bercoff et al., "In vivo breast tumor detection using transient elastography," Ultrasound in Medicine & Biology, vol. 29, No. 10, 2003, pp. 1387-1396.
Bercoff, et al., "Supersonic Shear Imaging: A New Technique for Soft Tissue Elasticity Mapping," IEEE Transactions on Ultrasonics Ferroelectrics & Frequency Control, vol. 51 , No. 4, 2004, pp. 396-409.
Bilgen, et al., "Error analysis in acoustic elastography. II. Strain estimation and SNR analysis", Journal of the Acoustical Society of America, vol. 101, 1997, pp. 1147-1154.
Bohs, et al., "A Real Time System for Quantifying and Displaying Two-Dimensional Velocities using Ultrasound," Ultrasound in Medicine & Biology, vol. 19, No. 9, Jul. 1993, pp. 751-761.
Bombeli, et al., "Updates in perioperative coagulation: physiology and management of thromboembolism and haemorrhage" British Journal of Anesthesia; vol. 93, No. 2, Aug. 2004, pp. 275-287.
Bonnefous, et al., "Time Domain Formulation of Pulse—Doppler Ultrasound and Blood Velocity Estimation by Cross Correlation," Ultrasonic Imaging 8, 1986, pp. 73-85.
Born, G.V., "Aggregation of Blood Platelets by Adenosine Diphosphate and its Reversal". Nature, Jun. 9, 1962; 194:927-9. PubMed P.M. I.D.: 13871375.
Brock, et al., "Assessing Thrombin Generation at the Point of Care," Clinical Chemistry, vol. 55, No. 3, Mar. 2009, pp. 398-399.
Calléet al., "Evaluation of the Sensitivity of an in vitro High Frequency Ultrasound Device to Monitor the Coagulation Process: Study of the Effects of Heparin Treatment in a Murine Model". Ultrasound Med. Biol., Feb. 2010; 36 (2):295-305. PubMed P.M.I. D.: 20045589.
Carr, M., "In vitro assessment of platelet function," Transfusion of Medicine Reviews, vol. 11, No. 2, Apr. 1997, pp. 106-115.
Carroll, et al., "Measurement of functional fibrinogen levels using the Thrombelastograph" Journal of Clinical Anesthesia, vol. 20, No. 3, May 2008, pp. 186-190.
Carter, G., "Coherence and time delay estimation," Proc IEEE, vol. 75, No. 2, 1987, pp. 236-255.
Chandler, et al., "Development of a rapid emergency hemorrhage panel," Tranfusion, vol. 50, No. 12, Dec. 2010, pp. 2547-2552.
Chandler, et al., "Estimating the rate of thrombin and fibrin generation in vivo during cardiopulmonary bypass," Blood, vol. 101, No. 11, Jun. 2003, pp. 4355-4362.
Chaturvedi, et al., "Testing the limitations of 2-D companding for strain imaging using phantoms," IEEE Transactions on Ultrasonics Ferroelectrics & Frequency Control, vol. 45, 1998, pp. 1022-1031.

(56) References Cited

OTHER PUBLICATIONS

Chavez, J., "A novel thrombelastograph tissue factor / kaolin assay of activated clotting times for monitoring heparin anticoagulation during cardiopulmonary bypass," Anesthesia and Analgesia; vol. 99, No. Nov. 5, 2004, pp. 1290-1294.
Cohn et al., "An elasticity microscope. Part I: Methods," IEEE Transactions on Ultrasonics Ferroelectrics & Frequency Control, vol. 44, 1997, pp. 1304-1319.
Cohn et al., "An elasticity microscope. Part II: Experimental Results," IEEE Transactions on Ultrasonics Ferroelectrics & Frequency Control, vol. 44, 1997, pp. 1320-1331.
Communication pursuant to Article 94(3) EPC dated Apr. 3, 2018 in co-pending application EP 12865280.7.
Communication Pursuant to Article 94(3) EPC issued for European Application No. 12865280.7, dated Mar. 18, 2019, 7 pages.
Communication Pursuant to Article 94(3) EPC, issue for European Application No. 12865280.7, dated Oct. 8, 2018, 17 pages.
Communication pursuant to Rule 114(2) EPC issued in European Patent Application No. 12865280.7, dated Dec. 13, 2016, 5 pages.
Communication pursuant to Rule 94(3) EPC issued in European Patent Application No. 12865280.7, dated Jul. 3, 2017, 3 pages.
Corrected Notice of Allowance issued for U.S. Appl. No. 15/202,059, dated Jun. 22, 2018.
Craft, et al., "A novel modification of the Thrombelastograph assay, isolating platelet function, correlates with optical platelet aggregation," The Journal of Laboratory and Clinical Medicine, vol. 143, No. 5, May 2004, pp. 301-309.
Curry, et al., "Convention and near-patient tests of coagulation," British Journal of Anesthesia, vol. 7, No. 2, Apr. 2007, pp. 45-50.
Dahlback, B., "Blood Coagulation," Lancet, vol. 355, No. 9215, May 2000, pp. 1627-1632.
Decision Denying Patent Owner's Request for Rehearing of Final Decision filed on Dec. 5, 2019. Exhibit 1014 to IPR2018-00950.
Declaration of Keith B. Neeves, Ph.D. filed on Dec. 14, 2020. Exhibit 1002 to IPR2021-00293.
Declaration of U.S. Pat. No. 9,272,280, 67 pages.
Declaration of U.S. Pat. No. 9,410,971, 124 pages.
Definition of "Cavity". Merriam-Webster's Collegiate Dictionary. 2020. Exhibit 1018 to IPR2021-00293*.
Delhaye et al., Temperature corrected thromboelastometry in hypothermic trauma patients: 6AP24. European Journal of Anaesthesiology, May / Jun. 2008, 25:84.
Deposition of Frank Michael LaDuca, Ph.D. on Feb. 13, 2019. Exhibit 1026 to IPR2021-00293.
Despotis, et al., "Monitoring of hemostasis in cardiac surgical patients: impact of point-of-care testing on blood loss and transfusion outcomes," Clinical Chemistry, vol. 43, No. 9, Sep. 1997, pp. 1684-1696.
Dorn-Beineke et al., "Evaluation of the Automated Coagulation Analyzer Sysmex CA-7000" . Thromb. Res., 2005; 116(2):171-9. PubMed P.M.I.D.: 15907533.
Eikelboom et al., "Monitoring Unfractionated Heparin with the aPTT: Time for a Fresh Look". Thromb. Haemost. Nov. 2006: 96 (5): 547-52. Review. PubMed P.M.I.D.: 17080209.
Embree, et al., "Volumetric Blood Flow via Time-Domain Correlation: Experimental Verification," IEEE Transactions on Ultrasonics Ferroelectrics & Frequency Control, vol. 37, No. 2, May 1990, pp. 176-189.
Emelianov et al., "Ultrasound Elasticity Imaging of Deep Venous Thrombosis," Proc. IEEE Ultrasonics Symp., 2000, pp. 1791-1794.
EP Extended Search Report, dated Oct. 24, 2016, in co-pending International Application No. PCT/US2012/025270.
Euroanaesthesia 2004: Joint Meeting of the European Society of Anaesthesiologists and European Academy of Anaesthesiology Lisbon, Portugal, Jun. 5-8, 2004. (2004). European Journal of Anaesthesiology, 21(S32), 1-221. doi:10.1017/S0265021504000419.
Evans PA, Hawkins K, Lawrence M, Williams RL, Barrow MS, Thirumalai N, Williams PR. Rheometry and associated techniques for blood coagulation studies. Med Eng Phys. Jul. 2008;30(6):671-9. doi: 10.1016/ j.medengphy.2007.08.005. Epub Sep. 27, 2007. PMID: 17900965.
Examination Report issued for Australian Application No. 2017248548, dated Jul. 9, 2018.
Examination Report issued in Australian Application No. 2012364908, dated Jul. 23, 2016, 4 pages.
Examination Report issued in Australian Application No. 2012364908, dated Jun. 27, 2017, 5 pages.
Examination Report issued in European Application No. 12865280.7, dated Apr. 3, 2018, 3 pages.
Examination Report issued in European Application No. 12865280.7, dated Mar. 7, 2017, 3 pages.
Extended European Search Report issued in European Patent Application No. 11766842.6, dated Oct. 21, 2015, 10 pages.
Extended Search Report issued in European Patent Application No. 12865280, dated Oct. 24, 2016, 5 pages.
Fatemi et al., "C-Scan Imaging by Radiation Force Stimulated Acoustic Emission Method," Proc. IEEE Ultrasonics Symp., 1996, pp. 1459-1462.
Fatemi, et al., "Application of radiation force in noncontact measurement of the elastic parameters," Ultrasonic Imaging, vol. 21, No. 2, Apr. 1999 pp. 147-154.
Fatemi, et al., "Ultrasound-Stimulated Vibro-Acoustic Spectography," Science Magazine, vol. 280, No. 5360, 1998, pp. 82-85.
Fayed, Nirmeen et al. "Preoperative Thromboelastometry as a Predictor of Transfusion Requirements during Adult Living Donor Liver Transplantation." Transfusion medicine and hemotherapy : offizielles Organ der Deutschen Gesellschaft fur Transfusionsmedizin und Immunhamatologie vol. 42,2 (2015): 99-108. doi:10.1159/000381733.
Ferraris, et al., "2011 Update to the Society of Thoracic Surgeons and the Society of Cardiovascular Anesthesiologists Blood Conservation Clinical Practice Guidelines," Annals of Thoracic Surgery, vol. 91, 2011, pp. 944-982.
Feltner, et al., "Comparison of Various Time Delay Estimation Methods by Computer Simulation," IEEE Transactions on Acoustics, Speech, and Signal Processing, vol. 34, No. 5, 1986, pp. 1329-1330.
File History of U.S. Patent Application No. 16/146,333, dated Jul. 29, 2020, (156 pages). Exhibit 1013 to IPR2021-00293.
Final Office Action received in U.S. Appl. No. 16/201,522, dated Jan. 22, 2021, (20 pages).
Final Written Decision filed on Oct. 2, 2019. Exhibit 1011 to IPR2018-00950.
Flanders et al., "Evaluation and Performance Characteristics of the STA-R Coagulation Analyzer". Clin Chem., Sep. 2002; 48 (9): 1622-1624. PubMed P.M.I.D.: 12194955.
Flax, et al., "Phase-Aberration Correction Using Signals from Point Reflectors and Diffuse Scatterers: Basic Principles," IEEE Transactions on Ultrasonics Ferroelectrics & Frequency Control, vol. 35, No. 6, Nov. 1988, pp. 758-767.
Freedman, et al., "A Meta-Analysis of Thromboembolic Prophylaxis Following Elective Total Hip Arthroplasty," Journal of Bone and Joint Surgery, vol. 82-A, 2000, pp. 929-938.
Fricke, W., Kouides, P., Kessler, C., Schmaier, A.H., Krijanovski, Y., Jagadeesen, K., Joist, J., A multicenter clinical evaluation of the Clot Signature Analyzer. J. Thromb. Hasemostasis. 2004; 2: 763-8.
Gaetano, G. de, et al., "Effect of Platelets on Clot Structuration, a Thrombelastographic Study," Thrombosis Research, vol. 3, No. 4, pp. 425-435, 1973.
Gallippi, et al., "Adaptive clutter filtering via blind source," Ultrasonic Imaging, vol. 24, No. 4, 2002, pp. 193-214.
Gallippi, et al., "BSS-based filtering of physiological and ARFI induced tissue and blood motion," Ultrasound in Medicine and Biology, vol. 29, No. 11, 2003, pp. 1583-1592.
Gallippi, et al., "Complex blind source separation for acoustic radiation force impulse imaging in the peripheral vasculature, in vivo," IEEE Ultrasonics Symposium, vol. 1, 2004, pp. 596-601.
Ganter et al., "Kaolin-Based Activated Coagulation Time Measured by Sonoclot in Patients Undergoing Cardiopulmonary Bypass." J. Cardiothorac. Vasc. Anesth, Aug. 2007; 21 (4): 524-8. PubMed P.M.I.D.: 17678778.

(56) References Cited

OTHER PUBLICATIONS

Ganter, et al., "Active, personalized, and balanced coagulation management saves lives in patients with massive bleeding," Anesthesiology, vol. 133, No. 5, Nov. 2010, pp. 1016-1018.

Gauss, et al., "Adaptive Imagining in the Thyroid Using Fundamental and Harmonic Echo Data," presented at IEEE Ultrasonics Symposium, 1999, pp. 1515-1519.

Gauss, et al., "Wavefront Estimation in the Human Breast," presented at SPIE Medical Imaging, vol. 4325, 2001, pp. 172-180.

Giunta, et al., "Estimation of Global Motion Parameters by Complex Linear Regression," IEEE Transactions on Image Processing, vol. 8, No. 11, 1999, pp. 1652-1657.

Glidden, Paul F., et al., "Thromboelastograph Assay for Measuring the Mechanical Strength of Fibrin Sealant Clots," Clinical and Applied Thombosis / Hemostasis, vol. 6, No. 4, Oct. 2000, pp. 226-233.

Gorlinger et al., "Recommendations for using the ROTEM® in the management of perioperative bleeding in Cardiac Surgery" Recommendations from the ROTEM® Expert Meeting Working Group, Munich 2007, 10 pages.

Gosselin et al., "Monitoring Oral Anticoagulant Therapy with Point-of-Care Devices: Correlations and Caveats". Clin. Chem., Sep. 1997; 43 (9): 1785-6. PubMed P.M.I.D.: 9299978.

Greilich, Philip E., et al., "A Modified Thromboelastographic Method for Monitoring c7E3 Fab in Heparinized Patients," Anesth Analg, vol. 84, 1997, pp. 31-38.

Gurbel, et al., "Platelet function monitoring in patients with coronary artery disease," Journal of the American College of Cardiology, vol. 50, No. 19, Nov. 2007, pp. 1822-1834.

Hardisty R. M. et al, "Fibrinogen as a Co-factor in the Reaction of Platelets with Kaolin," May 7, 1966, Nature Publishing Group, Edition 210, vol. 644 (http://www.nature.com/nature/journal/v210/n5036/abs/210644a0.html).

Harris, et al., "Evaluation of recurrent thrombosis and hypercoagulability," American Family Physician, vol. 56, No. 6, Oct. 1997, pp. 1591-1596, pp. 1601-1602.

Harrison, P. Platelet Function Analysis. Blood Rev. Mar. 2005; 19 (2): 111-23. Review. PubMed P.M.I.D.: 15603914.

Hartley, et al., "Characteristics of Acoustic Streaming Created and Measured by Pulsed Doppler Ultrasound," IEEE Transactions on Ultrasonics, Ferroelectrics, and Frequency Control, vol. 44, No. 6, Nov. 1997, pp. 1278-1285.

Hartley, et al., "Doppler Measurement of Acoustic Streaming," IEEE Ultrasonics Symposium Proceedings, 1995, pp. 1537-1540.

Hemostasis and Thrombosis: Basic Principles and Clinical Practice Third edition. Edited by Robert W. Colman et al., 1827 pp. 1-25, illustrated. Philadelphia, Lippincott Company, 1994.

Hett, et al., "Sonoclot Analysis," British Journal of Anaesthesia, vol. 75, No. 6, Dec. 1995, pp. 771-776. Review. PubMed P.M.I.D.: 8672329.

Hirsh et al., "Oral anticoagulants. Mechanism of Action, Clinical Effectiveness, and Optimal Therapeutic Range". Chest. Oct. 1992; 102 (4 Suppl.): 312S-326S. Review. PubMed P.M.I.D.: 1345417.

Hirsh, et al., "How we diagnose and treat deep vein thrombosis," Blood, vol. 99, 2002, pp. 3102-3110.

Hirsh, et al., "Management of deep vein thrombosis and pulmonary embolism. A statement for healthcare professionals," Council on Thrombosis (in consultation with the Council on Cardiovascular Radiology), American Heart Association, vol. 93, 1996, 55 pages.

Huang, et al., "Detection of blood coagulation and clot formation using quantitative ultrasonic parameters," Ultrasound in Medicine and Biology, vol. 31, No. 11, Nov. 2005, pp. 1567-1573.

Huang, et al.," Characterization of Blood Properties from Coagulating Blood of Different Hematocrits Using Ultrasonic Backscatter and Attenuation", Japanese Journal of Applied Physics, vol. 45, No. 9A, 2006, pp. 7191-7196.

Ickx, Brigitte, "Point-of-Care Monitoring of Haemostasis in the OR and the ICU," European Society of Anaesthesiologists. Jun. 5, 2004, pp. 79-83.

*Instrumentation Laboratory Co. v. HemoSonics LLP*, IPR201700852, Paper No. 47 (PTAB Feb. 13, 2019) ("852 FWD"), 25 pages.

*Instrumentation Laboratory Co. v. HemoSonics LLP*, IPR201700855, Paper No. 55 (PTAB Feb. 13, 2019) ("971 FWD"), 55 pages.

International Preliminary Report on Patentability & Written Opinion, dated Aug. 27, 2013, in connection with International Application No. PCT/US2012/025278.

International Preliminary Report on Patentability & Written Opinion, dated Mar. 20, 2012, in connection with International Application No. PCT/US2010/049342.

International Preliminary Report on Patentability & Written Opinion, dated Nov. 19, 2013, in connection with International Application No. PCT/US2012/038553.

International Preliminary Report on Patentability & Written Opinion, dated Oct. 8, 2013, in connection with Application International No. PCT/US2012/025270.

International Preliminary Report on Patentability & Written Opinion, dated Oct. 9, 2012, in connection with Application International No. PCT/US2011/031832.

International Search Report & Written Opinion of the International Searching Authority, received in corresponding application No. PCT/US2010/049342, dated Nov. 16, 2010.

International Search Report & Written Opinion of the International Searching Authority, received in corresponding application No. PCT/US2011/031832, dated Dec. 15, 2011.

International Search Report, dated Aug. 20, 2013, in connection with International Application No. PCT/US2012/025278.

International Search Report, dated Jan. 2, 2013, in connection with International Application No. PCT/US2012/038553.

International Search Report, dated Sep. 30, 2013, in connection with International Application No. PCT/US2012/025270.

Ivandic et al., "Determination of Clopidogrel Resistance by Whole Blood Platelet Aggregometry and Inhibitors of the P2Y12 Receptor". Clinical Chemistry, vol. 52, No. 3, Mar. 2006, pp. 383-388. PubMed P.M.I.D.: 16423907.

Jacovitti, et al., "Discrete Time Techniques for Time Delay Estimation," IEEE Transactions on Signal Processing, vol. 41, No. 2, Feb. 1993, pp. 525-533.

Janus TJ, Lewis SD, Lorand L, Shafer JA. Promotion of thrombin-catalyzed activation of factor XIII by fibrinogen. Biochemistry. Dec. 20, 1983;22(26):6269-72. doi: 10.1021/bi00295a035. PMID: 6661434.

Japanese Office Action in International Application No. JP2015191180, dated Nov. 17, 2017, (9 pages including English Translation).

Jensen, "A New Method for Estimation of Velocity Vectors," IEEE Transactions on Ultrasonics, Ferroelectrics and Frequency Control, vol. 45, No. 3, 1998, pp. 837-851.

Jensen, Estimation of Blood Velocities Using Ultrasound, 1996, pp. 195-225.

Jensen, et al., "Calculation of pressure fields from arbitrarily shaped, apodized, and excited ultrasound transducers," IEEE Transactions on Ultrasonics, Ferroelectrics, and Frequency Control, vol. 39, 1992, pp. 262-267.

Jobes et al., "Increased Accuracy and Precision of Heparin and Protamine Dosing Reduces Blood Loss and Transfusion in Patients Undergoing Primary Cardiac Operations". J. Thorac. Cardiovasc. Surg. Jul. 1995; 110 (1): 36-45. PubMed P.M.I.D.: 7609566.

Jolliffe, IT., "Principal Component Analysis," Springer Series in Statistics, 2nd edition, Springer, NY, 2002.

Kadi, et al., "On the performance of regression and step-initialized IIR Clutter Filters," IEEE Transactions on Ultrasonics, Ferroelectrics, and Frequency Control, vol. 42, 1995, pp. 827-837.

Kasai, et al., "Real-time Two-Dimensional Blood Flow Imaging Using an Autocorrelation Technique," IEEE Ultrasonics Symposium, vol. 32, No. 3, 1985, pp. 458-464.

Katori, et al., "The effects of platelet count on clot retraction and tissue plasminogen activator-induced fibrinolysis on thrombelastography," Anesthesia and Analgesia, vol. 100, No. 6, Jun. 2005, pp. 1781-1785.

Keith B. Neeves, Curriculum Vita, Sep. 1, 2020, (25 pages). Exhibit 1003 to IPR2021-00293.

Kereiakes et al., "Time Course, Magnitude, and Consistency of Platelet Inhibition by Abciximab, Tirofiban, or Eptifibatide in Patients

(56) References Cited

OTHER PUBLICATIONS with Unstable Angina Pectoris Undergoing Percutaneous Coronary Intervention". Am. J. Cardiol., Aug. 15, 1999; 84 (4): 391-5 .PubMed P.M.I.D.: 10468074.

Keresztes, et al., "The PFA-100: analysis and interpretation of a platelet function measurement," The Journal of Cardiovascular Nursing, vol. 20, No. 6, 2005, pp. 405-407.

Kettner, S.C., et al., "Use of abciximab—Modified Thrombelatography in Patients Undergoing Cardiac Surgery," Anesth Analg, vol. 89, 1999, pp. 580-584.

Khurana, Sandeep, et al., "Thromboelastography Can Rapidly Bioassay Fibrinogen," Anesthesiology, vol. 85, No. 3A, Sep. 1996, p. A457.

Koepke, J., "Point-of-Care Coagulation Testing," Laboratory Medicine, vol. 31, No. 6, Jun. 2000, pp. 343-346.

Koster et al., "Evaluation of Post-Cardiopulmonary Bypass Coagulation Disorders by Differential Diagnosis with a Multichannel Modified Thromboelastogram: A Pilot Investigation". J. Extra. Corpor. Technol., Sep. 2001; 33 (3): 153-8. PubMed P.M.I.D.: 11680728.

Kozek-Langenecker, S. Intensive Care Medicine, Annual Update 2007, Monitoring of Hemostasis in Emergency Medicine, pp. 847-860, Springer New York.

Kruse, et al., "A new high-resolution color flow system using an eigendecomposition-based adaptive filter for clutter rejection," IEEE Transactions on Ultrasonics, Ferroelectrics, and Frequency Control, vol. 49, No. 10, 2002, pp. 1384-1399.

Kuntamukkula MS, McIntire LV, Moake JL, Peterson DM, Thompson WJ. Rheological studies of the contractile force within plateletfibrin clots: effects of prostaglandin E1, dibutyryl-cAMP and dibutyrylcGMP. Thromb Res. Dec. 1978;13(6):957-69. doi: 10.1016/0049-3848(78)90225-6. PMID: 219559.

Lang T, von Depka M. Diagnostische Möglichkeiten und Grenzen der Thrombelastometrie/-graphie [Possibilities and limitations of thrombelastometry/-graphy]. Hamostaseologie. Aug. 2006;26(3 Suppl 1):S20-9. English Translation, with Declaration. PMID: 16953288.

Lang T, von Depka M. Diagnostische Möglichkeiten und Grenzen der Thrombelastometrie/-graphie [Possibilities and limitations of thrombelastometry/-graphy]. Hamostaseologie. Aug. 2006;26(3 Suppl 1):S20-9. German. PMID: 16953288.

Lang, T. & Depka, M.. (2006). Possibilities and limitations of thromboelastometry/thromboelastography. Hamostaseologie. 26. S21-S29. 10.1055/s-0037-1617078.

Ledoux, et al., "Reduction of the clutter component in Doppler ultrasound signals based on singular value decomposition: a simulation study," vol. 19, No. 1, 1997, pp. 1-18.

Lerner, et al., "Sono-elasticity: medical elasticity images derived from ultrasound signals in mechanically vibrated targets," Ultrasound in Medicine & Biology, vol. 16, 1998, pp. 317-327.

Li et al., "The Xylum Clot Signature Analyzer: A Dynamic Flow System that Simulates Vascular Injury". Thromb. Res., Dec. 15, 1998; 92 (6 Suppl. 2): S67-77. PubMed P.M.I.D.: 9886913.

Loupas, et al., "An axial Velocity Estimator for Ultrasound Blood flow imaging, by means of a two-dimensional autocorrelation approach," IEEE Transactions on Ultrasonics, Ferroelectrics, and Frequency Control, vol. 42, No. 4, 1995, pp. 672-688.

Lubinski, et al., "Adaptive strain estimation using retrospective processing medical US elasticity imaging," IEEE Transactions on Ultrasonics Ferroelectrics & Frequency Control, vol. 46, 1999, pp. 97-107.

Machado et al., "Evaluation of an Ultrasonic Method Applied to the Measurement of Blood Coagulation Time". Physiol. Meas., May 1997; 18 (2): 129-43. PubMed P.M.I.D.: 9183807.

Mahla, et al., "Thromboelastography for monitoring prolonged hypercoagulability after major abdominal surgery," Anesthesia and Analgesia, vol. 92, No. 3, Mar. 2001, pp. 572-577.

Malinin, et al., "Validation of a VerifyNow-P2Y12 cartridge for monitoring platelet inhibition with clopidogrel," Methods and Findings in Experimental and Clinical Pharmacology, vol. 28, No. 5, Jun. 2006, pp. 315-322.

Mauldin, et al., "Robust Principal Component Analysis and Clustering Methods for Automated Classification of Tissue Response to ARFI Excitation," Ultrasound in Medicine & Biology, vol. 34, No. 2, 2008, pp. 309-325.

McAleavey, et al., "Estimates of echo correlation and measurement bias in acoustic radiation force impulse imaging," IEEE Transactions on Ultrasonics Ferroelectrics & Frequency Control, vol. 50, 2003, pp. 631-641.

Moake J Overview of Hemostasis. Merck Manuals 2016 http://www.merckmanuals.com/professional/hematology-and-oncology/hemostasis/overview-of-hemostasis.

Motovska et al., "Benefits and Risks of Clopidogrel Use in Patients with Coronary Artery Disease: Evidence from Randomized Studies and Registries". Clin. Ther., 2008; 30 Pt. 2: 2191-202. J. Clinthera., 2008.12.001. Review. PubMed P.M.I.D.: 19281914.

Mueller et al., "Utility of the PFA-100 Instrument and the Novel Multiplate Analyzer for the Assessment of Aspirin and Clopidogrel Effects on Platelet Function in Patients with Cardiovascular Disease". Clin. Appl. Thromb. Hemost., Dec. 2009; 15 (6): 652-9. PubMed P.M.I.D.: 18805846.

Nam et al., "Evaluation of the Roche CoaguChek XS Handheld Coagulation Analyzer in a Cardiac Outpatient Clinic". Ann. Clin. Lab. Sci., 2008 Winter; 38 (1): 37-40. PubMed P.M.I.D.: 18316780.

Ng, et al., "A Comparative Evaluation of Several Algorithms for Phase Aberration Correction," IEEE Transactions on Ultrasonics Ferroelectrics & Frequency Control, vol. 41, No. 5, Sep. 1994, pp. 631-643.

Nielson, et al., "Effects of coagulation factor deficiency on plasma coagulation kinetics determined via thrombelastography: critical roles of fibrinogen and factors II, VII, X and XII," Acta Anesthesiologica Scandanavia, vol. 49, No. 2, Feb. 2005, pp. 222-231.

Nightingale, et al., "Acoustic Radiation Force Impulse Imaging: In Vivo Demonstration of Clinical Feasibility," Ultrasound in Medicine & Biology, vol. 28, 2002, pp. 227-235.

Nightingale, et al., "Acoustic remote palpation: initial in vivo results," presented at IEEE Ultrasonics Symposium, 2000, pp. 1553-1558.

Nightingale, et al., "Shear-Wave Generation Using Acoustic Radiation Force: In Vivo and EX Vivo Results," Ultrasound in Medicine & Biology, vol. 29, No. 12, 2003, pp. 1715-1723.

Notice of Allowance issued for U.S. Appl. No. 15/202,059, dated May 23, 2018.

Notice of Allowance issued for U.S. Appl. No. 15/991,677, dated Nov. 2, 2018.

O'Donnell, et al., "Internal Displacement and Strain Imaging using Ultrasonic Speckle Tracking," IEEE Transactions on Ultrasonics, Ferroelectrics and Frequency Control, vol. 41, 1994, pp. 314-325.

O'Donnell, et al., "Role of the Thrombelastograph as an adjunctive test in thrombophilia screening," Blood Coagulation and Fibrinolysis, vol. 15, No. 3, Apr. 2004, pp. 207-211.

Oberhardt, et al., "Dry reagent technology for rapid, convenient measurements of blood coagulation and fibrinolysis," Clinical Chemistry, vol. 37, No. 4, Apr. 1991, pp. 520-526.

Office Action issued for Canadian Application No. 2,823,729, dated Mar. 9, 2018.

Office Action issued for Canadian Application No. 2823729, dated Nov. 14, 2018, 4 pages.

Office Action issued for Chinese Application No. 2017101635956, dated Jul. 17, 2018.

Office Action issued for U.S. Appl. No. 15/904,984, dated Jul. 12, 2018.

Office Action received in co-pending U.S. Appl. No. 15/202,059, dated Jan. 12, 2018.

Office Action received in co-pending U.S. Appl. No. 15/202,059, dated Jul. 13, 2017.

Office Action received in co-pending U.S. Appl. No. 15/202,059, dated Oct. 4, 2016.

Office Action received in co-pending U.S. Appl. No. 15/644,124, dated Feb. 6, 2018.

Office Action received in co-pending U.S. Appl. No. 15/644,124, dated Nov. 29, 2017.

Office Action received in co-pending U.S. Appl. No. 15/644,124, dated Sep. 7, 2017.

(56) References Cited

OTHER PUBLICATIONS

Office Action received in U.S. Appl. No. 15/357,492, dated Jun. 22, 2017.
Ophir, et al., "Elastography: A Quantitative Method for Imaging the Elasticity of Biological Tissues," Ultrasonic Imaging, vol. 13, No. 2, 1991, pp. 111-134.
Packham, M., "Role of platelets in thrombosis and hemostasis," Canadian Journal of Physiology and Pharmacology, vol. 72, No. 3, Mar. 1994, pp. 278-284.
Pallister CJ, Watson MS (2010). Haematology. Scion Publishing. pp. 336-347. ISBN 1-904842-39-9.
Palmeri, et al., "Ultrasonic tracking of acoustic radiation force-induced displacements in homogeneous media," IEEE Transactions on Ultrasonics, Ferroelectrics, and Frequency Control, vol. 53, No. 7, 2006, pp. 1300-1313.
Parsons, et al., "Age Determiniation of Experimental Venous Thrombi by Ultrasonic Tissue Characterization," Journal of Vascular Surgery, vol. 17, 1993, 470-478.
Patil, et al., "3D prostate elastography: algorithm, simulations and experiments," Physics in Medicine & Biology, vol. 52, No. 12, 2007, pp. 3643-3663.
Peeters et al., "Ultrasonic Measurements of Coagulation and Fibrinolysis". J. Clin. Pathol., May 1964; 17: 320-3. PubMed P.M.I.D.: 14159472; PubMed Central P.M.C.I.D.: PMC480759.
Perry, et al., "Point-of-care testing in haemostasis," British Journal of Haematology, vol. 150, No. 5, Sep. 2010, pp. 501-514.
Pertinent Materials Reviewed and Considered by Keith Neeves, Ph.D. filed on Dec. 14, 2020. Exhibit 1019 to IPR2021-00293.
Petition for Inter Partes Review of U.S. Pat. No. 10,746,750 dated Dec. 14, 2020, 79 pages.
Pivalizza, et al., "Perioperative thromboelastography and sonoclot analysis in morbidly obese patients," Canadian Journal of Anaesthesia, vol. 44, No. 9, Sep. 1997, pp. 942-945.
Plotkin AJ, Wade CE, Jenkins DH, Smith KA, Noe JC, Park MS, Perkins JG, Holcomb JB. A reduction in clot formation rate and strength assessed by thrombelastography is indicative of transfusion requirements in patients with penetrating injuries. J Trauma. Feb. 2008;64(2 Suppl):S64-8. doi: 10.1097/TA.0b013e318160772d. PMID: 18376174.
Price et al., "Prognostic Significance of Post-Clopidogrel Platelet Reactivity Assessed by a Point-of-Care Assay on Thrombotic Events after Drug-Eluting Stent Implantation". Eur. Heart Apr. 2008; 29 (8): 992-1000. PubMed P.M.I.D.: 18263931.
Rao, G., "Need for a point-of-care assay for monitoring antiplatelet and antithrombotic therapies," Stroke, vol. 40, No. 6, Jun. 2009, pp. 2271-2272.
Riou, Chonavel et al., "Fast adaptive eigenvalue decomposition: a maximum likelihood approach," Signal Processing, 83, 2003, pp. 307-324.
Rotem Delta Targeted Therapy Stop the Bleeding. 2013. Exhibit 1027 to IPR2021-00293.
Rubin, et al., "Clinical application of sonographic elasticity imaging for aging of deep venous thrombosis: preliminary findings," Journal of Ultrasound in Medicine, vol. 22, 2003, pp. 443-448.
Ruzicka, K., et al. Evaluation of Bedside Prothrombin Time and Activated Partial Thromboplastin Time Measurement by Coagulation Analyzer COAGUCHECK PLUS in Various Clinical Settings. Throm. Res., 87 (5) 1997 pp. 431-440. See also, Hillman, R., 1988 U.S. Pat. No. 4,756,884. Capillary Fill Device.
Sakharov, et al., "Acceleration of Fibrinolysis by High-Frequency Ultrasound: The Contribution of Acoustic Streaming and Temperature Rise," Thrombosis Research, vol. 100, No. 4, 2000, pp. 333-340.
Sarvazyan, et al., "Shear Wave Elasticity Imagining—A New Ultrasonic Technology of Medical Diagnostics," Ultrasound in Medicine and Biology, vol. 24, 1998, pp. 1419-1436.
Scharbert et al., "Evaluation of the Platelet Mapping Assay on Rotational Thromboelastometry ROTEM". Platelets. Mar. 2009; 20 (2): 125-30. PubMed P.M.I.D. 19235055.

Schmitt, C., et al., "Characterization of blood clot viscoelasticity by dynamic ultrasound elastography and modeling of the rheological behavior," Journal of Biomechanics, vol. 44, No. 4, 2011, pp. 622-629.
Shi, et al., "Color Doppler Detection of Acoustic Streaming in a Hematoma Model," Ultrasound in Medicine and Biology, vol. 27, No. 9, 2001, pp. 1255-1264.
Shi, et al., "Color Doppler imaging of acoustic streaming in blood and clot," IEEE Ultrasonics Symposium, vol. 2, 1999, pp. 1315-1318.
Shi, et al., "Experimental Investigation and Finite Element Simulation of Streaming in Blood in Cylindrical Models," IEEE Ultrasonics Symposium, vol. 2, 2000, pp. 1509-1512.
Shi, Quantitative Investigation of Acoustic Streaming in Blood, J. Acoust. Soc. Am. 111, Feb. 2002, pp. 1110-1121.
Shih, C-C, et al., "In Vitro Assessments of Viscoelastic Properties of Fibrin Clot by Using Acoustic Radiation Force on a Solid Sphere," International Ultrasonics Symposium Proceedings, IEEE, 2010, pp. 479-482.
Shore-Lesseron., Evidence Based Coagulation Monitors: Heparin Monitoring, Thromboelastography, and Platelet Function Sem. Cardiothoracic Vasc. Anesthesia., Mar. 2005; 9 (1): 42-52.
Shung, et al., "Ultrasonic characterization of blood during coagulation," Journal of Clinical Ultrasound, vol. 12, No. 3, 1984, pp. 147-153.
Skovoroda, et al., "Tissue elasticity reconstruction based on ultrasonic displacement and strain images," IEEE Transactions on Ultrasonics, Ferroelectrics, and Frequency Control, vol. 42, No. 4, 1995, pp. 747-765.
Spiel, A. O. et al,, "Validation of rotation thrombelastography in a model of systemic activation of fibrinolysis coagulation and in humans", Journal of Thrombosis and Haemostasis, 2006; 4: 411-416.
Srinivasan, et al., "Elastographic imaging using staggered strain estimates," Ultrasonic Imaging, vol. 24, 2002, pp. 229-245.
Strobach, P., "Low-rank adaptive filters," IEEE Trans Signal Process, vol. 44, No. 12, 1996, pp. 2932-2947.
Sugimoto, et al., "Tissue Hardness Measurement Using the Radiation Force of Focused Ultrasound," Proc. IEEE Ultrason Symp., 1990, pp. 1377-1380.
Sumino, et al., "Measurements of ultrasonic pulse arrival time differences produced by abdominal wall specimens," Journal of the Acoustical Society of America, vol. 90, No. 6, 1991, pp. 2924-2930.
Taborski et al., "Analytical Performance of the New Coagulation Monitoring System INRatio for the Determination of INR Compared with the Coagulation Monitor Coaguchek S and an Established Laboratory Method" J. Thromb. Thrombolysis. Oct. 2004; 18 (2): 103-7. PubMed P.M.I.D.: 15789176.
Third party observation filed in European Patent Application No. 11766842.6, dated Mar. 6, 2016, 10 pages.
Third party observation filed in U.S. Appl. No. 15/202,059, filed Nov. 30, 2016, 40 pages.
Thuerlemann, et al., "Monitoring thrombin generation by electrochemistry: development of an amperometric biosensor screening test for plasma and whole blood," Clinical Chemistry, vol. 55, No. 3, Mar. 2009, pp. 505-512.
Tomauiolo, M., Brass, L.F., Stalker, T.J., Regulation of Platelet Activation and Coagulation and Its Role in Vascular Injury and Arterial Thrombosis. Interv. Cardiol. Clin. Jan. 2017; 6 (1): 1-12.
Toner, et al., "Blood-on-a-chip," Annual Review of Biomedical Engineering, vol. 7, 2005, pp. 77-103.
Torr, "The Acoustic Radiation Force," Am. J. Phys., vol. 52, 1984, pp. 402-408.
Trahey, et al., "Synthetic receive aperture imaging with correction for motion and for tissue inhomogeneities. II. Effects of and correction for motion," IEEE Transactions on Ultrasonics, Ferroelectrics, and Frequency Control, vol. 39, No. 4, 1992, pp. 496-501.
Traverso C, Arcelus JI, Gomez E, Luna D, Lopez-Cantarero M, Garcia JM. "Prospective assessment of the risk of deep vein thrombosis in elective abdominal surgery. Predictive role of [Thrombelastograph® analysis]." Thromb Haemorrh Disorders. 1993: 71: 9-15.

(56) References Cited

OTHER PUBLICATIONS

Trial Board Order for Inter Partes Review of U.S. Pat. No. 9,272,280 B2, 13 pages.
Trial Board Order for Inter Partes Review of U.S. Pat. No. 9,410,971 B2, 27 pages.
Trial Paper for Inter Partes Review of U.S. Pat. No. 9,272,280 B2 dated Jul. 11, 2018, 10 pages.
Trial Paper for Inter Partes Review of U.S. Pat. No. 9,410,971 dated Aug. 28, 2018, 3 pages.
Trial Paper for Inter Partes Review of U.S. Pat. No. 9,410,971 dated Dec. 1, 2017, 4 pages.
Trial Paper for Inter Partes Review of U.S. Pat. No. 9,410,971 dated Jul. 11, 2018, 10 pages.
Trial Paper for Inter Partes Review of U.S. Pat. No. 9,410,971 dated Oct. 2, 2017, 11 pages.
Tripodi et al., "International Sensitivity Index Calibration of the Near-Patient Testing Prothrombin Time Monitor, Pro Time". Am. J. Clin. Pathol., Feb. 2003; 119 (2): 241-5. PubMed P.M.I.D.: 12579994.
Versteeg et al., "New Fundamentals in Hemostasis", Physiol. Rev. Jan. 2013; 93 (1): 327-58. Review. PubMed P.M.I.D.: 23303912.
Vig, et al., "Thromboelastography: a reliable test ?" Blood Coagulation and Fibrinolysis, vol. 12, No. 7, Oct. 2001, 555-561.
Viola, et al., "A Comparison between spline-based and phase domain time-delay estimators," IEEE Transactions on Ultrasonics, Ferroelectrics, and Frequency Control, vol. 53, No. 3, 2006, pp. 515-517.
Viola, et al., "A comparison of the performance of time-delay estimators in medical ultrasound," IEEE Transactions on Ultrasonics Ferroelectrics & Frequency Control., vol. 50, 2003, pp. 392-401.
Viola, et al., "A Spline Based Algorithm for Continuous Time Delay Estimation Using Sampled Data," IEEE on Ultrasonics Ferroelectrics & Frequency Control, in press, 2005, pp. 80-93.
Viola, et al., "Analysis of Clot Formation with Acoustic Radiation Force," SPIE Proceedings, vol. 4689, 2002, pp. 235-242 and pp. 1-2.
Viola, et al., "Comparison of Time Delay Estimators in Medical Ultrasound," IEEE Ultrasonics Symposium, vol. 2, 2001, pp. 1485-1488.
Viola, et al., "Efficient and Accurate Spline-Based Time Delay Estimation," IEEE Ultrasonics Symposium, vol. 2, 2004, pp. 870-873.
Viola, et al., "Imaging Viscoelastic Properties of the Vitreous," Ultrasonics Symposium, vol. 2, 2001, pp. 1623-1626.
Viola, et al., "Radiation Force Imaging of Viscoelastic Properties with Reduce Artifacts," IEEE Transactions on Ultrasonics, Ferroelectrics, and Frequency Control, vol. 50, No. 6, 2003, pp. 736-742.
Viola, et al., "Ultrasound echo decorrelation due to acoustic radiation force," IEEE Ultrasonics Symposium Proceedings, vol. 2, 2002, pp. 1903-1906.
Voleišis, A., et al., "Ultrasonic method for the whole blood coagulation analysis," Ultrasonics, vol. 40, May 2002, pp. 101-107.
Walker, et al., "A Fundamental Limit on Delay Estimation Using Partially Correlated Speckle Signals," IEEE Transactions on Ultrasonics, Ferroelectrics and Frequency Control, vol. 42, 1995, pp. 301-308.
Walker, et al., "A Fundamental Limit on the Accuracy of Speckle Signal Alignment," IEEE Ultrasonics Symposium Proceedings, vol. 3, 1994, pp. 1787-1791.
Walker, et al., "A Method of Imagining Viscoelastic Parameters with Acoustic Radiation Force," Physics in Medicine and Biology, vol. 45, No. 6, 2000, pp. 1437-1447.
Walker, et al., "Application of Acoustic Radiation Force in Ophthalmic Ultrasound," Proc. IEEE Ultrason. Symp., vol. 2, 1997, pp. 1291-1295.
Walker, et al., "Real-Time Imaging of Tissue Vibration Using a Two-Dimensional Speckle Tracking System," IEEE Ultrason. Symp., 1993, pp. 873-877.
Walker, et al., "The Significance of Correlation in Ultrasound Signal Processing," SPIE Proceedings, vol. 4325, 2001, pp. 159-171.
Webster, Medical Instrumentation: Application and Design, New York: John Wiley & Sons, 1998, 6 pages.
Weisel JW. The mechanical properties of fibrin for basic scientists and clinicians. Biophys Chem. Dec. 20, 2004;112(2-3):267-76. doi: 10.1016/j.bpc.2004.07.029. PMID: 15572258.
Weiss, H J et al. "The effect of salicylates on the hemostatic properties of platelets in man." The Journal of clinical investigation vol. 47,9 (1968): 2169-80. doi:10.1172/JCI105903.
Westbrook, et al., "Protocol based on thromboelastograph (TEG) out-performs physician preference using laboratory coagulation tests to guide blood replacement during and after cardiac surgery: a pilot study," Heart, Lung, and Circulation, vol. 18, No. 4, Aug. 2009, pp. 277-288.
Whitten, et al., "Thromboelastography: past, present, and future," Anesthesiology, vol. 92, No. 5, May 2000, pp. 1223-1225.
Wolberg AS. Plasma and cellular contributions to fibrin network formation, structure and stability. Haemophilia. May 2010;16 Suppl 3:7-12. doi: 10.1111/j.1365-2516.2010.02253.x. PMID: 20586795.
Wolff et al., "Aspirin for the Primary Prevention of Cardiovascular Events: an Update of the Evidence for the U.S. Preventive Services Task Force". Ann. Intern. Med., Mar. 17, 2009; 150 (6): 405-10. Review. PubMed P.M.I.D.: 19293073.
Yu, et al., "Single-Ensemble-Based Eigen-Processing Methods for Color Flow Imaging," IEEE Transactions on Ultrasonics, Ferroelectrics, and Frequency Controls, vol. 55, No. 3, 2008, pp. 573-587.
Request for Ex Parte Reexamination of U.S. Pat. No. 11,061,038 Filed by a Third Party Requester Nov. 3, 2021, 341 pages.
Appendix A of Request for Ex Parte Reexamination of U.S. Pat. No. 11,061,038 filed by a Third Party Requester, Nov. 3, 2021, 102 pages.
Appendix B of Request for Ex Parte Reexamination of U.S. Pat. No. 11,061,038 filed by a Third Party Requester, Nov. 3, 2021, 112 pages.
Appendix C of Request for Ex Parte Reexamination of U.S. Pat. No. 11,061,038 filed by a Third Party Requester, Nov. 3, 2021, 126 pages.
Appendix D of Request for Ex Parte Reexamination of U.S. Pat. No. 11,061,038 filed by a Third Party Requester, Nov. 3, 2021, 139 pages.
Exhibit 1001. U.S. Pat. No. 11,061,038, dated Jul. 13, 2021, of Request for Ex Parte Reexamination filed by a Third Party Requester, Nov. 3, 2021, 39 pages.
Exhibit 1002. File History of U.S. Pat. No. 11,061,038, dated Jul. 13, 2021, of Request for Ex Parte Reexamination filed by a Third Party Requester, Nov. 3, 2021, 417 pages.
Exhibit 1003. PTAB-IPR2018-00950 Declaration of Scott L. Diamond, of Request for Ex Parte Reexamination filed by a Third Party Requester, Nov. 3, 2021, 201 pages.
Exhibit 1004. U.S. Pat. No. 5,629,209, dated May 13, 1977, of Request for Ex Parte Reexamination filed by a Third Party Requester, Nov. 3, 2021, 39 pages.
Exhibit 1005. PTAB-IPR2018-00950 Lang 2006 (German), of Request for Ex Parte Reexamination filed by a Third Party Requester, Nov. 3, 2021, 14 pages.
Exhibit 1006. PTAB-IPR2018-00950 Lang 2006 (certified English translation), of Request for Ex Parte Reexamination filed by a Third Party Requester, Nov. 3, 2021, 28 pages.
Exhibit 1007. PTAB-IPR2018-00950 Lang 2006 (Supplemental English translation), of Request for Ex Parte Reexamination filed by a Third Party Requester, Nov. 3, 2021, 10 pages.
Exhibit 1908. IPR2021-00293 Statutory Disclaimer, of Request for Ex Parte Reexamination filed by a Third Party Requester, Nov. 3, 2021, 4 pages.
Exhibit 1009. U.S. Pat. No. 6,016,712, issued Jan. 25, 2000, of Request for Ex Parte Reexamination filed by a Third Party Requester, Nov. 3, 2021, 24 pages.
Exhibit 1010. U.S. Pat. No. 9,915,671, dated May 13, 2018, of Request for Ex Parte Reexamination filed by a Third Party Requester, Nov. 3, 2021, 25 pages.
Exhibit 1011. IPR2018-00950 Final Written Decision (Paper 30), of Request for Ex Parte Reexamination filed by a Third Party Requester, Nov. 3, 2021, 50 pages.

(56) References Cited

OTHER PUBLICATIONS

Exhibit 1012. IPR2021-00293 Petition for IPR of Patent No. 10,746,750 (Paper 2), of Request for Ex Parte Reexamination filed by a Third Party Requester, Nov. 3, 2021, 80 pages.
Exhibit 1013. IPR2021-00293 Trial instituted Decision (Paper 9), of Request for Ex Parte Reexamination filed by a Third-Party Requester, Nov. 3, 2021, 30 pages.
Exhibit 1014. IPR2018-00950 Petition for IPR of Patent No. 9,915,671 (Paper 2), of Request for Ex Parte Reexamination filed by a Third-Party Requester, Nov. 3, 2021, 77 pages.
Exhibit 1015. IPR2018-00950 Patent Owner's Response (Paper 13), of Request for Ex Parte Reexamination filed by a Third-Party Requester, Nov. 3, 2021, 38 pages.
Exhibit 1016. IPR2018-00950 General Order (Paper 34), of Request for Ex Parte Reexamination filed by a Third-Party Requester, Nov. 3, 2021, 7 pages.
Exhibit 1017. IPR2021-00293 Patent Owner's Response (Paper 11), of Request for Ex Parte Reexamination filed by a Third-Party Requester, Nov. 3, 2021, 25 pages.
Exhibit 1018. Dictionary.com online dictionary—cavity; ductwork; duct, of Request for Ex Parte Reexamination filed by a Third-Party Requester, Nov. 3, 2021, 22 pages.
Exhibit 1019. IPR2018-00950 Petitioner's Reply to Patent Owner's Response (Paper 19), of Request for Ex Parte Reexamination filed by a Third-Party Requester, Nov. 3, 2021, 33 pages.
Exhibit 1020. U.S. Patent Publication No. 2005220668A1, published Oct. 6, 2005, of Request for Ex Parte Reexamination filed by a Third Party Requester, Nov. 3, 2021, 18 pages.
Exhibit 1021. U.S. Pat. No. 6,613,286, dated Sep. 2, 2003, of Request for Ex Parte Reexamination filed by a Third Party Requester, Nov. 3, 2021, 20 pages.
Exhibit 1022. U.S. Patent Publication No. 20040189311A1, published Sep. 30, 2004, of Request for Ex Parte Reexamination filed by a Third Party Requester, Nov. 3, 2021, 91 pages.
Exhibit 1023. U.S. Patent Publication No. 20050233460A1, published Oct. 20, 2005, of Request for Ex Parte Reexamination filed by a Third Party Requester, Nov. 3, 2021, 32 pages.
Exhibit 1024. Straub et el., of Request for Ex Parte Reexamination filed by a Third Party Requester, Nov. 3, 2021, 8 pages.
Transmittal of Request for Ex Parte Reexamination of U.S. Pat. No. 11,061,038 Filed by a Third Party Requester Nov. 3, 2021, 3 pages.
Electronic Acknowledgment Receipt of Request for Ex Parte Reexamination of U.S. Pat. No. 11,061,038 Filed by a Third Party Requester Nov. 3, 2021, 7 pages.
Information Disclosure Statement accompanying Request for Ex Parte Reexamination of U.S. Pat. No. 11,061,038 Filed by a Third Party Requester Nov. 3, 2021, 2 pages.
Ex Parte Reexamination Decision for U.S. Pat. No. 11,061,038, dated Dec. 10, 2021, 15 pages.
Order Granting Request For Ex Parte Reexamination of U.S. Pat. No. 11,061,038, dated Dec. 10. 2021, 15 pages.
Paper 10, Scheduling Order for IPR2021-00293 of U.S. Pat. No. 10,746,750, dated Jul. 11, 2021, 11 pages.
Paper 9, Decision Granting Institution of Inter Partes Review under 35 U.S.C. § 314 for IPR2021-00293 of U.S. Pat. No. 10,746,750, dated Jul. 1, 2021, 29 pages.
Patent Owner's Response to Petition under 37 C.F.R. §42.120 for IPR2021-002S3 of U.S. Pat. No. 10,746,750, filed Sep. 24, 2021, 24 pages.
Patent Owner's Preliminary Response for IPR2021-00293 of U.S. Pat. No. 10,746,750, filed Apr. 22, 2021, 6 pages.
Petitioner's Reply to Patent Owner's Response under 37 C.F.R. §42.120 for IPR2021-00293 of U.S. Pat. No. 10,746,750, filed Dec. 16, 2021, 30 pages.
Exhibit 1004. Response to Non-Final Office Action for IPR2021-00293 of U.S. Appl. No. 16/146,333, filed Dec. 19, 2019, 10 pages.
Exhibit 2001. Statutory Terminal Disclaimer for IPR2021-00293 of U.S. Pat. No. 10,746,750, filed Apr. 22, 2021, 3 pages.
Exhibit 1031, Paper 21, Patent Owner's Sur-Reply for IPR2018-00950 of U.S. Pat. No. 9,915,671, filed May 6, 2019, 34 pages.
Exhibit. 1030, Paper 19, Petitioner's Reply to Patent Owner's Response for IPR2018-00950 of U.S. Pat. No. 9,915,671, filed Apr. 4, 2019, 32 pages.
Exhibit 2003, Definition of "Duct" retrieved from Dictionary.com., for IPR2021-00293 of U.S. Pat. No. 10,746,750, filed Apr. 22, 2021, 8 pages.
Exhibit 1032, Request for Rehearing for IPR2018-00950 of U.S. Pat. No. 9,915,671, filed Nov. 1, 2019, 15 pages.
Exhibit. 1029, Patent Owner's Response for IPR2018-00950 of U.S. Pat. No. 9,915,671, filed Jan. 4, 2019, 37 pages.
Straub, Andreas, et al., "Using reagent-supported thromboelastometry (ROTEMW) to monitor haemostatic changes in congenital heart surgery employing deep hypothemic circulatory arrest," European Journal of Cardio-thoracic Surgery 34 (2008) 641-647. (Year: 2008).
Non-Final Office Action dated Nov. 2, 2021, U.S. Appl. No. 17/372,637, filed Jul. 12, 2021 (19 pages).
Non Final Office Action dated Jan. 14, 2021, U.S. Appl. No. 17/343,960, filed Jun. 10, 2021 (11 pages).

\* cited by examiner

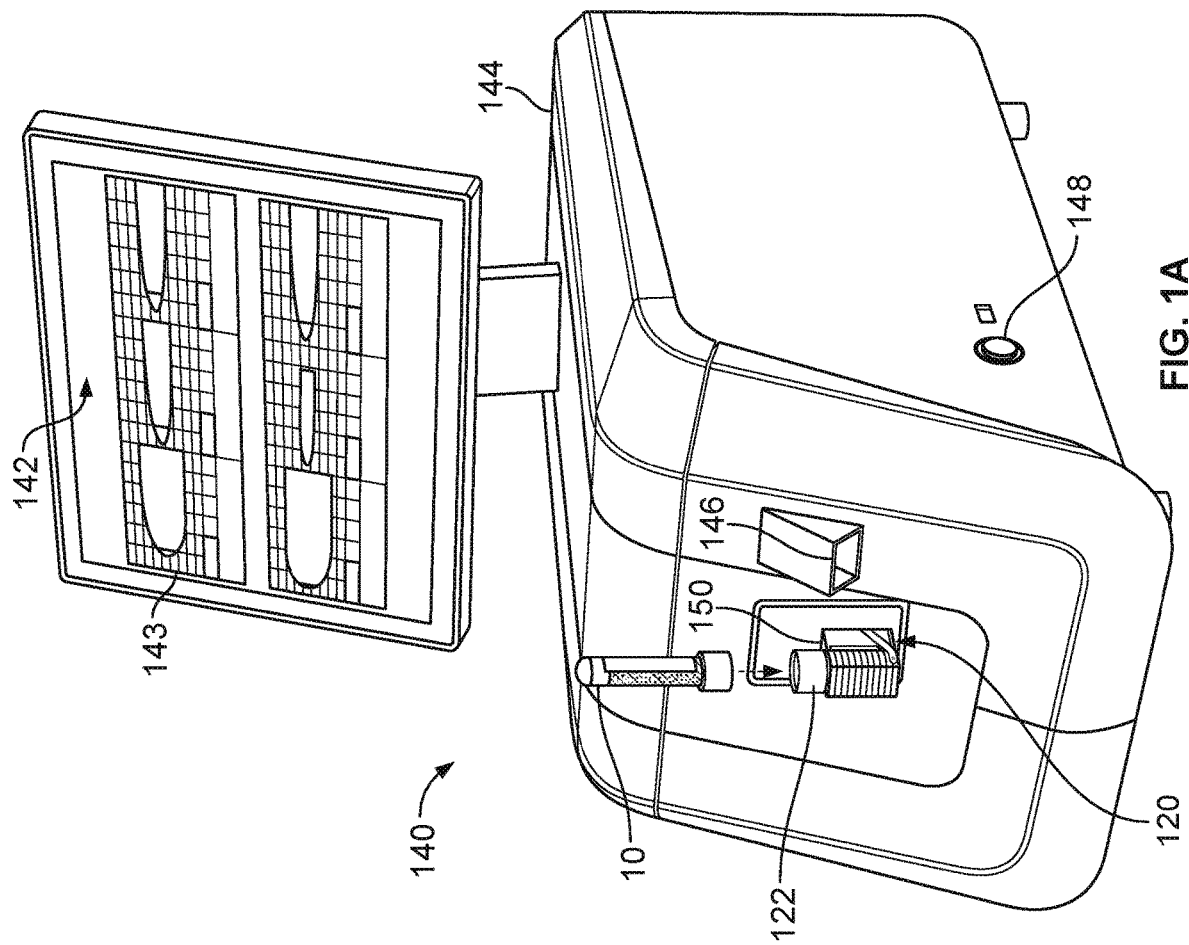
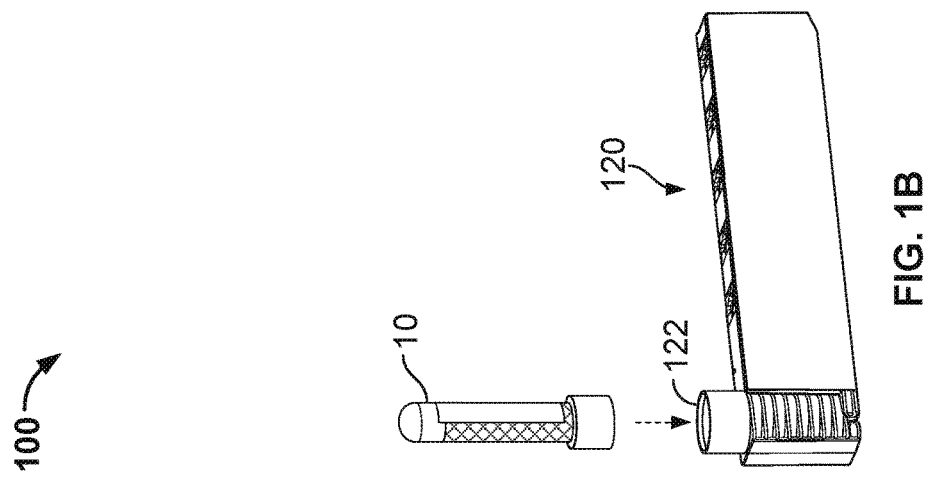

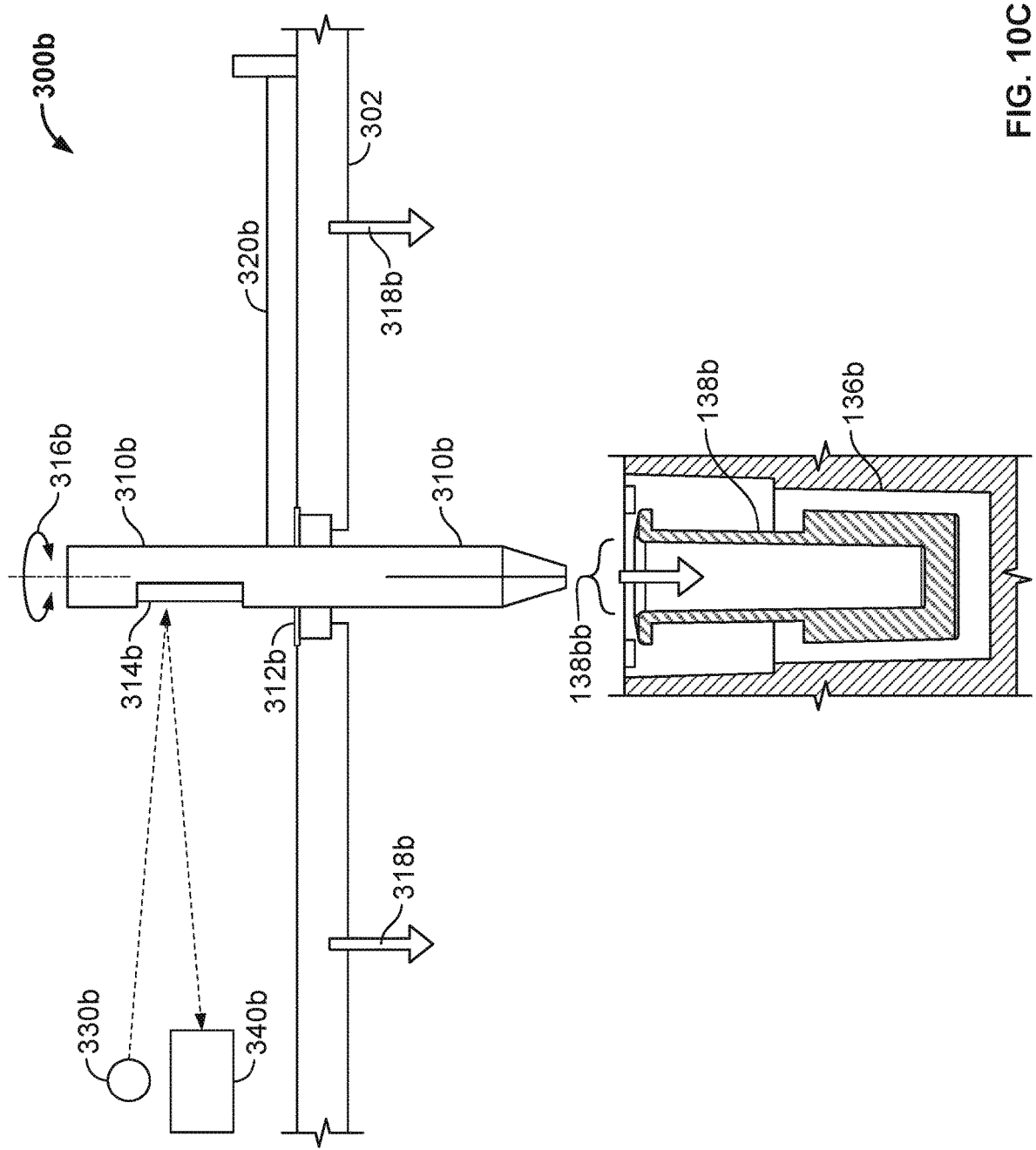

BLOOD TESTING SYSTEM AND METHOD

CLAIM OF PRIORITY

This application is a divisional of and claims to U.S. patent application Ser. No. 14/500,248, filed on Sep. 29, 2014, the entire contents of which are hereby incorporated by reference.

TECHNICAL FIELD

This document relates to systems and method for testing characteristics of a blood sample, such as an automated thromboelastometry system for point-of-care whole blood coagulation analysis.

BACKGROUND

Hemostasis is the human body's response to blood vessel injury and bleeding. Hemostasis involves a coordinated effort between platelets and numerous blood clotting proteins (or clotting factors), resulting in the formation of a blood clot and the subsequent stoppage of bleeding.

Various methods have been introduced to assess the potential of blood to form an adequate clot and to determine the blood clot's stability. Common laboratory tests such as thrombocyte counts or the determination of fibrin concentration provide information on whether the tested component is available in sufficient amount, but some of those tests might not answer the question of whether the tested component works properly under physiological conditions. Other laboratory tests work on blood plasma, which may impose additional preparation steps and additional time beyond what is preferred, for example, in the point-of-care context (e.g., in a surgical theater during a surgical operation).

Another group of tests to assess the potential of blood to form an adequate clot is known as "viscoelastic methods." In at least some viscoelastic methods, the blood clot firmness (or other parameters dependent thereon) is determined over a period of time, for example, from the formation of the first fibrin fibers until the dissolution of the blood clot by fibrinolysis. Blood clot firmness is a functional parameter which contributes to hemostasis in vivo, as a clot must resist blood pressure and shear stress at the site of vascular injury or incision. In many cases, clot firmness may result from multiple interlinked processes including coagulation activation, thrombin formation, fibrin formation and polymerization, platelet activation, and fibrin-platelet interaction.

To isolate and test particular functions of thrombocytes, fibrinogen, and other factors in a blood sample, reagent compounds can be mixed with the blood sample to activate or inhibit certain components in the blood sample. In some commercially available point-of-care blood testing systems, liquid reagents are injected into a disposable plastic cup containing a blood sample, and the cup is then engaged by the control console of the blood testing system to evaluate characteristics of the coagulation/clotting of the blood sample. As part of the test process, the system requires manual intervention by the operator for each of the assays, for example, when pipettes are used by an operator for the dispensing and measuring of the reagents, blood, and mixed samples.

SUMMARY

Some embodiments of a system for testing characteristics of a blood sample (which, as used herein, should be understood to include blood or derivatives of blood such as plasma) can include a cartridge configured to mate with a control console and receive a blood sample for a point-of-care whole blood coagulation analysis. In particular circumstances, the cartridge is configured to interact with the control console so as to perform a number of automated transport and testing operations on portions of the blood sample so as to provide reliable and prompt results indicative of a patient's blood characteristics at the point-of-care (e.g., while the patient is in a surgical room undergoing surgery). For example, the system can serve as an automated thromboelastometry system for providing detailed and prompt results of blood coagulation characteristics in response to receiving a cartridge (and blood sample at the cartridge) and an indication from an operator to begin the automated testing process.

In some embodiments, the thromboelastometry system includes a reusable analyzer console and one or more single-use cartridge components configured to mate with the console. In one example, to operate the thromboelastometry system, a user inserts the cartridge into the analyzer console and, when prompted by the analyzer console, inserts a blood collection tube (containing a whole blood sample) into a receiver portion of the cartridge. The user is then prompted a user interface of the analyzer console to initiate a number of automated blood transfer and testing operations. Thereafter, the analyzer console automatically performs (without requiring further user interaction with the cartridge or the blood sample) the testing and displays the results on a graphical display using qualitative graphical representations and quantitative parameters. In this particular example, no manual pipetting, mixing, or handling of reagents by the user is needed. In some embodiments, four or more assays are automatically performed on the blood sample using a single cartridge device. Such assays provide information on the whole kinetics of hemostasis, such as clotting time, clot formation, clot stability, and lysis; moreover, such information can be promptly output from a user interface of the system to provide reliable and prompt results indicative of a patient's blood characteristics at the point-of-care (e.g., while the patient is in a surgical room undergoing surgery).

Particular embodiments described herein include a cartridge for use with a blood testing console. The cartridge may include a blood sample receiver configured to receive a blood sample to be tested. The cartridge may also include one or more blood processing and testing paths. Each blood processing and testing path can receive a portion of the blood sample and may include a blood sample volume measurement chamber, a mixing chamber, and a viscoelastic blood testing chamber. The blood sample volume measurement chamber may be in fluid communication with the blood sample receiver, and the blood sample volume measurement chamber may a selected internal volume to contain a predefined volume of blood sample from the blood sample container. The mixing chamber may be in fluid communication with the blood sample volume measurement chamber and with a reagent, and the mixing chamber may be configured to receive blood sample from the blood sample volume measurement chamber and mix the received blood with the reagent. The viscoelastic blood testing chamber may be configured to receive mixed blood and reagent from the mixing chamber for a viscoelastic test to be performed on the mixed blood and reagent while the mixed blood and reagent resides in the testing chamber.

In some embodiments described herein, a cartridge device may include a blood sample receiver, and a plurality of blood sample pathways in selective fluid communication with the blood sample receiver. Each blood sample pathway may include: a blood measurement chamber to receive a predetermined amount of a blood sample via the blood sample receiver, a reagent mixing chamber for receiving and mixing the predetermined amount of the blood sample with one or more reagents, and a blood coagulation blood testing chamber for receiving from the reagent mixing chamber at least a portion of the blood sample with one or more reagents mixed therewith. Optionally, the blood coagulation blood testing chamber may have a movable probe therein for measuring blood coagulation characteristics.

Various embodiments described herein include a cartridge device for a measuring system for measuring viscoelastic characteristics of a blood sample. The cartridge may include a blood sample receiver; and at least one blood sample pathway in selective fluid communication with the blood sample receiver. The blood sample pathway may include: a blood measurement chamber configured to be filled with a predetermined amount of a blood sample via the blood sample receiver, a reagent mixing chamber for receiving the predetermined amount of the blood sample from the blood measurement chamber and for and mixing the predetermined amount of the blood sample with one or more reagents, and a blood coagulation blood testing chamber for receiving from the reagent mixing chamber at least a portion of the blood sample with one or more reagents mixed therewith, and an overflow chamber in fluid communication with the blood sample pathway so as to collect excess blood from the blood measurement chamber beyond the predetermined amount the blood sample. Optionally, the blood coagulation blood testing chamber may have a movable probe therein for measuring blood coagulation characteristics.

Other embodiments described herein include a measuring system for measuring viscoelastic characteristics of a blood sample. The system may include a control unit housing viscoelastic measurement components. The control unit may define an exterior port. The system may also include at least one disposable cartridge comprising a blood sample input accessible along an exterior of the cartridge and a plurality of blood testing chambers positioned along an interior of the cartridge. Optionally, the control unit is configured to releasably mate with the disposable cartridge when inserted into the exterior port such that the blood sample input of the cartridge remains external to the control unit while the plurality of blood testing chambers are positioned within the control unit.

Some embodiments described herein include a method of using a system for measuring viscoelastic characteristics of a blood sample. The method may include inserting a disposable cartridge into a blood testing control console such that a blood sample input remains externally exposed. The method may also include attaching a blood sample reservoir to the blood sample input. The method may further include providing user input via a user interface of the blood testing control console so as to initiate an automated transport of blood in the blood sample reservoir to a plurality of blood testing chambers within the cartridge for measuring viscoelastic characteristics of the blood in each of the blood testing chambers.

In particular embodiments described herein, a cartridge device for a measuring system for measuring viscoelastic characteristics of a blood sample may include a blood sample receiver structure defining a cavity configured to releasably mate with a blood sample reservoir container. The cartridge device may also include a plurality of blood testing chambers spaced apart from the blood sample receiver structure and each having a movable probe therein for measuring blood coagulation characteristics. All of the blood testing chambers may be in selective fluid communication the blood sample receiver structure.

In some embodiments described herein, a cartridge device for a measuring system for measuring viscoelastic characteristics of a blood sample may include a plurality of blood testing chambers for measuring blood coagulation characteristics. Each of the blood testing chambers may be exposed to atmosphere and may have a blood input port positioned along a sidewall of the blood testing chamber. Optionally, each of the blood testing chambers is in fluid communication with an output port of a respective reagent mixing chamber that is defined in cartridge device at a height below the blood input port of the blood testing chamber.

In various embodiments described herein, a cartridge device for a measuring system for measuring viscoelastic characteristics of a blood sample may include a plurality of reagent mixing chambers for receiving and mixing a predetermined amount of a blood sample with one or more reagent beads. The cartridge device may also include a plurality of retaining elements extending into the reagent mixing chamber so as to maintain a predetermined vertical position of each of the reagent mixing beads within the mixing chamber. The retaining elements of at least one of the reagent mixing chambers may engage multiple reagent mixing beads to maintain the multiple reagent mixing beads spaced apart from one another.

In particular embodiments described herein, a cartridge device for a measuring system for measuring viscoelastic characteristics of a blood sample may include a plurality of reagent mixing chambers for receiving and mixing a predetermined amount of a blood sample with one or more reagent beads. The cartridge device may also include a movable mixing element retained with the reagent mixing chamber. The movable mixing element may comprise a material that is inert relative to the blood sample. The cartridge device may further include a plurality of retaining elements extending into the reagent mixing chamber so as to maintain the reagent mixing beads in positions that are spaced apart from the movable mixing element.

Some embodiments described herein may include a method for measuring coagulation characteristics of a blood sample. The method may include detecting a blood testing cartridge being inserted into a receiver portion of a blood testing control unit. The method may also include prompting a user for input via a user interface of the blood testing control unit to initiate automated transport of blood in the blood sample reservoir to one or more blood testing chambers within the cartridge for measuring viscoelastic characteristics of the blood in each of the blood testing chambers. The method may further include automatically transporting to each of the one or more blood testing chambers within the cartridge a predetermined amount of a blood sample from a blood sample receiver of the blood testing cartridge. Optionally, the method may also include moving a probe in each respective blood testing chamber of the cartridge for measuring blood coagulation characteristics. The method may further include displaying via the user interface measurement results of the blood coagulation characteristics.

Other embodiments described herein include a control console for measuring coagulation characteristics of a blood sample. The control console may include a control unit housing that houses at least one interface element configured to releasably receive a disposable cartridge (which, optionally, may have multiple blood testing chambers therein, and multiple measurement components configured to measure coagulation characteristics of the blood sample within the multiple blood testing chambers of the disposable cartridge). The control console may also include one or more heating elements positioned proximate to the interface element and configured to heat the cartridge to a predetermined, test-related temperature (e.g., 37 degrees C. in some embodiments). The control console may further include one or more temperature sensors positioned proximate to the interface element. The control unit may be configured to transport blood to the multiple blood testing chambers of the disposable cartridge after the temperature sensors indicate the multiple blood testing chambers of the disposable cartridge have reached a predefined temperature.

Some or all of the embodiments described herein may provide one or more of the following advantages. First, some embodiments of the thromboelastometry system are configured to be automated so that user interactions with the system are minimized. As a result, human resources—especially in a point-of-care context like a surgical theater—can be utilized with greater efficiency. The reduction of user interactions can also reduce the chances for manual operator errors, such as measuring inaccuracies, reagent mixing errors, and the like. Accordingly, more accurate thromboelastometry results may be attained in some circumstances.

Second, in some embodiments, the cartridge component includes multiple fluid channels that are each individually controllable so that multiple different assays can be performed from a single supply of a blood sample. For example, each fluid channel includes a dedicated valve and a dedicated vent that are controllable by the analyzer console so that the blood flow and testing of each fluid channel is individually controllable. This feature enables the thromboelastometry system to automatically perform sophisticated assay processes.

Third, in some embodiments, the analyzer console can be configured to perform a number of quality-control operations/confirmations so as to ensure the blood test results are not compromised. For example, the analyzer console can be configured to verify the blood testing cartridge is heated to a target temperature (e.g., about 37° C.) prior to the blood sample being distributed to testing chambers of the cartridge. Because temperature of the blood sample can affect the coagulation characteristics in some circumstances, the accuracy of the thromboelastometry results may be enhanced as a result of such temperature-control operations/confirmations.

Forth, in particular embodiments of the cartridge device, the geometry of the blood flow paths through the fluid channels of the cartridge are configured to reduce the potential for disturbing the blood (e.g., causing bubble formation, etc.), and/or damaging the blood, in a manner that may negatively impact the accuracy of the blood test results.

Fifth, in some embodiments, the blood testing cartridge (and, optionally, the blood collection reservoir) can be equipped with one or more computer-readable components so as to promptly transfer relevant information of the analyzer console for each blood sample testing cycle. For example, each cartridge can be labeled with a barcode, near-field communication tag, and RFID tag, or the like that includes information such as, but not limited to, the types of assays to be performed by the cartridge, the type of reagents container within the cartridge, manufacturer information, an expiration date, or the like. In such embodiments, the analyzer console can include a barcode reader (or a reader for a near-field communication tag, a RFID tag, or the like) that scans the barcode upon insertion of the cartridge into the analyzer console. The analyzer console automatically performs appropriate actions in response to the data read from the barcode. In another example, each blood collection reservoir that is to be used with a corresponding cartridge can be labeled with a barcode, near-field communication tag, and RFID tag, or the like that includes information such as, but not limited to, patient information, clinician information, calibration information, or the like (e.g., which is readable by a corresponding reader device of the analyzer console).

Sixth, each fluid pathway of the cartridge can include a mixing chamber with one or more reagents and a mixing element located therein. In some embodiments, the reagents comprise dissolvable reagent beads. The mixing chambers of the cartridge can be configured to separate the one or more reagent beads from each other and to inhibit the mixing element from direct contact with the reagent beads. Further advantages associated with the thromboelastometry systems provided herein are also envisioned, as will be evident from the following disclosure.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A, 1B, 2, and 3 are perspective illustrations depicting the components and use of an example thromboelastometry system, in accordance with some embodiments.

FIG. 10C is a schematic diagram depicting the partial cross-sectional view of the cartridge component of FIG. 10B in conjunction with associated components of an analyzer console of the thromboelastometry system of FIGS. 1A, 1B, 2, and 3.

DETAILED DESCRIPTION OF ILLUSTRATIVE EMBODIMENTS

Figure 3:
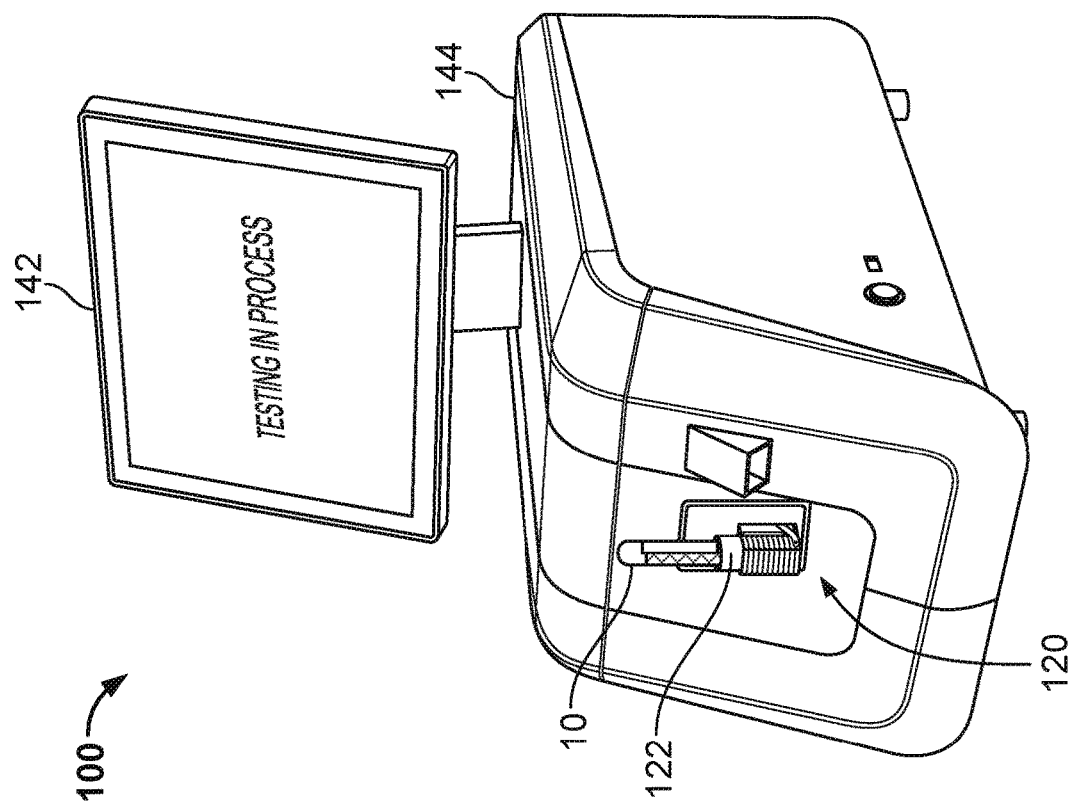

Referring to FIGS. 1A-3, some embodiments of a blood testing system 100 include an analyzer console 140 and one or more cartridges 120 configured to releasably mate with analyzer console 140. In this embodiment, the blood testing system 100 is a thromboelastometry system that is configured to determine a number of blood coagulation characteristics of a blood sample input into the cartridge 120. For example, the cartridge 120 can be configured as a single-use cartridge that includes a blood sample receiver 122 for mating with a blood sample reservoir 10 (e.g., a vacutainer sample tube supplied by Becton, Dickinson & Company of Franklin Lakes, N.J., or another blood reservoir structure). In some cases, an adapter may be used to couple other types of blood sample reservoirs 10 with the cartridge 120 (e.g., tubing may be used through which blood can be injected into the cartridge 120, and the like). The thromboelastometry system 10 can be used as a whole blood coagulation analysis system that is particularly advantageous at a point-of-care site (e.g., in a surgical theater while a patient is undergoing or preparing for surgery, or the like). Additionally, thromboelastometry system 100 can be used as a whole blood coagulation analysis system in a laboratory setting.

The analyzer console 140 includes a user interface 142 (with touchscreen display in this embodiment) and a main chassis 144. The user interface display 142 can be configured to output one or more graphical results 143 from the blood testing assays performed via the cartridge 120 and console 140 (e.g., one or more plots, such as those sometimes refer to as a TEMogram, numeric data or measurements, or a combination thereof). In some embodiments, the user interface display 142 is rigidly attached to the analyzer console 140. In particular embodiments, the user interface display 142 is pivotable and/or is otherwise positionally adjustable in relation to the main chassis 144. A main power switch 148 can be located at a convenient but protected location on the main chassis 144.

In the depicted embodiment, the touchscreen display 142 is configured to receive user input and to display output information to the user. For example, the user can enter information to the thromboelastometry system 100 by making selections of various soft-buttons that may be displayed on the touchscreen display 142 at times during the beginning, middle, and end of the testing process. In some embodiments, other selections such as, but not limited to, soft keyboard entries can be provided via touchscreen display 142. In some embodiments, data entry can be performed additionally or alternatively by voice entry. In other embodiments, the user interface may include other peripheral devices can be included (e.g., a mouse, a keyboard, an additional display device, and the like) as part of the thromboelastometry system 100. In some embodiments, a computer data network (e.g., intranet, interne, LAN, etc.) may be used to allow for remote devices to receive and/or input information from the system 100. For example, in some embodiments one or more remote displays can be utilized via network connections. In the depicted embodiment, the thromboelastometry system 100 also includes an external barcode reader 146. The external barcode reader 146 can facilitate convenient one-dimensional or two-dimensional barcode entry of data such as, but not limited to, blood sample data, user identification, patient identification, normal values, and the like. Alternatively or additionally, the thromboelastometry system 100 can be equipped with a reader configured to read near-field communication tags, RFID tags, or the like.

In the depicted embodiment, the main chassis 144 houses various internal sub-systems (as described further below), includes various electronic connection receptacles (not shown), and includes a cartridge port 150. The various electronic connection receptacles can include network and device connectors such as, but not limited to, one or more USB ports, Ethernet ports (e.g., RJ45), VGA connectors, Sub-D9 connectors (RS232), and the like. Such connection receptacles can be located on the rear of the main chassis 144, or at other convenient locations on the main chassis 144. For example, in some embodiments one or more USB ports may be located on or near the front of the main chassis 144. A USB port, so located, may provide user convenience for recording data onto a memory stick, for example. In some embodiments, the thromboelastometry system 100 is configured to operate using wireless communication modalities such as, but not limited to, Wi-Fi, Bluetooth, NFC, RF, IR, and the like.

Still referring to FIGS. 1A-3, the cartridge port 150 can be located at a readily accessible location on the main chassis 144. In the depicted embodiment, the cartridge port 150 is located on the front of the main chassis 144 so that it is conveniently accessible by a user in a point-of-care site. The cartridge port 150 defines an opening and internal space that is shaped complementarily to the outer dimensions of the single-use cartridge 120. To insert the single-use cartridge 120 into the cartridge port 150, the user can grasp the end of the cartridge 120 that includes the blood sample receiver 122 and slidingly insert the opposite end (leading end) into the cartridge port 150. The sliding insertion can continue until a hard-stop is reached that defines the fully inserted position. In the fully inserted position, a trailing end portion (including the blood sample receiver 122 in this embodiment) of the single-use cartridge 120 remains exterior to the main chassis 144. The portion of the cartridge 120 that is received into the cartridge port 150 can include outer surface features (such as a tapered angle a rear end portion shown in FIG. 1B) that mate with at least one internal interface element inside the console 140 to ensure correct positioning of the cartridge 120. As such, at least the blood sample receiver 122 remains exterior to the main chassis 144 throughout the duration of the blood sample testing. In this configuration, the blood sample receiver 122 serves as a blood sample well that is accessible so that the blood sample reservoir 10 can be inserted into the receiver 122 while the single-use cartridge 120 is mated with the console 140 in the fully inserted position. In some embodiments, the cartridge port 150 and the main chassis 144 are configured so that the exposed portion of the cartridge 120 is protected from inadvertent contact. As described further below, an internal sensor (e.g., a microswitch, an optical sensor, etc.) can detect when the single-use cartridge 120 has been fully inserted into the main chassis 144.

When the analyzer console 140 has detected that the cartridge 120 has been fully inserted, in some embodiments the analyzer console 140 initiates one or more of the following actions. An internal cartridge clamping mechanism that includes positioning pins can be activated to accurately position and releasably retain the single-use cartridge 120 in the fully inserted position. One or more cartridge heating elements can be nalactivated to warm the cartridge 120. The temperature of the cartridge 120 can be monitored. A barcode on the leading end of the cartridge 120 can be read and the barcode data can be stored in memory of the analyzer console 140. One or more blood detection sensors can inspect the cartridge 120 for the presence of blood (which should not be present at this time). The rotational thromboelastometry measuring sub-system can be engaged with the cartridge 120 and, optionally, rotation of the rotary thromboelastometry measuring sub-system can begin (without the presence of blood). The cartridge 120 can be leak tested using vacuum or air pressure delivered by the analyzer console 140. For example, a pressure/vacuum decay test can be performed. In some embodiments, other actions can be additionally or alternatively activated when the analyzer console 140 has detected that the cartridge 120 has been fully inserted. After the completion of such actions, in some embodiments an indication of the results of the actions may be displayed on the touchscreen display 142 (e.g., pass or fail). If the analyzer console 140 determines that the actions were completed successfully, a prompt can be provided on the touchscreen display 142 that informs the user that the thromboelastometry system 100 is ready to receive the blood sample reservoir 10.

Briefly, in some embodiments a user can operate the depicted thromboelastometry system 100 embodiment as follows. First, the user can insert the single-use cartridge 120 into the cartridge port 150 so that the cartridge 120 is placed into the fully inserted position. Completion of that step will automatically initiate a series of operations by the thromboelastometry system 100 as described below. Upon successful completion of such operations, a notification that the blood collection tube 10 can be inserted into the sample well 122 will be displayed on the touchscreen display 142. After the user has mated the blood collection tube 10 into the sample well 122, the user initiates testing by pressing a "start" button (or the like) on the touchscreen display 142. At least the blood measuring, reagent mixing, and thromboelastometry testing is performed automatically by the system 100 thereafter (e.g., without requiring manual intervention from the user in this embodiment). When the testing is completed, the results are displayed on the touchscreen display 142 in the form of qualitative graphical representations and quantitative parameters (e.g., as depicted in FIG. 1A). Also, when the testing is completed, the cartridge 120 can be removed from the console 140 and discarded (e.g., the cartridge 120 in such embodiments is not reusable in that the reagent beads (described below) are no longer present in the cartridge and the measurement chambers contain the clotted blood sample portions).

Alternately, in some embodiments the blood collection tube 10 can be inserted into the sample well 122 of the cartridge 120 prior to insertion of the cartridge 120 into the cartridge port 150. In such circumstances, the blood from the collection tube 10 may not advance to the measurement chambers (described below) of the blood cartridge 120 until after the console 140 acts upon the cartridge 120 (again, as described below). With the blood collection tube 10 being pre-coupled with the cartridge 120, the combination of the blood collection tube 10 and the cartridge 120 can then be inserted into the cartridge port 150.

Figure 4:
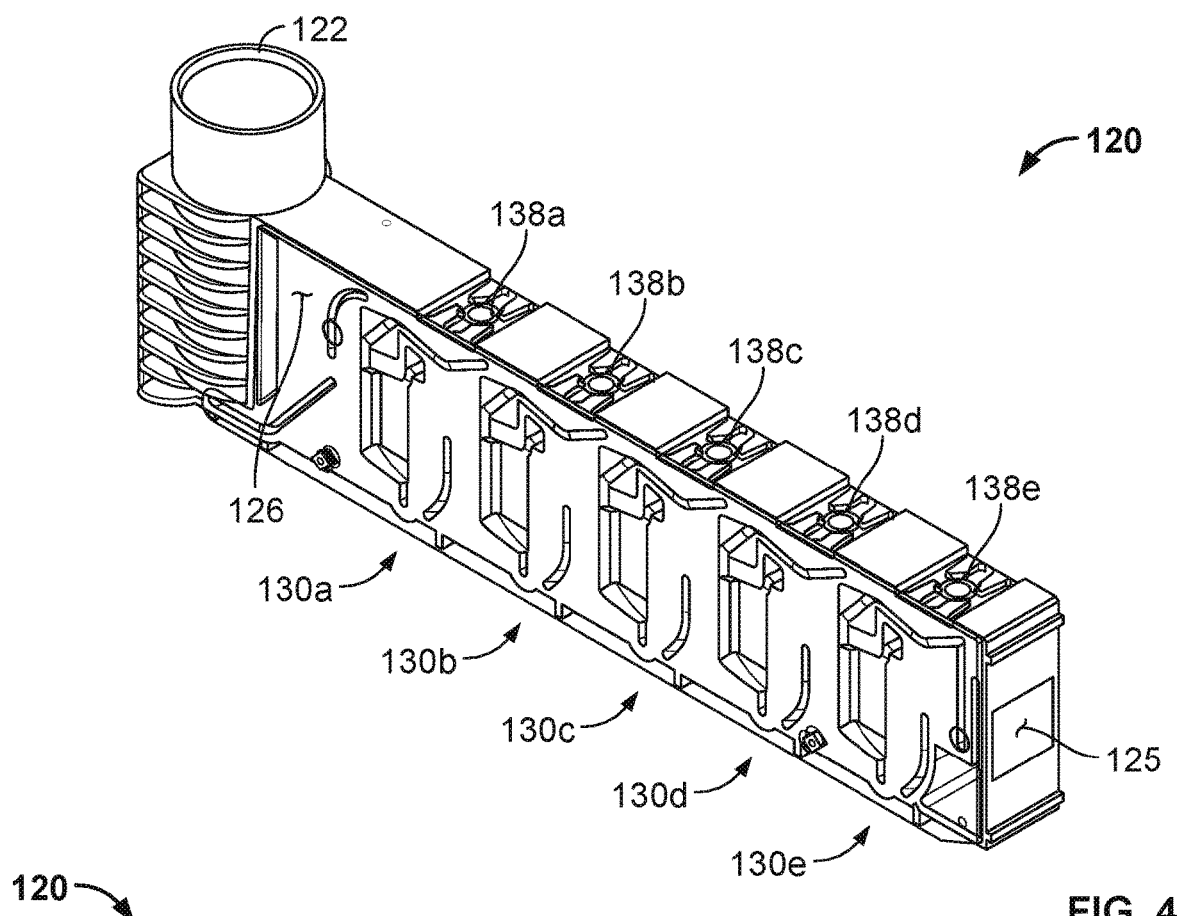
FIG. 4 is a perspective view of the example cartridge component of the thromboelastometry system of FIGS. 1A, 1B, 2, and 3.
Figure 5:
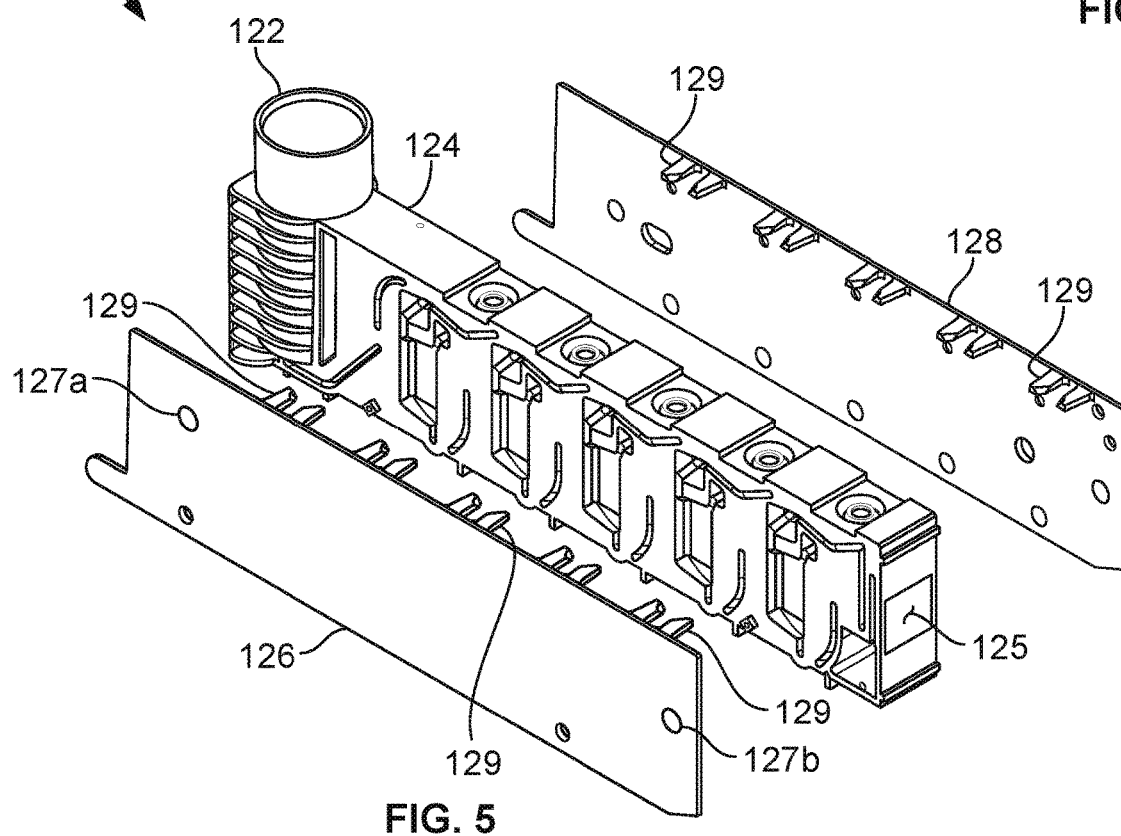
FIG. 5 is an exploded view of the cartridge component of FIG. 4.

Referring now to FIGS. 4 and 5, the depicted embodiment of the single-use cartridge 120 includes a main body 124, a right cover 126, a left cover 128, and five pins 138a, 138b, 138c, 138d, and 138e. The right cover 126 is affixed to right side of the main body 124, and the left cover 128 is affixed to the left side of the main body 124. As such, the right and left covers 126 and 128 enclose cavities and flow channels of the main body 124 to define blood flow paths as described further below. The aforementioned sample well 122 is part of the main body 124. However, other constructions of the single use cartridge 120 are also envisioned.

In some embodiments, the main body 124, right cover 126, left cover 128, and the pins 138a, 138b, 138c, 138d, and 138e are made by injection molding. After molding, the right and left covers 126 and 128 can be affixed to the main body 124 using various techniques including, but not limited to, ultrasonic welding, laser welding, solvent bonding, adhesive bonding, UV curable adhesive bonding, and the like. Various polymeric materials can be used to construct the main body 124, right cover 126, left cover 128, and pins 138a-e. For example, such polymeric materials can include, but are not limited to acrylic, polycarbonate, polyvinyl chloride (PVC), polyethylene, polypropylene, polymethyl methacrylate, polystyrene, acrylonitrile butadiene styrene (ABS), polyethylene, polypropylene, and the like, and combinations thereof. In some embodiments, the materials are used to construct the main body 124, right cover 126, left cover 128, and pins 138a-e comprise an acrylic-based multi-polymer compound. In some embodiments, the main body 124, right cover 126, and left cover 128 are essentially transparent, or at least translucent. Therefore, in FIG. 4, features of the main body 124 are visible even though the right cover 126 is attached thereto.

In some embodiments, overmolding, such as by insert molding or multi-shot molding techniques, may be used to construct some aspects of the main body 124, right cover 126, and/or left cover 128. For example, elastomeric valve elements (as described further below) may be overmolded in the left cover 128. Further, in some embodiments secondary operations may be performed to the cartridge 120. For example, one or more needles 123a-b (refer to FIG. 6) for piercing a blood collection tube may be installed within the sample well 122 using secondary operations.

The single-use cartridge 120 also includes the five pins 138a, 138b, 138c, 138d, and 138e. The pins 138a-e are individual component parts (e.g., refer to FIG. 10B) that are retained within openings of the main body 124 (e.g., within testing chambers 136a-e (sometimes referred to as "cups") as described further below in connection with FIGS. 8A-10B). Tabs 129, located on the right and left covers 126 and 128, mechanically retain the pins 138a-e in the main body 124. However, the pins 138a-e are free to move within the confines of the main body 124 to a limited extent. For example, the pins 139a-e are free to rotate uninhibitedly within the main body 124 and to translate vertically by few millimeters. This configuration of the pins 138a-e in relation to the other components of the cartridge 120 can be created as follows. Prior to affixing the right and left covers 126 and 128 to the main body 124, the pins 138a-e can be placed within their respective locations in the main body 124 as shown in FIG. 5. With the pins 138a-e positioned in the main body 124, the right and left covers 126 and 128 can then be affixed to the main body 124. In another example, the right and left covers 126 and 128 are affixed to the main body 124 and thereafter the pins 138a-e are pushed into the main body 122 past the tabs 129. The tabs 129 of the right and left covers 126 and 128 will block the pins 138a-e from falling out of the main body 122, even if the cartridge 120 is turned upside down.

Figure 2:
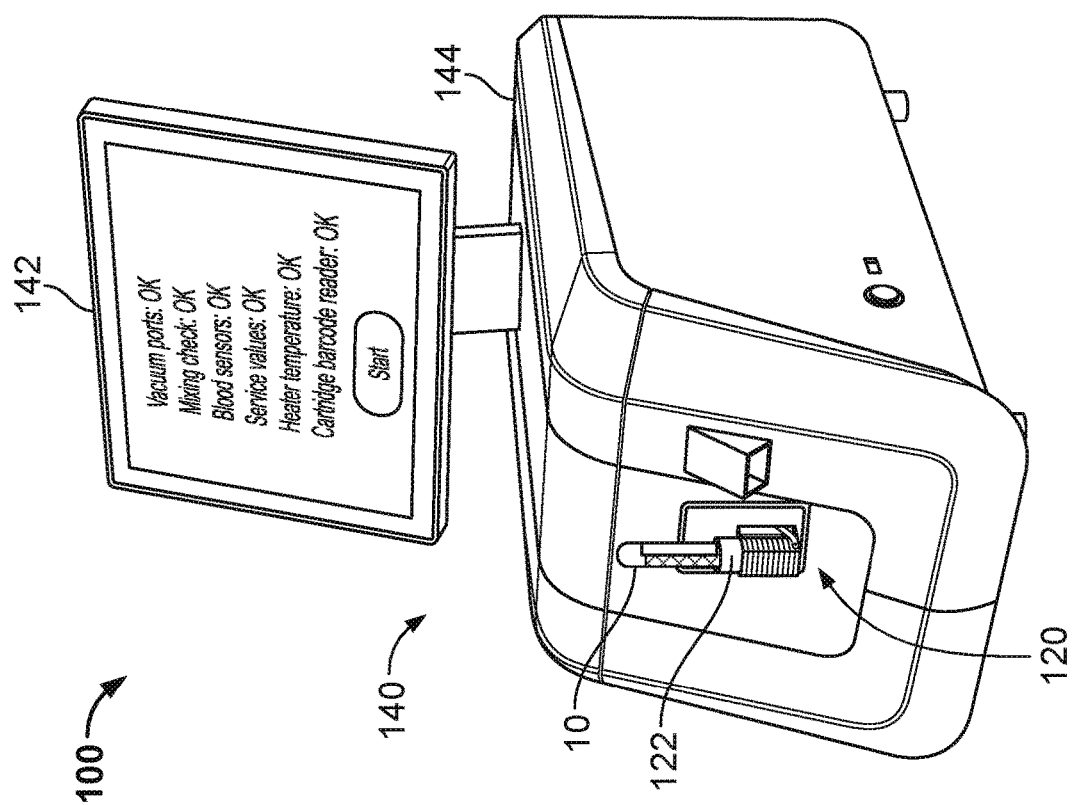

In some embodiments, the main body 124 includes a barcode location 125. The barcode location 125 can be used as a location at which to adhere a barcode label, or to print a barcode. The barcode location 125 is on the leading end of the cartridge 120 (in relation to the direction of insertion of the cartridge 120 into the analyzer console 140 as shown in FIGS. 1-3).

In the depicted embodiment, the right cover 126 includes blood detection locations 127a and 127b. As will be described further below, the blood detection locations 127a and 127b are designated locations on the cartridge 120 at which sensors of the analyzer console 140 interface with the cartridge 120. The sensors inspect for the presence of blood within the cartridge 120 at the blood detection locations 127a and 127b. In some embodiments, the sensors are optical sensors (e.g., infrared sensors) and the blood detection locations 127a and 127b are polished areas that have enhanced transparency and optical clarity. As such, the right cover 126 is configured so that the optical sensors of the analyzer console 140 can readily detect the presence or absence of blood at the blood detection locations 127a and 127b.

Figure 6:
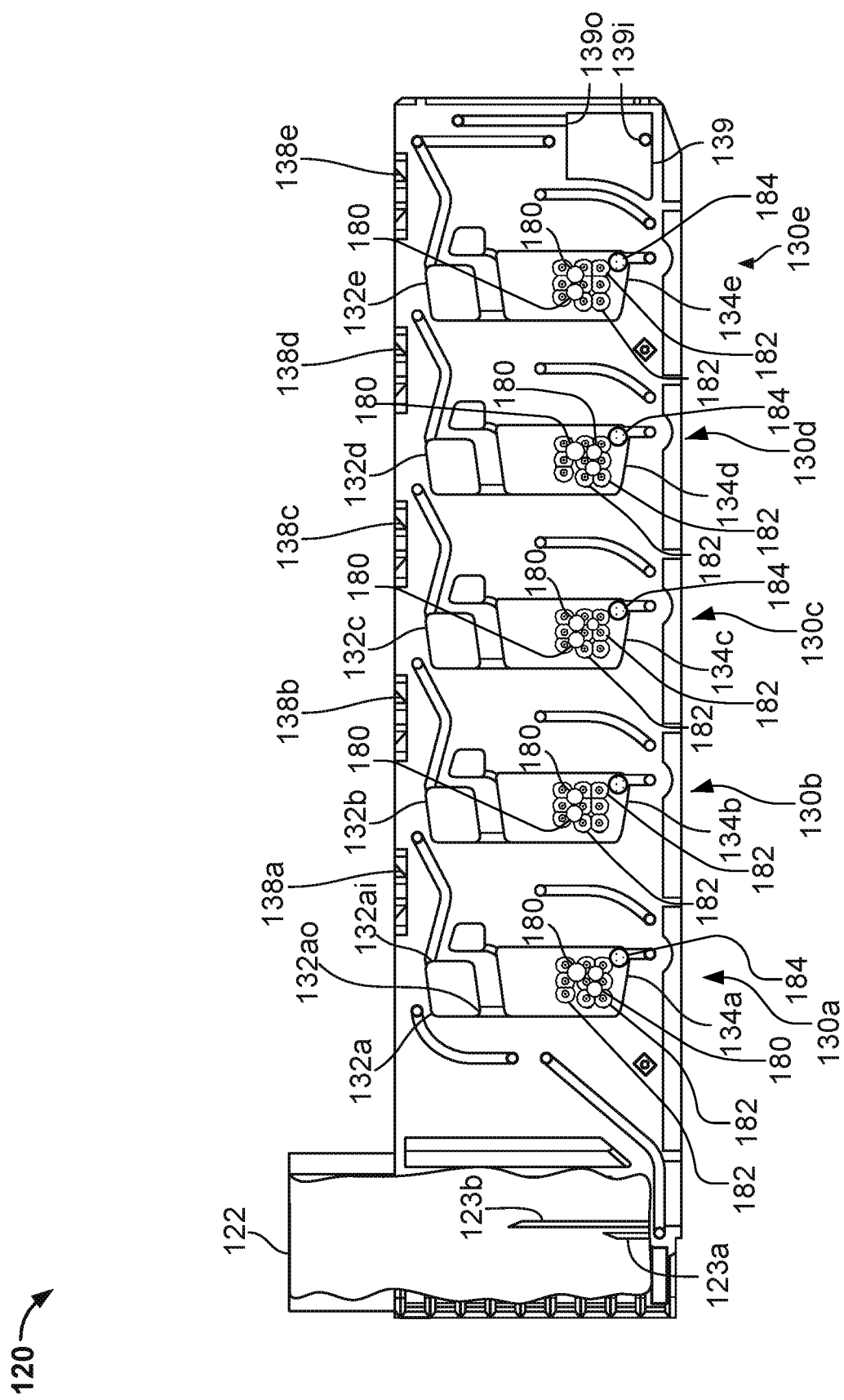
FIG. 6 is a right side partial cutaway view of the cartridge component of FIG. 4.

Referring now to FIGS. 4, 5, and 6, broadly speaking the single-use cartridge 120 is configured to: (i) extract blood from a blood collection tube (e.g., blood collection tube 10 of FIGS. 1-3) and measure a precise volume of the extracted blood, (ii) mix a precise amount of blood with reagents, and (iii) deliver the mixture to multiple cup and pin locations of the cartridge 120 where thromboelastometry testing is performed. These steps will be described in more detail below.

In the depicted embodiment, the single-use cartridge 120 includes five individual blood flow channels 130a, 130b, 130c, 130d, and 130e. Alternately, in some embodiments the cartridge includes a single individual blood flow channel, or two individual blood flow channels, or three individual blood flow channels, or four individual blood flow channels, or six individual blood flow channels, or more than six individual blood flow channels. Each channel 130a-e includes: (i) a measuring chamber, (ii) a mixing chamber containing reagent(s) and a mixing element, and (iii) a blood coagulation testing chamber (e.g., in this embodiment a cup having a movable probe/pin therein). For example, the channel 130a includes a measuring chamber 132a, a mixing chamber 134a, and a testing chamber 136a (refer to the example of the testing chamber being depicted in detail in FIGS. 10A-B). Similarly, the channel 130b includes a measuring chamber 132b, a mixing chamber 134b, and a testing chamber 136b; the channel 130c includes a measuring chamber 132c, a mixing chamber 134c, and a testing chamber 136a; the channel 130d includes a measuring chamber 132d, a mixing chamber 134d, and a testing chamber 136d; and the channel 130e includes a measuring chamber 132e, a mixing chamber 134e, and a testing chamber 136e.

In some embodiments, the sample well 122 includes needles 123a and 123b that are configured to pierce a septum of a blood collection tube when the blood collection tube is inserted into the sample well 122. The needle 123a is in fluid communication with the channels 130a-e, while the needle 123b is a vent that facilitates the ready flow of blood out of the blood collection tube.

In the depicted embodiment, the fluid flow paths from the needle 123a to the channels 130a-e are as follows. The needle 123a is confluent with the measuring chamber 132a. The measuring chamber 132a is confluent with the measuring chamber 132b. The measuring chamber 132b is confluent with the measuring chamber 132c. The measuring chamber 132c is confluent with the measuring chamber 132d. The measuring chamber 132d is confluent with the measuring chamber 132e. Accordingly, blood can flow out of the blood collection tube through the needle 123a to the measuring chamber 132a; from the measuring chamber 132a to the measuring chamber 132b; from the measuring chamber 132b to the measuring chamber 132c; from the measuring chamber 132c to the measuring chamber 132d; and from the measuring chamber 132d to the measuring chamber 132e. The measuring chambers 132a-e may also be referred to as metering chambers 132a-e. Each measuring chamber 132a-e has an inlet port and an outlet port. The inlet ports are located near the top of the measuring chambers 132a-e.

For example, measuring chamber inlet port 132ai is located near the top of the measuring chamber 132a. This configuration can be advantageous if the blood contains gaseous bubbles, because such gas may be allowed to escape from the blood as the blood enters the measuring chambers 132a-e. In addition, this configuration may advantageously minimize fluid flow turbulence as the blood flows into the measuring chambers 132a-e, thereby reducing the likelihood of damaging the blood cells.

The outlet ports are located at the bottom of the measuring chambers. For example, measuring chamber outlet port 132ao is located at the bottom of the measuring chamber 132a. This configuration can help facilitate the complete filling of the measuring chambers 132a-e with blood. As such, a precise volume of blood is contained within the measuring chambers 132a-e.

From the foregoing description of the fluid flow paths from the needle 123a to the measuring chambers 132a-e, and from the foregoing description of the location of the measuring chamber outlet ports, it should be understood that the measuring chambers 132a-e will be filled with blood in a sequential manner. That is, first measuring chamber 132a will be filled with blood; then blood from measuring chamber 132a will flow to measuring chamber 132b; then measuring chamber 132b will be filled with blood; then blood from measuring chamber 132b will flow to measuring chamber 132c; then measuring chamber 132c will be filled with blood; then blood from measuring chamber 132c will flow to measuring chamber 132d; then measuring chamber 132d will be filled with blood; then blood from measuring chamber 132d will flow to measuring chamber 132e; then measuring chamber 132e will be filled with blood.

After the measuring chamber 132e is filled with blood, then blood from measuring chamber 132e will flow to an overflow chamber 139. The blood flowing from measuring chamber 132e will enter the overflow chamber 139 at an overflow chamber inlet port 139i. As will be described further below, the overflow chamber 139 serves to ensure that the measuring chamber 132e becomes completely full, while preventing blood from exiting the cartridge 120 and flowing into a vacuum source that is used to draw the blood into the measuring chambers 132a-e as described above. The vacuum source is fluidly connected to the overflow chamber 139 at an overflow chamber outlet port 139o. When a negative pressure (with respect to ambient pressure) from the vacuum source is applied at the overflow chamber outlet port 139o, blood from a blood collection tube that is coupled with needle 123a will flow into the cartridge 120 to fill all the measuring chambers 132a-e. Some blood will also exit the measuring chamber 132e and flow towards the overflow chamber 139.

As described further below, various valves and vents are interspersed within the fluid flow paths so that the blood flow can be controlled by the analyzer console according to predefined schemes. In addition, the aforementioned blood detection locations 127a and 127b (refer to FIG. 5) are designated locations on the cartridge 120 at which sensors of the analyzer console 140 interface with the cartridge 120. The sensors inspect for the presence of blood within the cartridge 120 at the blood detection locations 127a and 127b. The blood sensor location 127a is on the fluid flow path between the needle 123a and the measuring chamber 132a. When the analyzer console detects blood at blood sensor location 127a, the analyzer console 140 determines that blood has been drawn into the cartridge 120. The blood sensor location 127b is on the fluid flow path between the measuring chamber 132e and the overflow chamber 139. When the analyzer console detects blood at blood sensor location 127b, the analyzer console 140 determines that blood has been drawn into and filled all the measuring chambers 132a-e. Further, when the analyzer console 140 detects blood at blood sensor location 127b, the analyzer console 140 may cease further application of negative pressure at the overflow chamber outlet port 139o. In other words, by detecting blood at blood sensor location 127b, the analyzer console 140 can determine that the application of vacuum has successfully filled all the measuring chambers 132a-e and that the application of vacuum can be ceased. Optionally, the cartridge 120 may be equipped with a blood temperature sensor at or near the location of blood sensor location 127b so as to verify the blood sample is at a predetermined target temperature.

As described above, each individual channel 130a-e has a measuring chamber 132a-e respectively. In some embodiments, the fluid flow paths within the individual channels 130a-e are as follows. From the measuring chambers 132a-e, the blood can flow to the respective mixing chambers 134a-e. For example, the blood from measuring chamber 132a can flow to the mixing chamber 134a. Similarly, the blood from measuring chamber 132b can flow to the mixing chamber 134b; the blood from measuring chamber 132c can flow to the mixing chamber 134c; the blood from measuring chamber 132d can flow to the mixing chamber 134d; and the blood from measuring chamber 132e can flow to the mixing chamber 134e. From the mixing chambers 132a-e (after completion of the mixing), the blood can flow to the respective testing chambers 136a-e (having a corresponding probe/pin 138a-e therein, refer below to FIGS. 10A-b). For example, the blood from mixing chamber 134a can flow to the testing chamber 136a. Similarly, the blood from mixing chamber 134b can flow to the testing chamber 136b; the blood from mixing chamber 134c can flow to the testing chamber 136c; the blood from mixing chamber 134d can flow to the testing chamber 136d; and the blood from mixing chamber 134e can flow to the testing chamber 136e. Various valves and vents that are controllable by the analyzer console 140 are interspersed within the fluid flow paths of the individual channels 130a-e. Using such valves and vents, the blood flow within the individual channels 130a-e can be controlled by the analyzer console 140 in accordance with predefined schemes.

Figure 7:
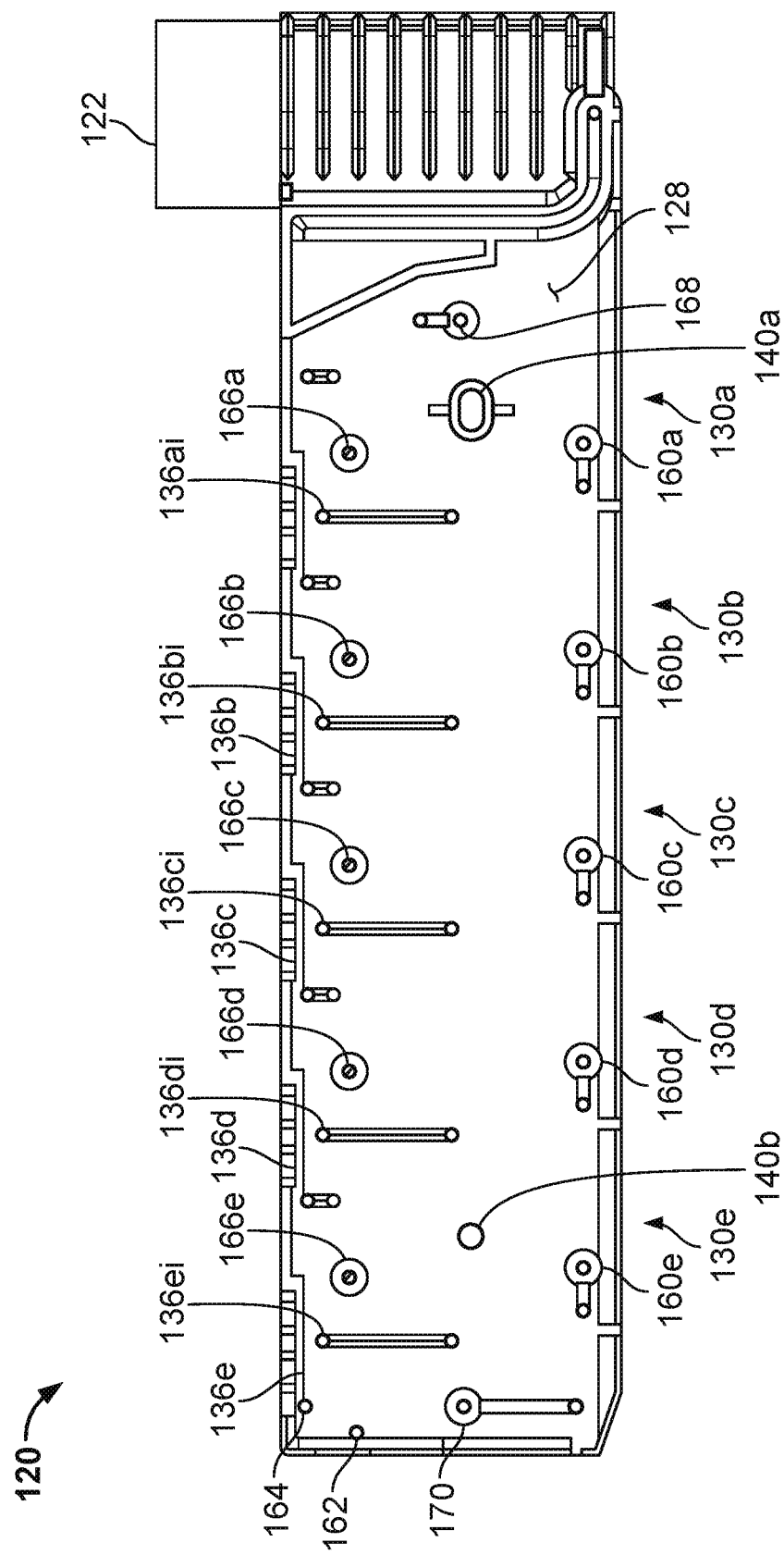
FIG. 7 is a left side view of the cartridge component of FIG. 4.

Referring now to FIGS. 6 and 7, additional features of the cartridge 120 will now be described. In FIG. 6, a side view of particular chambers of the cartridge 120 (measuring chambers 132a-e, reagent mixing chambers 134a-e, and blood coagulation testing chambers 136a-e) is provided. In FIG. 7, a left side view of cartridge 120 and individual channels 130a-e is provided. In this view there is visibility of testing chamber inlet ports 136ai, 136bi, 136ci, 136di, and 136ei for testing chambers 136a-e respectively. The inlet ports 136ai-ei are located near the top of the testing chambers 136a-e, for example, along a side wall of the chamber 136a-e and at a height above the distal head of the pin 138a-e that interacts with the blood sample but below the proximal end of the pin 138a-e (refer to FIG. 10B). This configuration can be advantageous if the blood contains gaseous bubbles, because such gas may be allowed to escape from the blood as the blood enters the cups 136a-e. In addition, this configuration may advantageously minimize fluid flow turbulence as the blood flows into the testing chambers 136a-e.

In the depicted embodiment, the cartridge 120 includes two locator pin receptacles 140a and 140b. The locator pin receptacles 140a and 140b are used to mate with locator pins of the analyzer console 140 (as described further below). In this manner, the cartridge 120 can be accurately positioned in relation to the analyzer console 140.

The cartridge 120 also includes a vacuum application port 162. When a source of vacuum is applied at the vacuum application port 162, and when the vents and valves of the cartridge 120 are in the proper configuration, blood can be drawn into the measuring chambers 132a-e as described above, and as described further below.

The cartridge 120 also includes a pressure application port 164. When a source of pressure is applied at the pressure application port 164, and when the vents and valves of the cartridge 120 are in the proper configuration, blood can be forced to flow from the measuring chambers 132a-e into the mixing chambers 134a-e, and subsequently from the mixing chambers 134a-e into the testing chambers 136a-e as described above, and as described further below.

In the depicted embodiment, the cartridge 120 also includes vents 166a, 166b, 166c, 166d, and 166e. Other cartridge embodiments may include fewer or more vents. The vents 166a-e are confluent with the mixing chambers 134a-e respectively. Accordingly, when the vents 166a-e are open to allow airflow therethrough, air from the mixing chambers 134a-e can be readily displaced from the mixing chambers 134a-e as blood flows into the mixing chambers 134a-e. Conversely, when the vents 166a-e are closed to prevent airflow therethrough, blood is inhibited from flowing into the mixing chambers 134a-e because the air within the mixing chambers 134a-e is not allowed to be displaced therefrom. The vents 166a-e can be individually opened and closed by the analyzer console 140 in accordance with predefined schemes as described further below. Accordingly, blood flow into the mixing chambers 134a-e can be controlled as desired.

In the depicted embodiment, the cartridge 120 also includes valves 168, 170, 160a, 160b, 160c, 160d, and 160e. Other cartridge embodiments may include fewer or more valves. The valves 168, 170, and 160a-e are located within fluid flow paths of the cartridge 120. Accordingly, the valves 168, 170, and 160a-e can be actuated (opened or closed) by the analyzer console 140 to allow or to prevent fluid flow through the fluid flow paths in which the valves 168, 170, and 160a-e are respectively located. For example, the valve 168 is located in the fluid flow path between the needle 123a and the measuring chamber 132a. Accordingly, when the valve 168 is open blood can flow from the needle 123a to the measuring chamber 132a, and when the valve 168 is closed blood cannot flow from the needle 123a to the measuring chamber 132a.

The valve 170 is located in the fluid flow path between the measuring chamber 132e and the overflow chamber 139. Accordingly, when the valve 170 is open blood can flow from the measuring chamber 132e to the overflow chamber 139, and when the valve 170 is closed blood cannot flow from the measuring chamber 132e to the overflow chamber 139.

The valves 160a-e are located in the fluid flow paths between the mixing chambers 134a-e and the testing chambers 136a-e respectively. Accordingly, when the valves 160a-e are open blood can flow from the mixing chambers 134a-e to the testing chambers 136a-e respectively, and when the valves 160a-e are closed blood cannot flow from the mixing chambers 134a-e to the testing chambers 136a-e.

As will be described further below, in some embodiments the valves 160a-e can be individually actuated by pins that are translated towards and away from the valves 160a-e. To close the valves 160a-e, the pins can engage with and distend elastomer members of the valves 160a-e so that the elastomer member makes contact with a valve seat of the valves 160a-e. When such pins are retracted away from the elastomer members of the valves 160a-e, the elastomer members will rebound such that the elastomer member is no longer distended and then the valve is opened. The pins can be translated by solenoids in some embodiments.

Referring to FIG. 6 in more detail, some embodiments of the mixing chambers 134a-e contain: (i) one or more dissolvable reagent beads 180, (ii) multiple retaining elements 182, and (iii) a mixing element 184. The one or more reagent beads 180 are disposed within and retained within the confines of the multiple retaining elements 182. The mixing elements 184 are disposed in the bottom portions of the mixing chambers 134a-e, and are free to move horizontally across the bottom portions of the mixing chambers 134a-e. The multiple retaining elements 182 separate the reagent beads 180 from the mixing element 184, and prevent the mixing element 184 from migrating upward away from the bottom portions of the mixing chambers 134a-e. Preferably, the retaining elements 182 extend into each mixing chamber 134a-e so as to maintain a predetermined vertical position of each of the reagent beads 180 within the mixing chamber (e.g., a vertical position below the height of the blood portion passed into the mixing chamber 134a-e), thereby ensuring that each of the beads 180 will be submerged when the predetermined amount of blood is directed into the respective mixing chamber 134a-e. Also, in some embodiments, the multiple retaining elements 182 in each mixing chamber 134a-e maintain each of the reagent beads 180 in the respective mixing chamber 134a-e separate from one another. In such embodiments, each of the reagent beads 180 is not contacted by other beads 180 in the respective mixing chamber 134a-e, is not contacted by the mixing element 184 in the respective mixing chamber 134a-e, and is maintained at a vertical height within the respective mixing chamber 134a-e below the height of the blood portion transported into the respective mixing chamber 134a-e.

In the depicted embodiment, the one or more dissolvable reagent beads 180 are spherical and are of two different sizes (e.g., about 2 mm diameter and about 3 mm diameter). However, the use of other shapes and/or sizes of reagent beads 180 is also envisioned. In some embodiments, the reagent beads 180 are lyophilized materials, but other forms of materials are also envisioned. The reagent beads 180 can comprise materials such as, but not limited to, $CaCl_2$, ellagic acid/phospholipids, tissue factor, heparinase, polybrene, cytochalasin D, tranexamic acid, and the like, and combinations thereof. The reagent beads 180 are dissolvable in blood. For example, in this particular embodiment, each of the five mixing chambers 134a-e is configured to mix a predetermined volume of blood (as defined by the respective measurement chamber 132a-e) with a different reagent composition (from the one or more reagent beads 180 therein) for purposes of performing five different assays. In this example, the first mixing chamber 134e may include multiple reagent beads 180 the provide $CaCl_2$ and ellagic acid/phospholipids for mixing with the predefined volume of blood (from the corresponding measuring chamber 132e) so that the first sample portion can be used in a first type of assay. Also in this example, the second mixing chamber 134d may include multiple reagent beads 180 the provide $CaCl_2$, ellagic acid/phospholipids, and heparinase for mixing with the predefined volume of blood (from the corresponding measuring chamber 132d) so that the second sample portion can be used in a second type of assay. Further, in this example, the third mixing chamber 134c may include multiple reagent beads 180 the provide $CaCl_2$, tissue factor, and polybrene for mixing with the predefined volume of blood (from the corresponding measuring chamber 132c) so that the third sample portion can be used in a third type of assay. Also in this example, the fourth mixing chamber 134b may include multiple reagent beads 180 the provide $CaCl_2$, tissue factor, polybrene, and cytochalasin D for mixing with the predefined volume of blood (from the corresponding measuring chamber 132b) so that the fourth sample portion can be used in a fourth type of assay. Lastly, in this example, the fifth mixing chamber 134a may include multiple reagent beads 180 the provide $CaCl_2$, tissue factor, polybrene, and tranexamic acid for mixing with the predefined volume of blood (from the corresponding measuring chamber 132a) so that the fifth sample portion can be used in a fifth type of assay.

In some embodiments, the reagent bead 180 carrying the $CaCl_2$ reagent is separated from the rest of the beads 180 in the respective mixing chamber 134a-e so as to first allow mixing and then activation/clotting of the a citrated blood sample. Such separation of the reagent bead 180 carrying the $CaCl_2$ reagent may be achieved using the retaining elements 182 (as described above). Alternatively, such separation can be achieved by retaining the reagent bead 180 carrying the $CaCl_2$ reagent in a separate channel or separate mixing chamber that is separated from other beads 180 in the respective chamber 134a-e (such that the blood portion reaches the $CaCl_2$ reagent after the blood portion mixes with other beads 180 within the respective mixing chamber 134a-e). Alternatively, such separation can be achieved by positioning a $CaCl_2$ reagent liquid or a dried-film $CaCl_2$ reagent in a separate channel so that the blood portion reaches the $CaCl_2$ reagent after the blood portion mixes with other beads 180 in the respective mixing chamber 134a-e. Alternatively, the reagent bead 180 carrying the $CaCl_2$ reagent can be coated with an extra layer (and then retained by the retained by the retaining elements 182 as described above) so that the blood portion begins to dissolve the reagent bead 180 carrying the $CaCl_2$ reagent after the blood portion previously mixes with other beads 180 within the respective mixing chamber 134a-e.

The mixing element 184, comprises a ferromagnetic material including, but not limited to, nickel, cobalt, chromium (IV) oxide, gadolinium, permalloy, and alnico (an aluminum-nickel-cobalt alloy) and the like, and combinations thereof. In the depicted embodiment, the mixing element 184 is spherical and is solid. In other embodiments, the mixing element 184 may have a shape such as, but not limited to, cubical, conical, cylindrical, fan-shaped, elongated, prismatic, and the like, as well as irregular shapes. In some embodiments, the mixing element 184 may include one or more surface features such as protrusions, indentations, or holes, and the like.

As will be described further below, the mixing elements 184 are movable within the mixing chambers 134a-e in response to movement of magnets with which the mixing elements 184 magnetically couple. The magnets that the mixing elements 184 magnetically couple with are contained within the analyzer console 140. The movement of the mixing elements 184 encourages the reagent beads 180 to dissolve in the blood contained within the mixing chambers 134a-e.

Referring now to FIGS. 8A-8H schematically depict an example fluidic control process 200 that can be used with the thromboelastometry systems provided herein. The process 200 begins with blood contained only within the blood collection tube 10, and ends with blood/reagent mixtures contained in cups 136a-e that are configured for rotary thromboelastometry. It should be understood that, in some embodiments, the cartridge 120 (refer to FIGS. 1-7) that is used to implement the fluidic control process 200 is heated (e.g., to about 37° C.) prior to having any blood therein.

Figure 8A:
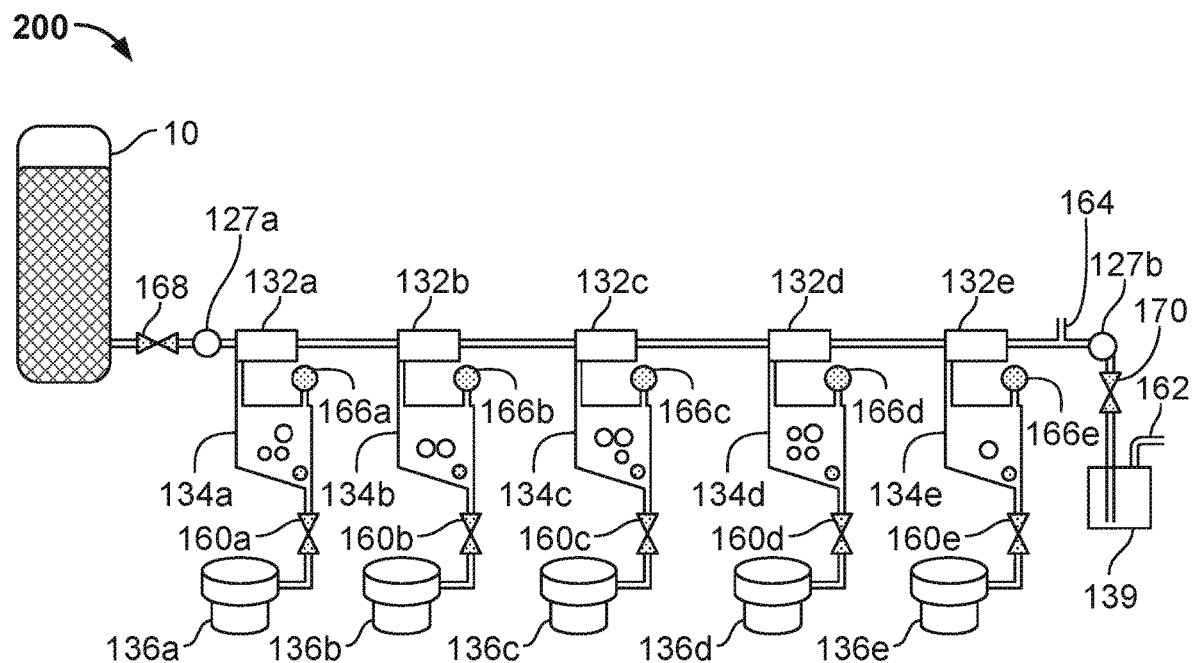
FIG. 8A-8H are a series of schematic diagrams depicting operations of the thromboelastometry system of FIGS. 1A, 1B, 2, and 3, in accordance with some embodiments.

Referring to FIG. 8A, the example fluidic control process 200 includes the blood collection tube 10, the measuring chambers 132a-e, the mixing chambers 134a-e, and cups 136a-e, the overflow chamber 139, the blood detection locations 127a and 127b, the vacuum application port 162, the pressure application port 164, the vents 166a-e, the valves 168, 170, and 160a-e. In the depicted configuration, valve 168 is closed, thereby retaining the blood substantially within the blood collection tube 10.

While the example fluidic control process 200 includes five blood flow channels (each comprising a measuring chamber 132a-e, a mixing chamber 134a-e, and a cup 136a-e respectively), it should be understood that having five blood flow channels is not required in all embodiments. For example, in some embodiments only a single blood flow channel is included. Alternately, two blood flow channels are included, or three blood flow channels are included, or four blood flow channels are included, or six blood flow channels are included, or more than six blood flow channels are included.

Figure 8B:
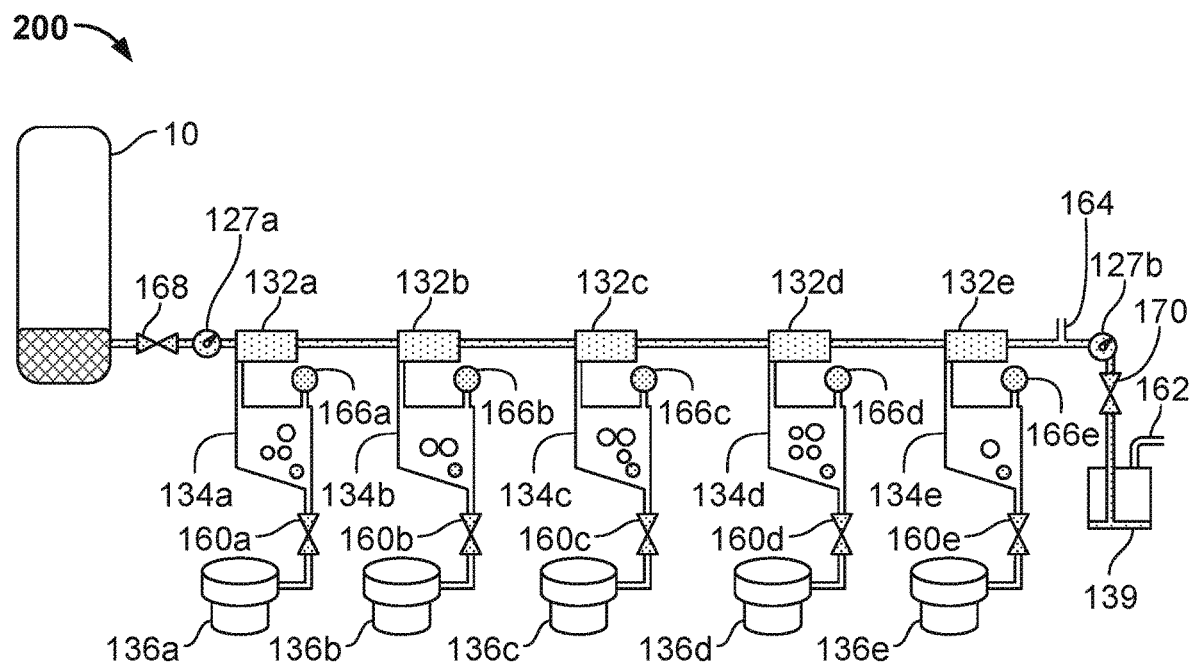

Referring to FIG. 8B, the measuring chambers 132a-e are filled with blood, and a small amount of blood is contained within the overflow chamber 139. To arrive at this state, the following changes were made (in comparison to FIG. 8A) and/or the following conditions existed: (i) the valves 168 and 170 were opened, (ii) the valves 160a-e were closed, (iii) the vents 166a-e were closed, (iv) a negative pressure was applied to the vacuum application port 162, and (v) the pressure application port 164 was unpressurized. Accordingly, the blood flowed: (i) out of the blood collection tube 10, (ii) through the valve 168, (iii) through the blood detection location 127a, (iv) into and filling the measuring chamber 132a, (v) into and filling the measuring chamber 132b, (vi) into and filling the measuring chamber 132c, (vii) into and filling the measuring chamber 132d, (viii) into and filling the measuring chamber 132e, (ix) through blood detection location 127b, (x) through valve 170, and (xi) into the overflow chamber 139. When blood was detected in the blood detection location 127b, the application of the negative pressure was discontinued—thereby stopping further blood flow.

Figure 8C:
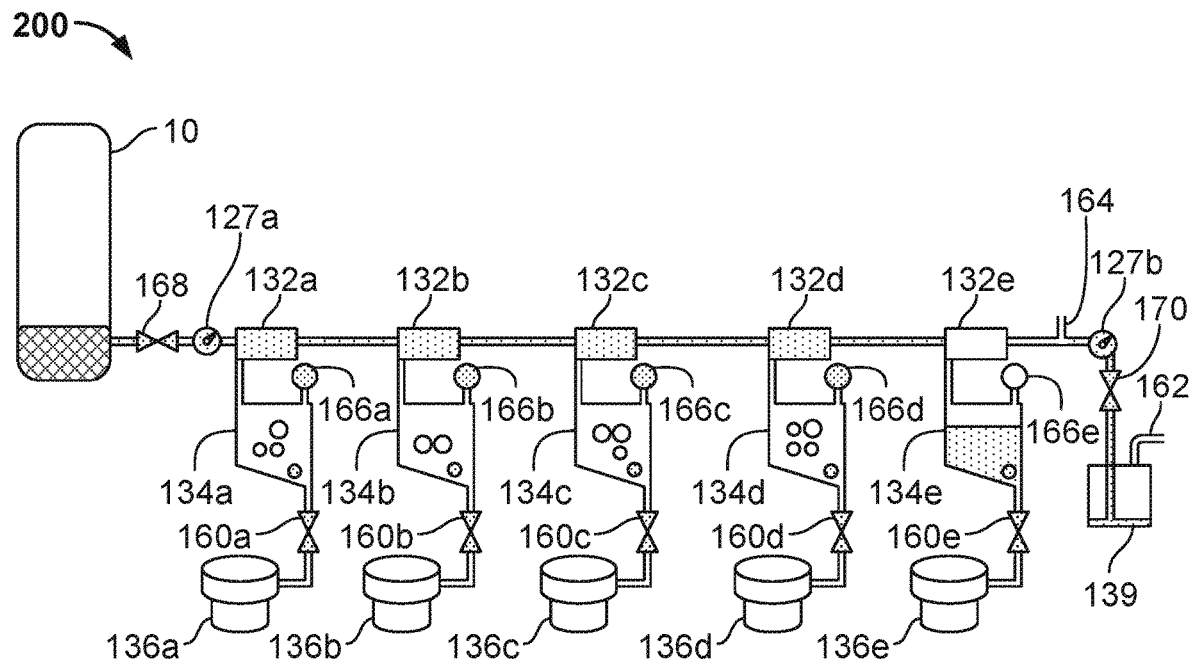

Referring to FIG. 8C, the measuring chambers 132a-d are still filled with blood, but the blood from the measuring chamber 132e has transferred to the mixing chamber 134e. To arrive at this state, the following changes were made (in comparison to FIG. 8B) and/or the following conditions existed: (i) the valves 168 and 170 were closed, (ii) the valves 160a-e remained closed, (iii) the vents 166a-d remained closed, (iv) the vent 166e was opened, and (v) a source of air pressure was applied to the pressure application port 164. Accordingly, the blood flowed: (i) out of the measuring chamber 132e, and (ii) into the mixing chamber 134e. Because the vents 166a-d and the valves 160a-d remained closed, the blood in the measuring chambers 132a-d did not flow into the mixing chambers 134a-d. With blood in the mixing chamber 134e, the mixing element in mixing chamber 134e can move and agitate the blood to facilitate the dissolving of the reagent beads therein.

Figure 8D:
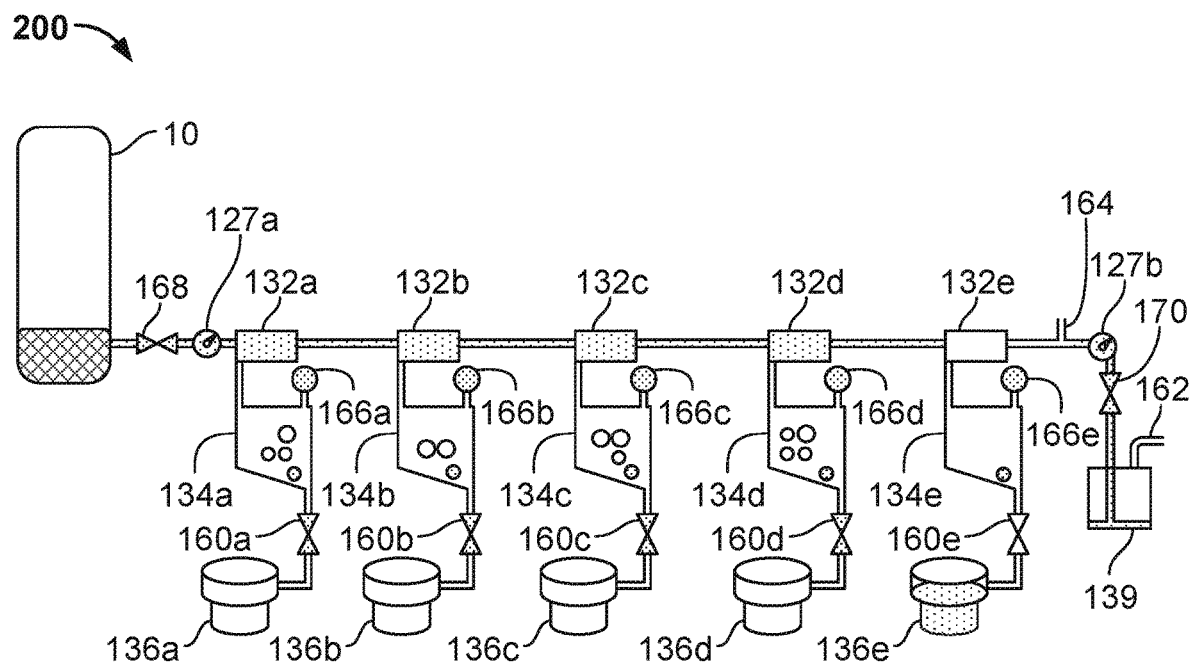

Referring to FIG. 8D, the measuring chambers 132a-d are still filled with blood, and the blood/reagent mixture that was in the mixing chamber 134e (refer to FIG. 8C) has transferred to the cup 136e. To arrive at this state, the following changes were made (in comparison to FIG. 8C) and/or the following conditions existed: (i) the valves 168 and 170 remained closed, (ii) the valve 160e was opened, (iii) the valves 160a-d remained closed, (iv) the vent 166e was closed (v) the vents 166a-d remained closed, and (vi) a source of air pressure was applied to the pressure application port 164. Accordingly, the blood/reagent mixture flowed: (i) out of the mixing chamber 134e, and (ii) into the cup 136e. Because the vents 166a-d and the valves 160a-d remained closed, the blood did not flow from the measuring chambers 132a-d towards the mixing chambers 134a-d. With the blood/reagent mixture located in the cup 136e, rotary thromboelastometry can begin in the cup 136e.

Figure 8E:
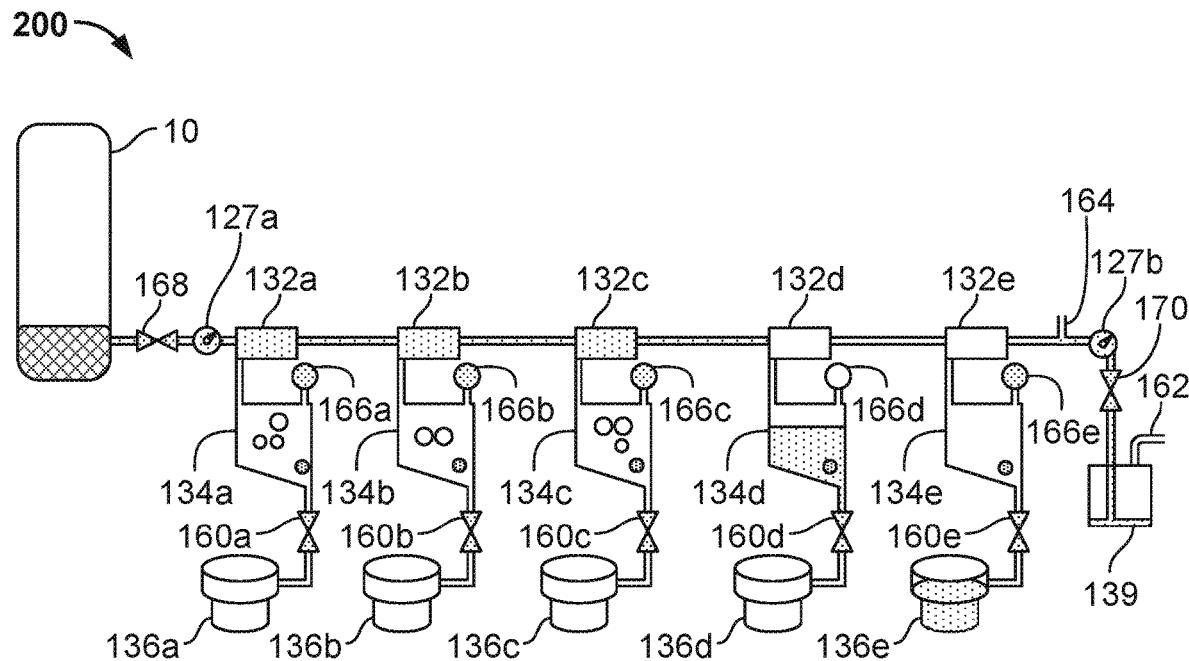

Referring to FIG. 8E, the measuring chambers 132a-c are still filled with blood, the cup 136e is still filled with blood/reagent mixture, and the blood that was in the measuring chamber 132d (refer to FIG. 8D) has transferred to the mixing chamber 134d. To arrive at this state, the following changes were made (in comparison to FIG. 8D) and/or the following conditions existed: (i) the valves 168 and 170 remained closed, (ii) the valve 160e was closed, (iii) the valves 160a-d remained closed, (iv) the vent 166d was opened (v) the vents 166a-c and 166e remained closed, and (vi) a source of air pressure was applied to the pressure application port 164. Accordingly, the blood flowed: (i) out of the measuring chamber 132d, and (ii) into the mixing chamber 134d. Because the vents 166a-c and because the valves 160a-c remained closed, the blood did not flow from the measuring chambers 132a-c towards the mixing chambers 134a-c. With blood in the mixing chamber 134d, the mixing element in mixing chamber 134d can agitate the blood to facilitate the dissolving of the reagent beads therein.

Figure 8F:
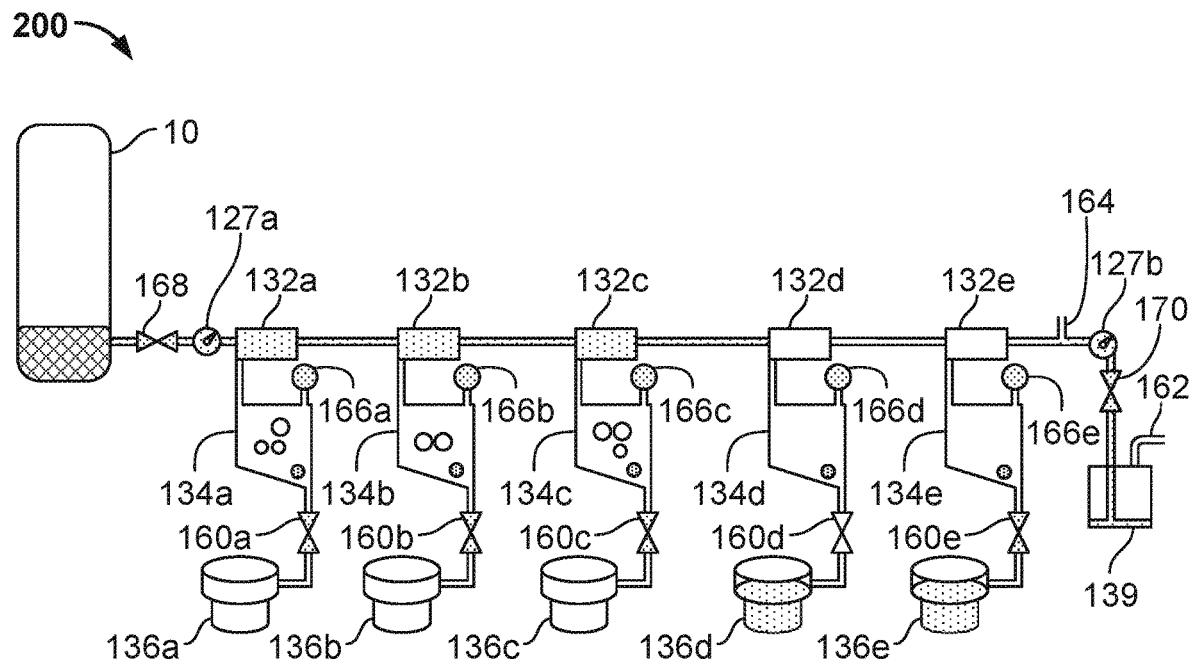

Referring to FIG. 8F, the measuring chambers 132a-c are still filled with blood, the cup 136e is still filled with blood/reagent mixture, and the blood/reagent mixture that was in the mixing chamber 134d (refer to FIG. 8E) has transferred to the cup 136d. To arrive at this state, the following changes were made (in comparison to FIG. 8E) and/or the following conditions existed: (i) the valves 168 and 170 remained closed, (ii) the valve 160d was opened, (iii) the valves 160a-c and 160e remained closed, (iv) the vent 166d was closed (v) the vents 166a-c and 166e remained closed, and (vi) a source of air pressure was applied to the pressure application port 164. Accordingly, the blood/reagent mixture flowed: (i) out of the mixing chamber 134d, and (ii) into the cup 136d. Because the vents 166a-c and the valves 160a-c remained closed, the blood did not flow from the measuring chambers 132a-c towards the mixing chambers 134a-c. With the blood/reagent mixture located in the cup 136d, rotary thromboelastometry can begin in cup 136d.

Figure 8G:
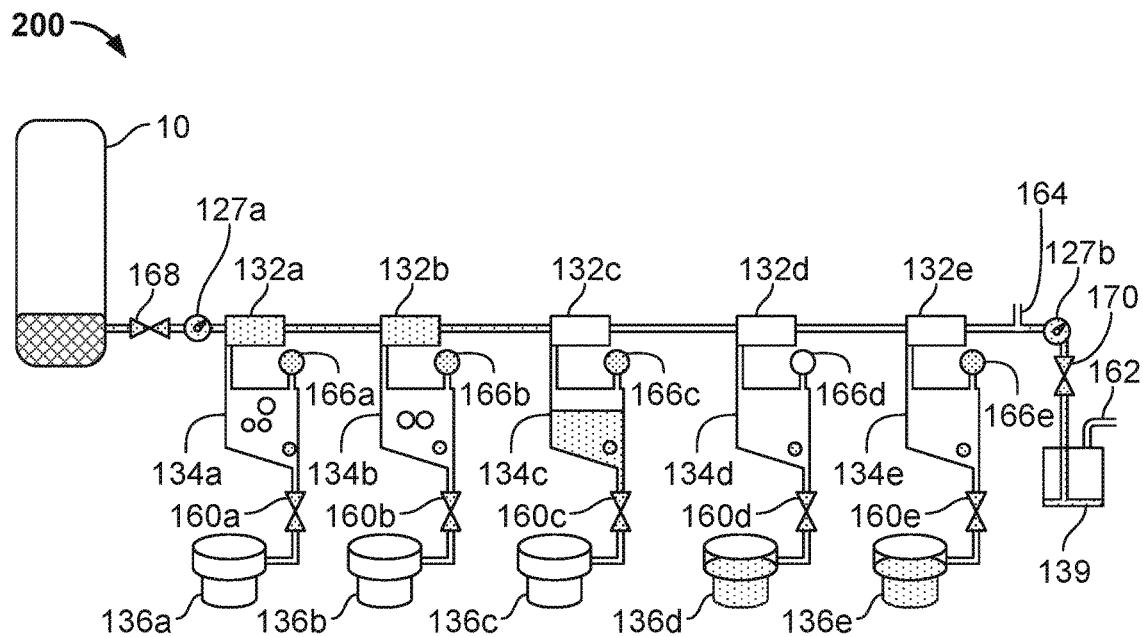

Referring to FIG. 8G the measuring chambers 132a-b are still filled with blood, the cups 136d-e are still filled with blood/reagent mixture, and the blood that was in the measuring chamber 132c (refer to FIG. 8F) has transferred to the mixing chamber 134c. To arrive at this state, the following changes were made (in comparison to FIG. 8F) and/or the following conditions existed: (i) the valves 168 and 170 remained closed, (ii) the valve 160d was closed, (iii) the valves 160*a-c* and 160*e* remained closed, (iv) the vent 166*c* was opened (iv) the vents 166*a-b* and 166*d-e* remained closed, and (v) a source of air pressure was applied to the pressure application port 164. Accordingly, the blood flowed: (i) out of the measuring chamber 132*c*, and (ii) into the mixing chamber 134*c*. Because the vents 166*a-b* and because the valves 160*a-b* remained closed, the blood did not flow from the measuring chambers 132*a-b* towards the mixing chambers 134*a-b*. With blood in the mixing chamber 134*c*, the mixing element in mixing chamber 134*c* can agitate the blood to facilitate the dissolving of the reagent beads therein.

Figure 8H:
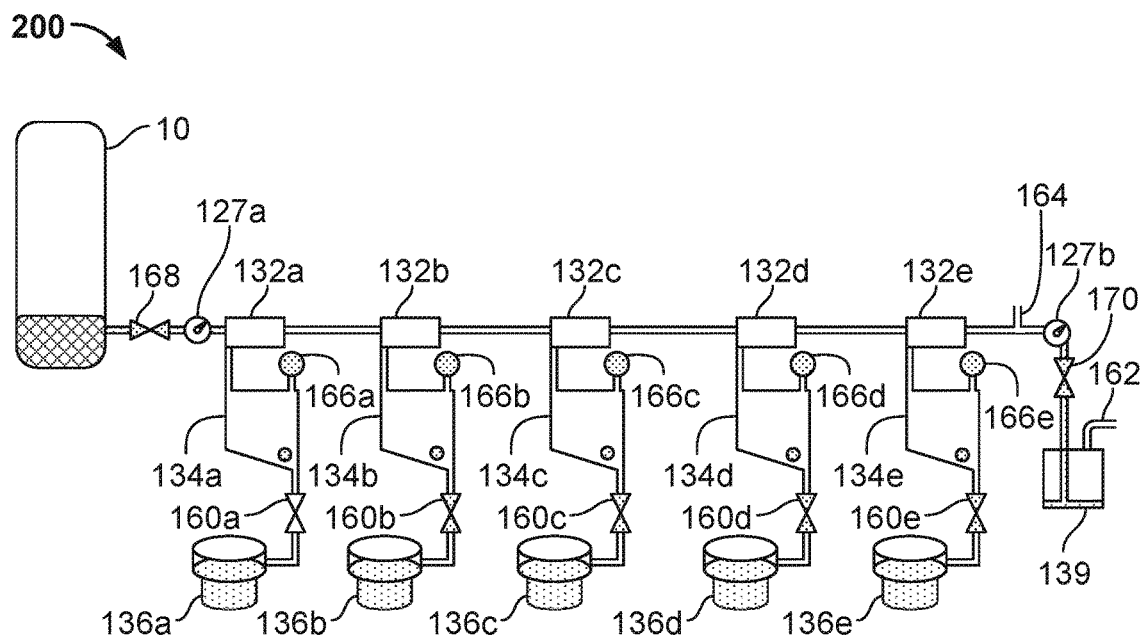

Referring to FIG. 8H, the completion of the process 200 is depicted. That is, the cups 136*a-c* all contain blood/reagent mixtures and rotary thromboelastometry can be taking place in the cups 136*a-e*. This state can be attained in accordance with the method of actuating the valves 168, 170, and 160*a-e*, and the vents 166*a-e*, in conjunction with applying vacuum to the vacuum application port 162 or pressure to the pressure application port 164 as described above.

Figure 9:
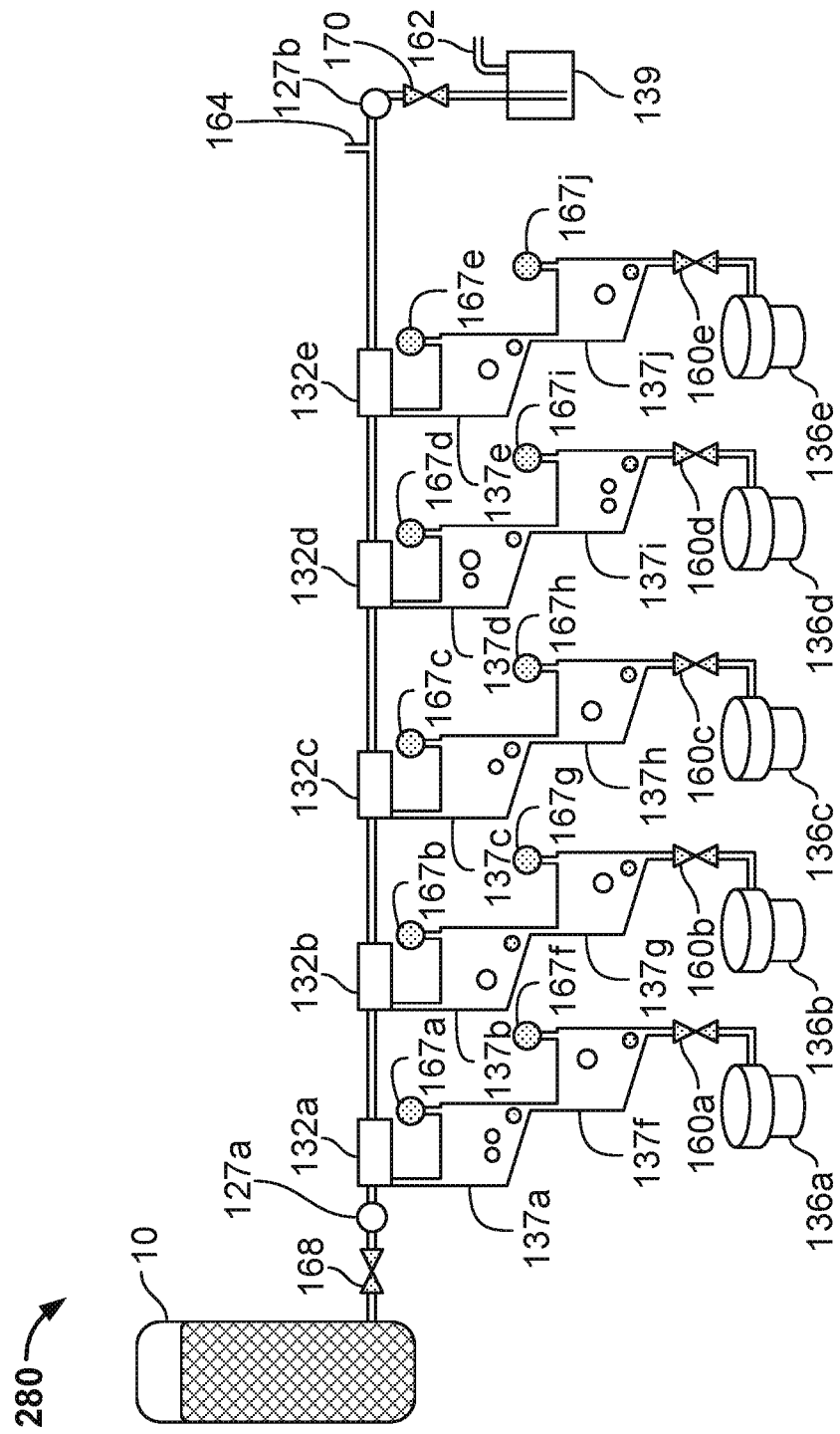
FIG. 9 is a schematic diagram of another example thromboelastometry system, in accordance with some embodiments.

Referring to FIG. 9, in some alternative embodiments, one or more of the individual blood flow channels or paths can include multiple mixing chambers that are arranged in series. For example, the example fluidic control process 280 includes five blood flow channels (similar to the number of channels in the embodiment of FIGS. 8A-H), but each of the channels include two mixing chambers that are arranged in series (rather than a single mixing chamber for each respective mixing chamber like the embodiment of FIGS. 8A-H). That is, mixing chambers 137*a* and 137*f* are arranged in series between the measurement chamber 132*a* and the cup 136*a*; mixing chambers 137*b* and 137*g* are arranged in series between the measurement chamber 132*b* and the cup 136*b*; mixing chambers 137*c* and 137*h* are arranged in series between the measurement chamber 132*c* and the cup 136*c*; mixing chambers 137*d* and 137*i* are arranged in series between the measurement chamber 132*d* and the cup 136*d*; and mixing chambers 137*e* and 137*j* are arranged in series between the measurement chamber 132*e* and the cup 136*e*.

In some embodiments, the reagent bead carrying the $CaCl_2$ reagent is separated from the other the reagent beads by locating the $CaCl_2$ reagent in the second of the two mixing chambers that are arranged in series. In that manner, the serial mixing chambers can allow the blood sample to be mixed with reagents and subsequently, at a controlled point in time, activation/clotting of the blood sample can be initiated.

While the example fluidic control process 280 includes five blood flow channels that each include two mixing chambers that are arranged in series, it should be understood that such a configuration is not required in all embodiments. For example, in some embodiments only a single blood flow channel that includes two mixing chambers that are arranged in series is included in a cartridge. Such a single blood flow channel with two mixing chambers may be the only blood flow channel in the cartridge, or may be combined in a cartridge with one or more other blood flow channels that include a single mixing chamber. It should be understood that all combinations and permutations of number of blood flow channels and mixing chambers are included within the scope of this disclosure.

Figure 10A:
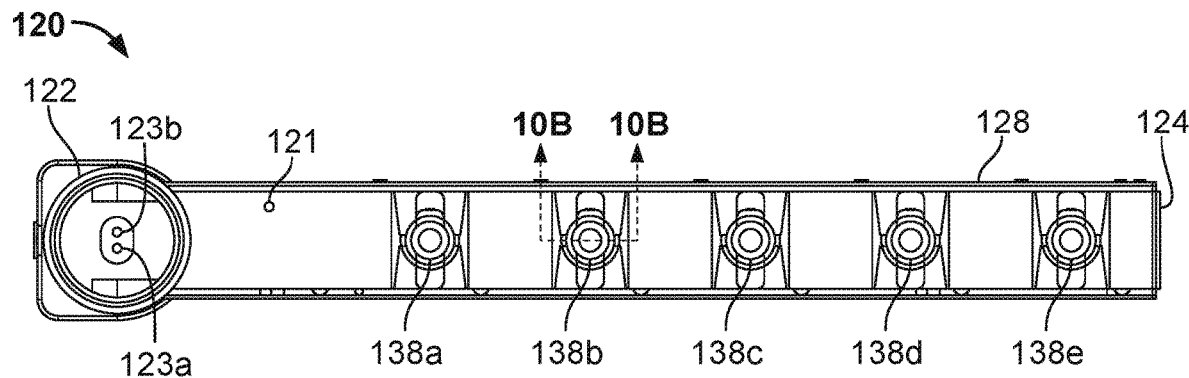
FIG. 10A is a top view of the cartridge component of FIG. 4.
Figure 10B:
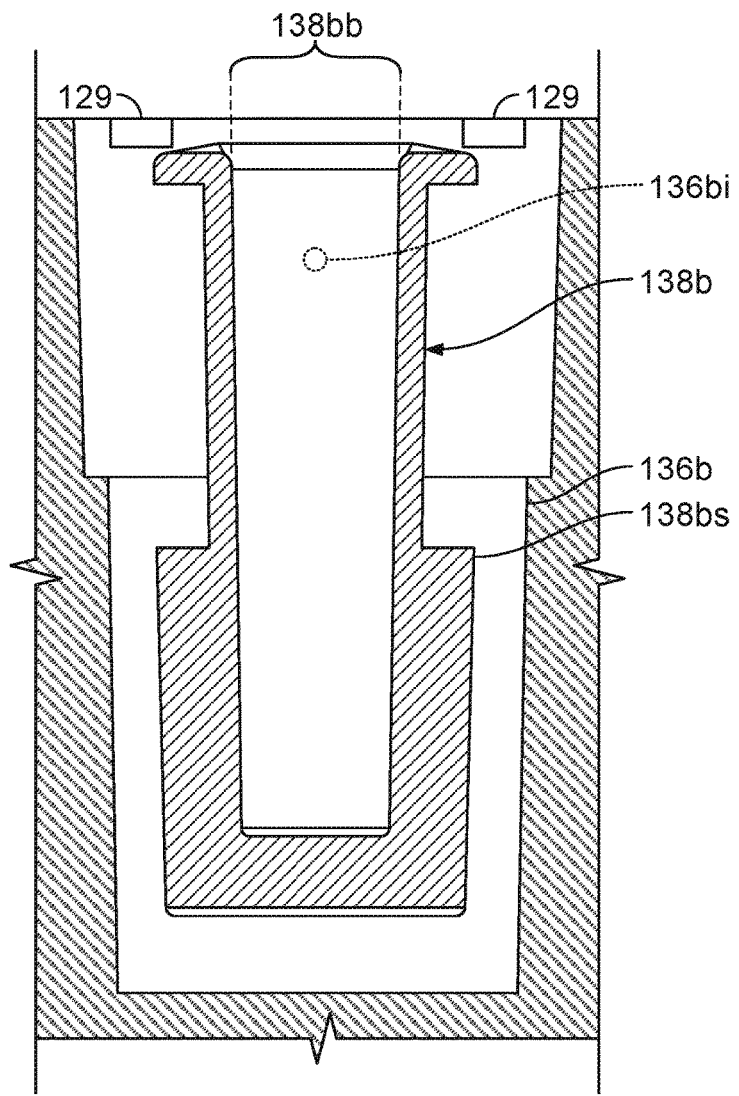
FIG. 10B is a partial cross-sectional view of the cartridge component of FIG. 10A.

Turning now to the blood coagulation testing chambers 136*a-e* in more detail, the chambers 136*a-e* can be configured to provide viscoelastic testing on the blood sample portion drawn into each chamber. Referring to FIGS. 10A and 10B, the pins 138*a-e* are located in the cartridge 120. A representative example showing the pin 138*b* located in the cup 136*b* illustrates that a clearance space exists between the outer diameter of the pin 138*b* and the inner diameter of the cup 136*b*. A blood/reagent mixture will at least partially fill the clearance space when rotary thromboelastometry is being performed therein. The pin 138*b* has a shoulder 138*bs*. The clearance space between the outer diameter of the pin 138*b* and the inner diameter of the cup 136*b* is less in the areas below the shoulder 138*bs* than in the areas above the shoulder 138*bs*. The areas between the outer diameter of the pin 138*b* and the inner diameter of the cup 136*b* that are below the shoulder 138*bs* are the areas that are active in regard to performing rotary thromboelastometry.

The cup 136*b* and pin 138*b* are shown in cross-section in FIG. 10B (in accordance with section 10B-10B of FIG. 10A). In addition, a blood inlet port 136*bi* (located behind pin 138*b* in the orientation of FIG. 10B) is provided so that the blood/reagent mixture will flow into the cup 136*b* via the blood inlet port 136*bi*. In the depicted embodiment, the cup inlet port 136*bi* is located in a sidewall of cup 136*b* at a height above the widened distal portion (refer to shoulder 138*bs*) of the pin 138*b* but below the proximal end of the pin 138*b* (refer to end near the entry to the axial bore 138*bb* of the pin 138*b*). In this configuration, the blood/reagent mixture will flow into the cup 136*b* so as to reduce the potential for bubble formation. In addition, locating the cup inlet port 136*bi* near the top of cup 136*b* eliminates the effects that the cup inlet port 136*bi* may otherwise have on the thromboelastometry measurements performed in the cup 136*b* if the cup inlet port 136*bi* is located in the active space between the inner diameter of the cup 136*b* and the outer diameter of the pin 138*b* below the shoulder 138*bs*.

In the depicted embodiment, the top of the cartridge 124 includes a vent 121. The vent 121 is in fluid communication with the needle 123*b*. Therefore, when air for venting a blood sample tube located in sample well 122 is needed, air is drawn through the vent 121 and channeled into the blood sample tube via the needle 123*b*.

Each of the pins 138*a-e* includes an axial bore. For example, the pin 138*b* includes an axial bore 138*bb*. The axial bore 138*bb* can be used to engage with a shaft (not shown in FIG. 10B) for performing rotary thromboelastometry. Referring to FIG. 10C, an example rotary thromboelastometry assembly 300*b* can engage with the pin 138*b* to perform rotary thromboelastometry on a blood sample contained in the cup 136*b*. In this particular embodiment, the example rotary thromboelastometry assembly 300*b* includes a baseplate 302, a shaft 310*b*, a bearing 312*b*, a mirror 314*b*, a counterforce spring 320*b*, a light source 330*b*, and a detector 340*b* (e.g., a charge-coupled device or the like). The baseplate 302 can be lowered, as represented by arrows 318*b*, such that a tip portion of the shaft 310*b* enters the bore 138*bb* to become releasably coupled with the pin 138*b*. The bearing 312*b* is engaged with the baseplate 302 and the shaft 310*b* to facilitate rotational movement of the shaft 310*b* in relation to the baseplate 302. The counterforce spring 320*b* is coupled to the shaft 310*b* and oscillation of the spring 320*b* can induce the shaft 310*b* to oscillate back and forth by about +/−5° as represented by arrow 316*b*. The mirror 315 is coupled to the shaft 310*b*. The light source 330*b* is configured to project light towards the mirror 314*b*, and light can be reflected from the mirror 315 towards the detector 340*b* (depending on the rotational orientation of the shaft 310*b*). Accordingly, the motion of the pin 138*b* is detected by an optical detection system. It should be understood that other configurations of the rotary thromboelastometry assembly 300*b* are also envisioned within the scope of this disclosure.

The detected motion data is analyzed by an algorithm running on the analyzer console 140 (refer to FIGS. 1-3) to process and determine the thromboelastometry results. This system facilitates various thromboelastometry parameters such as, but not limited to, clotting time, clot formation time, alpha angle, amplitude, maximum clot firmness, lysis onset time, lysis time, lysis index (%), and maximum lysis (%).

As the blood in the cup 136*b* begins to coagulate, the motion amplitude of the shaft 310*b* starts to decrease (as detected by the deflection of the light beam from mirror 315 towards the detector 340*b*). During coagulation, the blood's fibrin backbone (together with platelets) creates a mechanical elastic linkage between the surfaces of the cup 136*b* and the pin 138*b*. A proceeding coagulation process induced by adding one or more of the aforementioned activating factors can thus be observed and quantified. In this way, various deficiencies of a patient's hemostatic status can be revealed and can be interpreted for proper medical intervention. At the end of the test process, the baseplate 302 can rise to uncouple the shaft 310*b* from the pin 138*b*.

Figure 11:
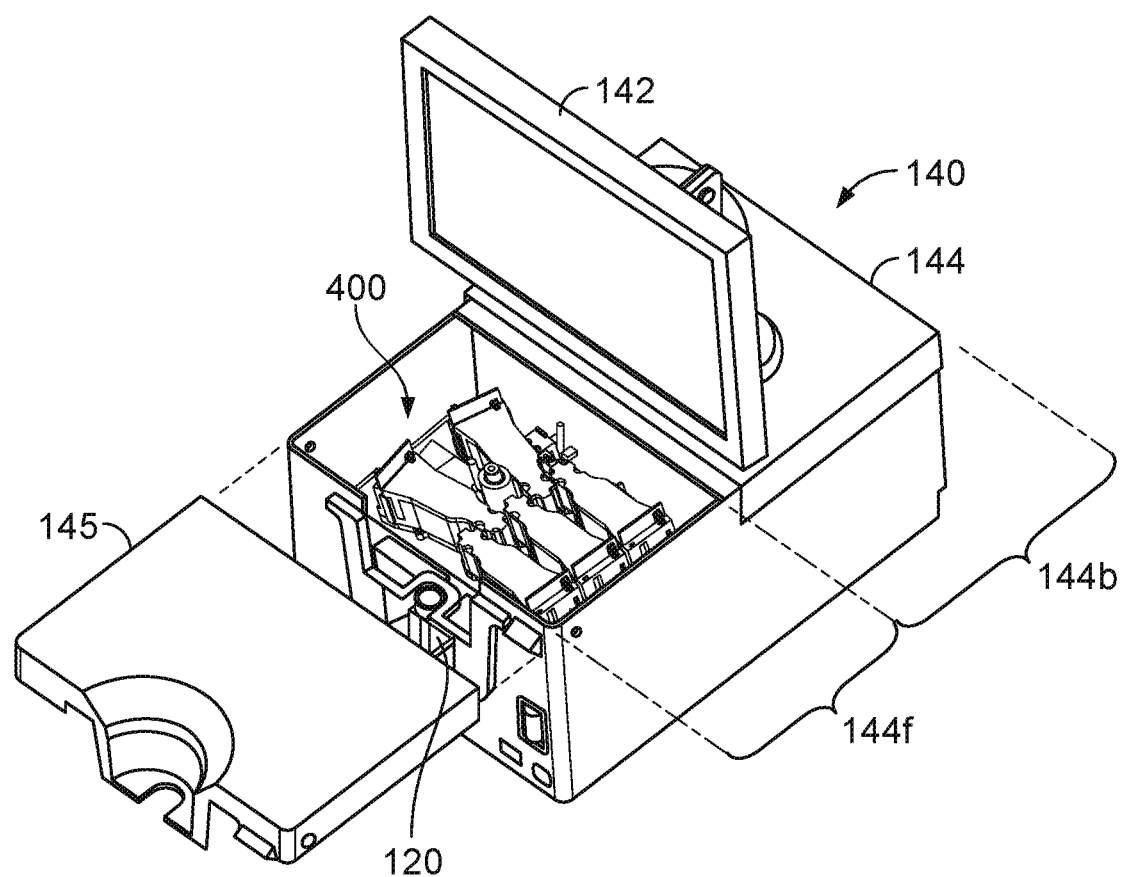
FIG. 11 is an exploded perspective view of a thromboelastometry analyzer console of the thromboelastometry system of FIGS. 1A, 1B, 2, and 3.

Referring to FIG. 11, the main chassis 144 of the analyzer console 140 can include a front portion 144*f* and a rear portion 144*b*. In some embodiments, the rear portion 144*b* houses at least some of the computer and electronic components that are necessary for the operations of the analyzer console 140. For example, the rear portion 144*b* can house hardware devices and software such as, but not limited to, computer processors, memory devices, an operating system and other executable instructions, power source(s), user interface controls, communication devices, circuit boards, and the like.

In the depicted embodiment, the front portion 144*f* includes a cover 145 and a sample handler assembly 400. The sample handler assembly 400 defines an interior space in which the cartridge 120 can be received. In some embodiments, the sample handler assembly 400 is a modular sub-assembly of the analyzer console 140, and the sample handler assembly 400 can be readily removed from the analyzer console 140 for service. The sample handler assembly 400 is electrically interconnected with the computer and electronic components that are housed in the rear portion 144*b*. As such, the analyzer console 140 can perform rotary thromboelastometry on a blood sample located in cartridge 120 and display the results on the touchscreen display 142.

Figure 12:
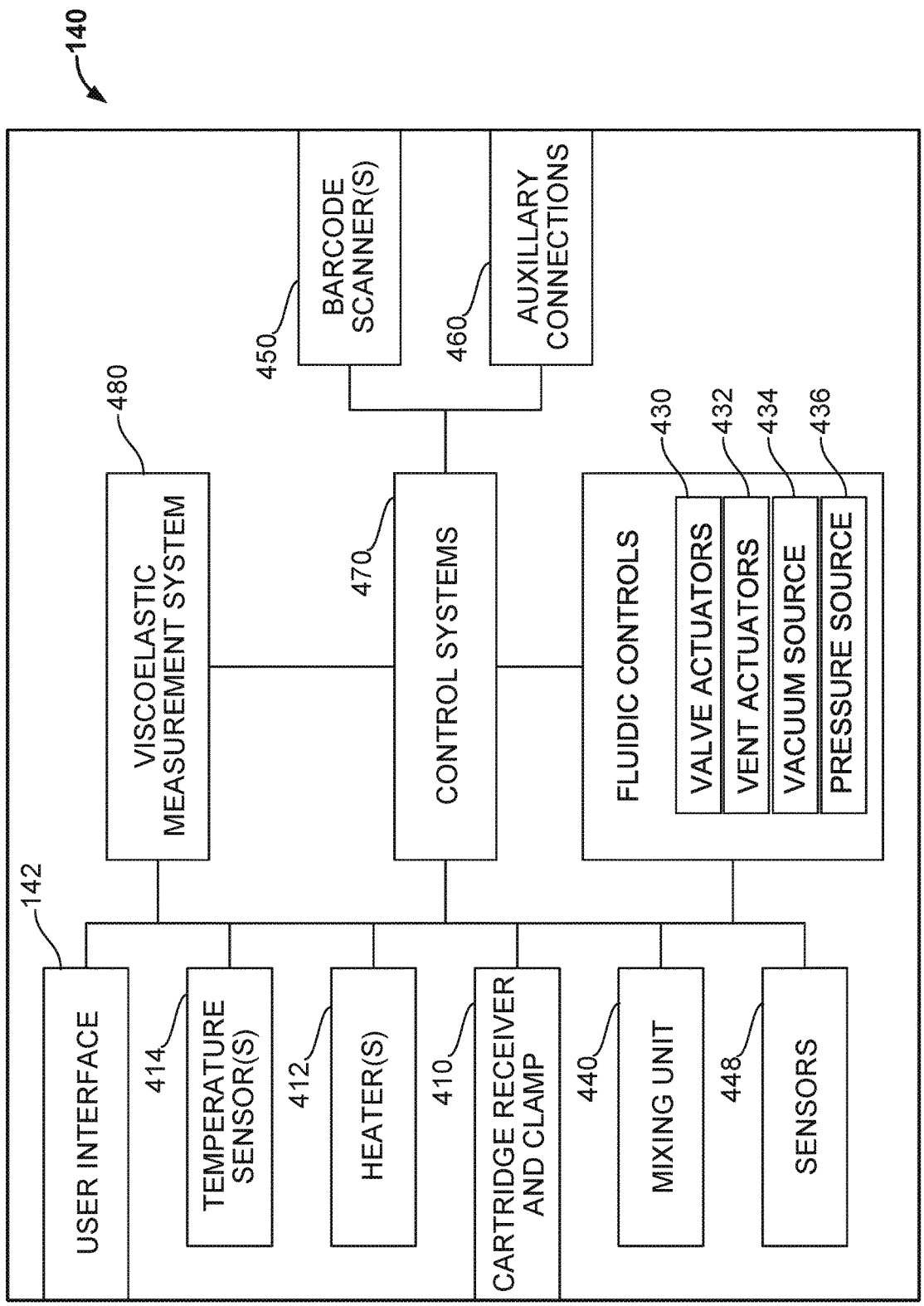
FIG. 12 is a block diagram that schematically depicts subsystems of the thromboelastometry analyzer console of the thromboelastometry system of FIGS. 1A, 1B, 2, and 3.

Referring now to FIGS. 11 and 12, the analyzer console 140 can include a cartridge receiver and clamp 410 and a viscoelastic measurement system 480. A mechanical frame assembly is used to support the cartridge receiver and clamp 410 and the viscoelastic measurement system 480 in orientations such that the cartridge receiver and clamp 410 and the viscoelastic measurement system 480 can function symbiotically.

Portions of the cartridge receiver and clamp 410 and the viscoelastic measurement system 480 are moveable in relation to the mechanical frame assembly (which is stationary in relation to the analyzer console 140). For example, the viscoelastic measurement system 480 can move upward and downward. As will be described further below, the viscoelastic measurement system 480 can move downward to engage with the cartridge 120 (e.g., refer to FIG. 11), and upward to disengage from the cartridge 120. A portion of the cartridge receiver and clamp 410 can move horizontally in relation to the mechanical frame assembly. As will be described further below, a portion of the cartridge receiver and clamp 410 can move horizontally to clamp or unclamp the cartridge 120 within the sample handler assembly 400.

In some embodiments, the cartridge receiver and clamp 410 includes a movable block sub-assembly and a stationary block sub-assembly. A space exists between the movable block sub-assembly and the stationary block sub-assembly in which the cartridge 120 can be received. The movable block sub-assembly can be translated towards or away from the stationary block sub-assembly. Accordingly, the cartridge 120 can be clamped and unclamped between the movable block sub-assembly and the stationary block sub-assembly by virtue of the relative movement therebetween. In some embodiments, the viscoelastic measurement system 480 is mounted to the movable block sub-assembly. Therefore, as the movable block sub-assembly is translated, the viscoelastic measurement system 480 is also translated.

In some embodiments, the moveable block sub-assembly can be translated by an electric motor. In particular embodiments, the motor is a stepper motor. In some embodiments, a gear reducer is coupled to the motor. Using a belt and pulley arrangement for compactness, the motor can be used to drive a lead screw. The threads of the lead screw can be engaged with complementary threads of the movable block such that a rotation of the lead screw results in horizontal translation of the movable block. In some embodiments, end-of-travel detectors (e.g., proximity sensors, optical sensors, micro-switches, and the like) are included to detect when the moveable block sub-assembly has been horizontally translated to the desired end-of-travel positions.

In some embodiments, one or more springs can extend between the movable moveable block sub-assembly and the stationary block sub-assembly. The springs can help facilitate a suitable clamping force between the movable block sub-assembly and the stationary block sub-assembly. In some embodiments, the springs are adjustable.

In some embodiments, portions of the moveable block sub-assembly and the stationary block sub-assembly that make contact with the cartridge 120 comprise a flexible or compressible material so that while the cartridge 120 is clamped it is also protected from damage.

In particular embodiments, the moveable block sub-assembly can include one or more features on the clamping face of the moveable block sub-assembly that serve to position the cartridge 120 in the desired location within the sample handler assembly 400. For example, in some embodiments the moveable block sub-assembly includes two locator pins that can mate with the locator pin receptacles 140*a* and 140*b* of the cartridge 120 (refer to FIG. 7) to accurately position the cartridge 120 in relation to the sample handler assembly 400.

In some embodiments, one or both of the moveable block sub-assembly and the stationary block sub-assembly include heating devices 412 that can warm the cartridge 120 when the cartridge 120 is clamped therebetween. For example, in some embodiments the heaters 412 are electrical resistance heaters that are used to heat at least portions of the cartridge 120. In some embodiments, the heaters 412 are configured to facilitate warming of individual portions of the cartridge 120 independently from other portions of the cartridge 120. For example, one or more of the individual blood flow channels 130*a*, 130*b*, 130*c*, 130*d*, and 130*e* (refer to FIGS. 4-7) can be independently warmed in some such embodiments. Warming may be performed to one or more sides of the cartridge 120. Other types of warming modalities may be used including, but not limited to, IR, ultrasonic, microwave, and the like.

In particular embodiments, one or more temperature sensors 414 are included that can detect the temperature of the cartridge 120 at one or more locations on the cartridge 120. For example, in some embodiments the one or more temperature sensors 414 can be thermocouples, thermistors, infra-red temperature sensors, and the like. Accordingly, the analyzer console 140 can control the heating of the cartridge 120 to a predetermined temperature (e.g., about 37° C.) using the heaters 412 and the temperature sensors 414.

The moveable block sub-assembly can include multiple solenoids that are used to actuate the aforementioned vents and valves of the cartridge 120. For example (referring also to FIG. 7), the valves 168, 170, and 160 a-e, can be actuated by valve actuators 430 and the vents 166a-e can be actuated by vent actuators 432. In some embodiments, the valve actuators 430 and the vent actuators 432 comprise solenoids. Actuation of the valves 168, 170, and 160 a-e by the valve actuators 430 can be accomplished by coupling pins to the valve actuators 430 that are extendable from the moveable block sub-assembly to make contact with and to distend valve elastomer members so that the elastomer members make contact with a valve seat within the cartridge 120. Actuation of the vents 166a-e by the vent actuators 432 can be accomplished by coupling pins with resilient tips that are extendable from the moveable block sub-assembly to obstruct the vents 166 a-e. Such pins with resilient tips can act as stoppers to substantially prevent airflow through the vents 166a-e. In some embodiments, the valve actuators 430 and the vent actuators 432 comprise solenoids that include internal springs that cause the valve actuators 430 and the vent actuators 432 to be normally extended (e.g., when the electrical power is removed from the solenoids). Accordingly, such normally closed solenoids will close the vents and valves of the cartridge 120 as a default configuration.

The sample handler assembly 400 also includes pressure source 436 and vacuum source 434 by which air pressure and vacuum can be applied to the pressure application port 164 and the vacuum application port 162 of cartridge 120 respectively (refer to FIG. 7). For example, the pressure source 436 and vacuum source 434 can make contact with the cartridge 120 and can convey pressure or vacuum to the pressure application port 164 and the vacuum application port 162 when the cartridge 120 is clamped within the cartridge receiver and clamp 410. The pressure source 436 and vacuum source 434 are at least partially made of a resilient material in some embodiments. For example, in some embodiments the pressure source 436 and vacuum source 434 are at least partially made of a resilient material such as, but not limited to, silicone, butyl rubber, nitrile rubber, ethylene propylene rubber, fluoroelastomers, and the like. One or more internally-housed pressure and/or vacuum pumps (not shown) can also be included in the analyzer console 140. Such internally-housed pressure and vacuum pumps can be used to generate the air pressure or vacuum that is applied to the cartridge 120 to induce the transport of blood within the cartridge 120 as described above in reference to FIGS. 8A-8H.

As previously described, the cartridge receiver and clamp 410 also includes the stationary block sub-assembly. In some embodiments, the stationary block sub-assembly does not move in relation to the mechanical frame assembly and in relation to the analyzer console 140 as a whole.

In some embodiments, the analyzer console 140 includes a mixing unit 440. In particular embodiments, the mixing unit 440 includes a motor, a crank and connecting rod assembly, and a magnet shuttle. These components can be used to magnetically couple with the mixing elements of the cartridge 120 and to induce movement of the mixing elements within the mixing chambers 134a-e. The movement of the mixing elements encourages the reagent beads to dissolve in the blood contained within the mixing chambers 134a-e as described above.

The analyzer console 140 can also include one or more sensors 448. The one or more sensors 448 can be used to detect the presence of blood in particular locations within the cartridge 120, such as blood detection locations 127a and 127b as described above (refer to FIG. 5). In some embodiments, the sensors 448 are optical sensors, such as IR (infrared) sensors. In some embodiments, the sensors 448 can be used to detect blood in other areas of the cartridge 120, such as, but not limited to, in the cups 136a-e (refer to FIGS. 8A-8H).

The sample handler assembly 400 of the analyzer console 140 also includes the viscoelastic measurement system 480. The viscoelastic measurement system 480 includes the baseplate 302 (e.g., refer to FIG. 10C), one or more thromboelastometry assemblies (e.g., thromboelastometry assembly 300b), and a linear actuator assembly. The one or more thromboelastometry assemblies can each be affixed to the baseplate 302. In some embodiments, the linear actuator assembly can be coupled to the baseplate 302 and to the cartridge receiver and clamp 410. Accordingly, actuation of the linear actuator assembly can translate the baseplate 302 and the cartridge receiver and clamp 410 towards each other or away from each other. A linear bearing assembly of the linear actuator can guide the baseplate 302 in a linear path, and stabilize the baseplate 302, as the baseplate 302 translates towards or away from the cartridge receiver and clamp 410.

In some embodiments, the linear actuator assembly causes the baseplate 302 to vertically raise or lower in relation to the cartridge receiver and clamp 410 using a motor (e.g., a DC motor or a stepper motor) that rotates a lead screw that has threads that are engaged with a drive nut. The drive nut is coupled to the baseplate 302. In some embodiments, end-of-travel detectors (e.g., proximity sensors, optical sensors, micro-switches, and the like) are included to detect when the baseplate 302 has been vertically translated to the desired end-of-travel positions.

The viscoelastic measurement system 480 includes one of more rotary thromboelastometry assemblies (e.g., rotary thromboelastometry assembly 300b of FIG. 10C) that include a shaft configured to couple with a pin (e.g., the shaft 310b configured to couple with the pin 138b). Because the thromboelastometry assemblies are mounted to the baseplate 302, the shafts are raised or lowered in conjunction with the raising or lowering of the baseplate 302. Accordingly, actuation of the linear actuator assembly causes the shafts to vertically raise or lower in relation to the cartridge receiver and clamp 410, and in relation to a cartridge 120 when a cartridge 120 is clamped within the cartridge receiver and clamp 410. Therefore, from the description herein it can be understood that actuation of the linear actuator assembly can engage and disengage the shafts from the pins of the cartridge 120 (e.g., refer to FIG. 10C that shows baseplate 302 being lowered to engage shaft 310b with pin 138b).

In addition to the aforementioned features of the analyzer console 140, in some embodiments the analyzer console 140 also includes one or more of the following features. The analyzer console 140 can include one or more barcode scanners 450 that, for example, can read a barcode at the barcode location 125 on the leading end of cartridge 120 (refer to FIG. 5). In some embodiments, the analyzer console 140 can include one or more devices to detect the presence of the cartridge 120 in a desired insertion location and/or orientation. For example, in some embodiments one or more micro switches can be used to detect when the cartridge 120 has been inserted in a desired location and orientation within the sample handler assembly 400. In some embodiments, the analyzer console 140 can include one or more auxiliary connections 460. The auxiliary connections 460 can include network and device connectors such as, but not limited to, one or more USB ports, Ethernet ports (e.g., RJ45), VGA connectors, Sub-D9 connectors (RS232), and the like. Such auxiliary connections 460 can be located on the rear of the main chassis 144, or at other convenient locations on the main chassis 144. For example, in some embodiments one or more USB ports may be located on or near the front of the main chassis 144.

The analyzer console 140 also includes a user interface 142 (e.g., with a touchscreen display in this embodiment). In the depicted embodiment, the user interface 142 is configured to receive user input and to display output information to the user. For example, the user can enter information to the analyzer console 140 by making selections of various soft-buttons that may be displayed on the user interface 142 at times during the beginning, middle, and end of the testing process. In some embodiments, other selections such as, but not limited to, soft keyboard entries can be provided via user interface 142. In some embodiments, data entry can be performed additionally or alternatively by voice entry. In some embodiments, the user interface may include other peripheral devices (e.g., a mouse, a keyboard, an additional display device, and the like) as part of the analyzer console 140. In some embodiments, a computer data network (e.g., intranet, internet, LAN, etc.) may be used to allow for remote devices to receive and/or input information from the system 100. For example, in some embodiments one or more remote displays can be utilized via auxiliary connections 460. In the depicted embodiment, the user interface 142 also includes an external barcode reader 146 (refer to FIG. 1A). Alternatively or additionally, the user interface 142 of the analyzer console 140 can be equipped with a reader configured to read near-field communication tags, RFID tags, or the like. The analyzer console 140 can also include one or more control systems 470 that can execute instructions embodied in a computer program. The control systems 470 can include, by way of example, both general and special purpose microprocessors, and any one or more processors of any kind of digital computer. In some embodiments, the control systems 470 includes one or more such processors, memory, storage devices, interfaces, and other types of electronic sub-systems and components. Such components may be mounted on a common motherboard or in other manners as appropriate. The control systems 470 can process instructions for execution within the analyzer console 140, including instructions stored in the memory or on the storage device. In some implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The storage devices are capable of providing mass storage for the control systems 470. In some implementations, the storage device may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described above in reference to FIGS. 8A-8H. The computer program product can also be tangibly embodied in a computer- or machine-readable medium, such as the memory, the storage device, or memory on the processor(s).

Figure 13:
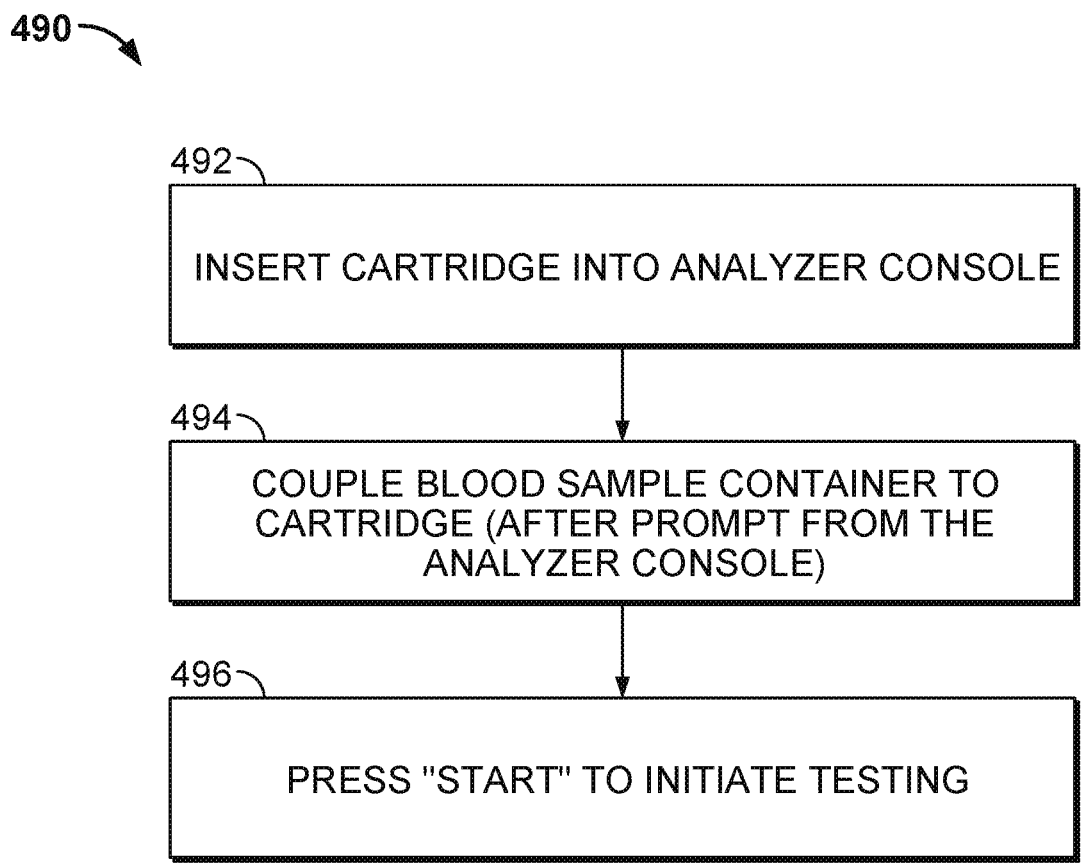
FIG. 13 is a flowchart of a method of using a thromboelastometry system, in accordance with some embodiments.

Referring to FIG. 13, in some implementations a user can interact with the thromboelastometry systems provided herein according to an example process 490. In step 492, the user can insert a cartridge into an analyzer console. In some examples, at least a portion of the cartridge remains exposed while other portions of the cartridge are concealed within the analyzer console. For example, this step is exemplified above in reference to FIG. 1A. In step 494, the user can couple a blood sample container to the cartridge after a prompt is received from the analyzer console. Step 494 can be performed while the cartridge remains inserted in the analyzer console as defined by step 492. At step 496, the user can press a "start" button (or equivalent) to initiate an automated transport of blood in the blood sample reservoir to the blood testing chambers of the cartridge such that the viscoelastic characteristics of the blood can be measured. In some examples, the analyzer console provides an indication that the testing is ready to be initiated, but that indication is not required as part of process 490.

Figure 14A:
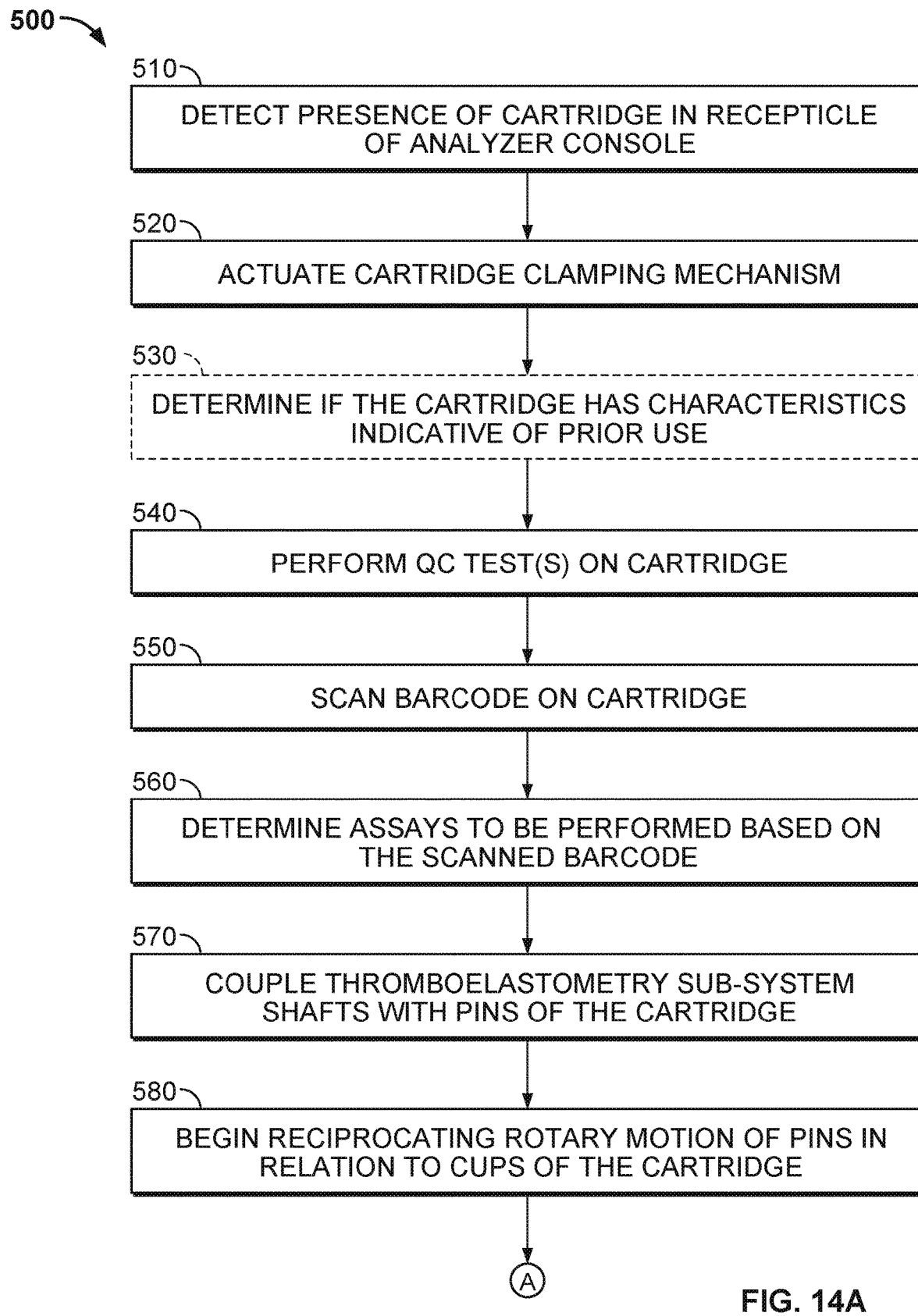
FIGS. 14A and 14B are a flowchart of a method for controlling a thromboelastometry system, in accordance with some embodiments.
Figure 14B:
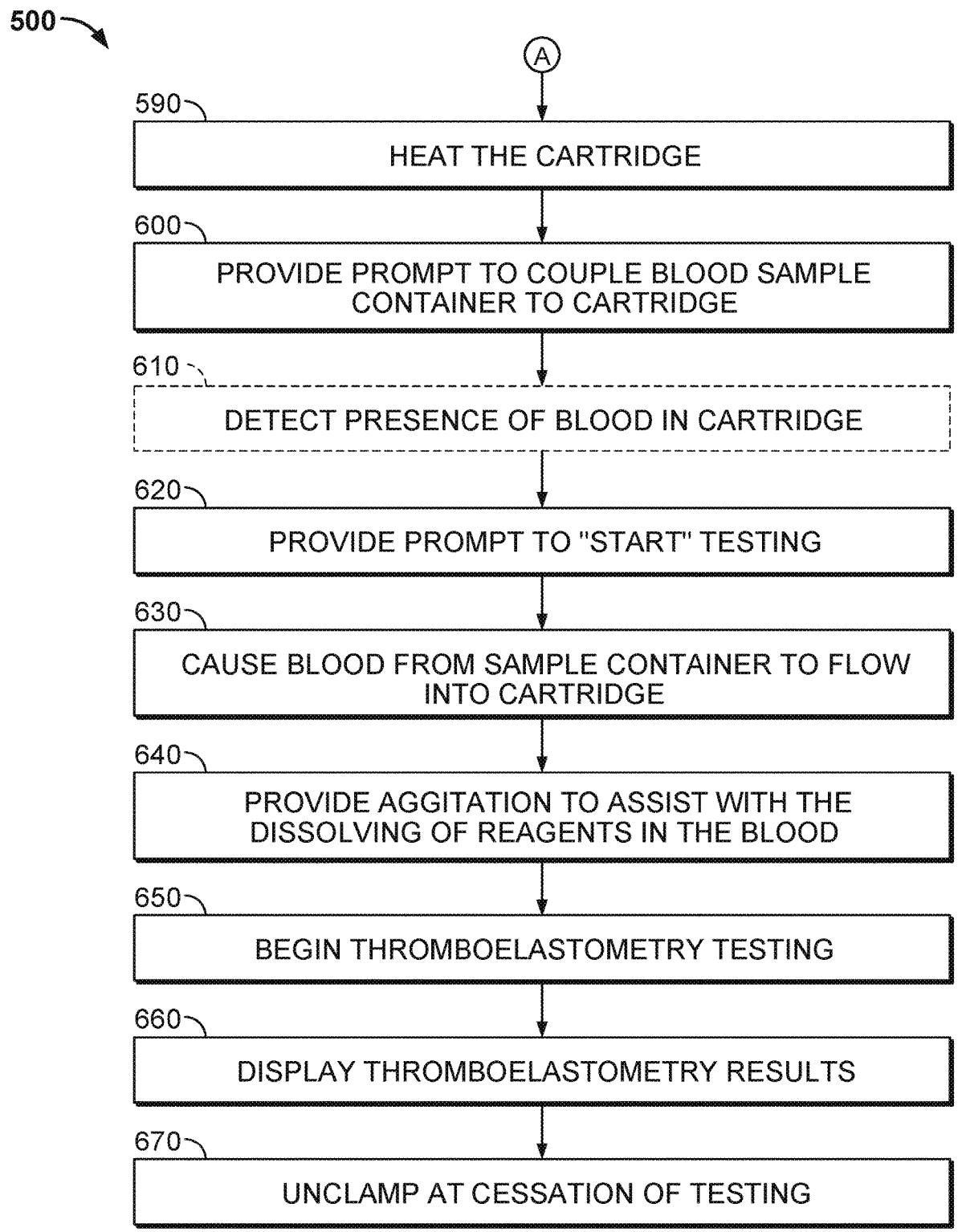

Referring to FIGS. 14A and 14B, in some implementations a thromboelastometry system can perform thromboelastometry according to an example process 500. The individual steps of the process 500 may not necessarily be performed in the order listed. Further, in some implementations some steps of the process 500 may be performed in parallel. The process 500 may be performed by the thromboelastometry systems described above, such as thromboelastometry system 100.

In step 510, the presence of a cartridge is detected in a receptacle of an analyzer console of the thromboelastometry system. For example, the detection may be performed by a micro switch, optical sensor, barcode scanner, and the like, or a combination thereof. Even though the cartridge is detected in the receptacle, at least a portion of the cartridge may be exterior to the analyzer console.

In step 520, the analyzer console actuates a clamping mechanism to clamp the cartridge at least partially in the analyzer console. For example, the cartridge receiver and clamp 410 as described above can be activated to clamp the cartridge.

In step 530, the analyzer console can optionally determine if the cartridge has characteristics that indicate the cartridge has been used previously. For example, the analyzer console may use optical sensors to inspect for the presence of blood in the cartridge. In some embodiments, if one or more characteristics that indicate the cartridge has been used previously are detected, the analyzer console may suspend further steps of process 500 and provide a pertinent message via the user interface.

In step 540, the analyzer console can perform one or more QC tests to test the integrity of the cartridge. For example, in some embodiments the cartridge can be tested for leaks such as by performing a pressure/vacuum decay test.

In step 550, the analyzer console scans the cartridge for a barcode. For example, the analyzer console may scan a leading end of the cartridge at which a 1D or 2D barcode may be present.

In step 560, the analyzer console determined the types of thromboelastometry assays to be performed based on the information attained from the scan of the barcode in step 550.

In step 570, the shafts of the thromboelastometry sub-system of the analyzer console are coupled with pins of the cartridge. The pins are located in cups of the cartridge. Accordingly, the coupling of the shafts of the thromboelastometry sub-system to the pins can configure the thromboelastometry system to be capable of performing thromboelastometry on a blood sample contained within the cups of the cartridge. For example, referring to FIG. 10C, the shaft 310b of the thromboelastometry assembly 300b can be lowered towards the cartridge so that the shafts 310b become friction-fit and releasably coupled with the pins 138b of the cartridge 120.

In step 580, the analyzer console can begin rotatory reciprocation of the pins in relation to the cups of the cartridge. For example, this step is exemplified above in reference to FIG. 10C.

In step 590, the analyzer console can heat the cartridge. In some implementations, the analyzer console may heat the cartridge to a predetermined temperature. In particular implementations, the analyzer console may maintain the cartridge at the predetermined temperature. For example, in some implementations the predetermined temperature may be about 35° C. to about 40° C., and preferably about 37° C.

In step 600, the analyzer console provides a prompt to couple a blood sample container to the cartridge. This prompt may be provided, for example upon the successful completion of one or more steps, or upon the successful verification of one or more conditions, or both. For example, this prompt may be provided upon the cartridge's successful attainment of the predetermined temperature as per step 590, among other things. The prompt may be provided via the user interface of the analyzer console. For example, the prompt may be a visual message displayed on a touchscreen monitor of the analyzer console. An audible prompt may be provided in some implementations.

In step 610, the analyzer console may optionally detect the presence of blood in the cartridge. Such detection may be performed, for example, using one or more IR sensors of the analyzer console. The detection of blood in the cartridge in this step can indicate that a blood sample container was successfully coupled to the cartridge.

In step 620, the analyzer console can provide a prompt to "start" testing. In some implementations, the prompt to "start" testing may be provided on the basis of the successful completion of one or more steps, or upon the successful verification of one or more conditions, or both. The prompt may be provided via the user interface of the analyzer console. For example, the prompt may be a visual message displayed on a touchscreen monitor of the analyzer console. In some embodiments, the touchscreen can receive a user input to start the testing.

In step 630, the analyzer console can cause blood to flow from the sample container into the cartridge. In some implementations, a vacuum source of the analyzer console is used to cause blood flow into the cartridge. In some implementations, an air pressure source of the analyzer console is used to cause blood flow into the cartridge. The analyzer console may also actuate various valves or vents to control the blood flow within the cartridge (e.g., refer to FIGS. 8A-8H).

In step 640, the analyzer console can induce agitation to assist with the dissolving of reagents in the blood contained within the cartridge. This step is exemplified above in regard to the horizontal reciprocation of the magnet shuttle with its one or more magnets that are magnetically coupled with mixing elements of the cartridge 120, causes movement of the mixing elements within the cartridge 120 to encourage the reagent beads to dissolve in the blood contained within the mixing chambers 134a-e.

In step 650, thromboelastometry testing is started. For example, the analyzer console can begin to analyze the data produced the thromboelastometry assemblies in regard to the reciprocating rotation of the shafts that are coupled with the pins 138a-e located in the cups 136a-e of the cartridge (refer to FIGS. 8A-8H). In some implementations, the analyzer console may begin to analyze the data produced by some of the thromboelastometry assemblies prior to beginning to analyze the data produced by others of the thromboelastometry assemblies. For example, as described above in reference to FIGS. 8A-8H, the analyzer console may begin to first analyze the data produced by the thromboelastometry assembly pertaining to cup 136e. Subsequently, the analyzer console may begin to analyze the data produced by the thromboelastometry assembly pertaining to cup 136d, and so on.

In step 660, the analyzer console displays the results of the thromboelastometry. Such results may be displayed concurrently with the performance of the testing and at the completion of the testing. The results can be displayed via the user interface of the analyzer console, such as on the touchscreen display. The results can be displayed using qualitative graphical representations and quantitative parameters.

In step 670, the analyzer console can unclamp the cartridge at the cessation of the testing. In some cases, such cessation may be initiated by a user input to the analyzer console to stop the testing, or by the completion of the test assays, or by the expiration of a time-based parameter. The unclamping may be performed, for example, by the horizontal translation of the moveable block sub-assembly. After the unclamping, the cartridge can be removed from the analyzer console.

A number of embodiments of the invention have been described. Nevertheless, it will be understood that various modifications may be made without departing from the spirit and scope of the invention. Accordingly, other embodiments are within the scope of the following claims.

What is claimed is:

1. A measuring system for measuring viscoelastic characteristics of a blood sample, comprising:
  an analyzer console to control at least one aspect of measuring the viscoelastic characteristics, the analyzer console defining an exterior port; and
  a disposable cartridge comprising a blood sample input accessible along an exterior of the cartridge and a plurality of blood processing and testing paths arranged in parallel, a blood processing and testing path among the plurality of blood processing and testing paths comprising:
    a measuring chamber for receiving a blood sample from the blood sample input;
    a mixing chamber for holding at least one reagent and for receiving the blood sample from the measuring chamber, the mixing chamber being in fluid communication with the measuring chamber; and
    a testing chamber for receiving a liquid that is based on a mixture of the test sample and the at least one reagent, the testing chamber being in fluid communication with the mixing chamber;

wherein the disposable cartridge comprises a vent port in fluid communication with the measuring chamber, the vent port being controllable to close when the measuring chamber receives the blood sample to inhibit flow of the blood sample from the measuring chamber into the mixing chamber; and wherein the exterior port of the analyzer console provides access to an internal space of the analyzer console having an internal interface element that is shaped complementarily to at least one complementary mating surface of the disposable cartridge such that the disposable cartridge is insertable into the internal space of the analyzer console to reach a stop that defines a fully inserted position in which the blood sample input of the cartridge remains external to the analyzer console while at least part of the plurality of blood processing and testing paths are positioned within the analyzer console.

2. The measuring system of claim 1, wherein the blood sample input of the disposable cartridge is configured to mate with a blood sample reservoir container, and wherein the all testing chambers are in fluid communication the blood sample input; and wherein the testing chamber comprises a blood input port in fluid communication with a corresponding output port of the mixing chamber.

3. The measuring system of claim 1, wherein the mixing chamber is configured to receive a predetermined volume of the blood sample from the measuring chamber.

4. The measuring system of claim 1, further comprising a pressure port, wherein the cartridge is configured such that, when negative pressure is applied to the pressure port, blood is transported to fill the measuring chamber.

5. The measuring system of claim 4, further comprising a first conduit between the blood sample input and the measuring chamber for transporting the blood sample.

6. The measuring system of claim 1, further comprising a valve between the mixing chamber and the testing chamber, the valve being controllable to open to allow the liquid to enter the testing chamber.

7. The measuring system of claim 1, wherein the analyzer console comprises one or more internal sensors to detect when the disposable cartridge is inserted to the fully inserted position in the internal space of the analyzer console.

8. The measuring system of claim 7, wherein the analyzer console comprises one or more blood detection sensors to detect that blood is absent from the disposable cartridge when the disposable cartridge is inserted to the fully inserted position in the internal space of the analyzer console.

9. The measuring system of claim 8, wherein, responsive to the one or more blood detection sensors detecting that blood is absent from the disposable cartridge, the analyzer console is configured to apply a vacuum or air pressure to the disposable cartridge for a leak test.

10. The measuring system of claim 7, wherein the analyzer console comprises a user interface display that, responsive to the disposable cartridge being inserted to the fully inserted position is configured to display a prompt indicating the disposable cartridge is ready to receive a blood sample.

11. The system of claim 1, wherein the disposable cartridge includes a machine-readable code, the analyzer console being configured to read the code for storage in internal memory.

12. The measuring system of claim 1, wherein the analyzer console comprises an internal cartridge clamping mechanism having a plurality of engagement elements configured to releasably retain the disposable cartridge in the fully inserted position.

13. The measuring system of claim 1, wherein the analyzer console comprises one or more heating elements positioned to heat at least part of the disposable cartridge to a targeted temperature.

14. A measuring system for measuring viscoelastic characteristics of a blood sample, comprising:
an analyzer console to control at least one aspect of measuring the viscoelastic characteristics, the analyzer console defining an exterior port; and
a disposable cartridge comprising a blood sample input accessible along an exterior of the cartridge and a plurality of blood processing and testing paths arranged in parallel, each of the plurality of blood processing and testing paths comprising:
 a measuring chamber for receiving a blood sample from the blood sample input;
 a mixing chamber for holding at least one reagent and for receiving the blood sample from the measuring chamber, the mixing chamber being in fluid communication with the measuring chamber; and
 a testing chamber for receiving a liquid that is based on a mixture of the test sample and the at least one reagent, the testing chamber being in fluid communication with the mixing chamber;
wherein the disposable cartridge comprises one or more devices that are controllable to allow flow of the blood sample from the measuring chamber into the mixing chamber; and
wherein the exterior port of the analyzer console provides access to an internal space of the analyzer console having an internal interface element that is shaped complementarily to at least one complementary mating surface of the disposable cartridge such that the disposable cartridge is insertable into the internal space of the analyzer console to reach a stop that defines a fully inserted position in which the blood sample input of the cartridge remains external to the analyzer console while at least part of the plurality of blood processing and testing paths are positioned within the analyzer console.

15. A measuring system for measuring viscoelastic characteristics of a blood sample, comprising:
an analyzer console to control at least one aspect of measuring the viscoelastic characteristics, the analyzer console defining an exterior port; and
a disposable cartridge comprising a blood sample input accessible from an exterior of the cartridge and a plurality of blood processing and testing paths arranged in parallel, wherein each blood processing and testing path is configured to receive a portion of the blood sample and comprises:
 a blood sample volume measurement chamber in fluid communication with the blood sample input, the blood sample volume measurement chamber having a selected internal volume that is sized to hold the portion of the blood sample;
 a mixing chamber in fluid communication with the blood sample volume measurement chamber to receive the portion of the blood sample from the blood volume measurement chamber, wherein the mixing chamber comprises reagent beads in solid form that dissolves when contacted with the portion of the blood sample from the blood sample volume measurement chamber to produce a mixture based on blood and reagent; and a viscoelastic blood testing chamber in fluid communication with the mixing chamber to receive the mixture; and wherein each blood sample volume measurement chamber in the plurality of blood processing and testing paths is part of a separate fluidic pathway connected to a respective mixing chamber and a respective viscoelastic blood testing chamber; and wherein the analyzer console is configured to releasably mate with the disposable cartridge when inserted into the exterior port such that the blood sample input of the cartridge remains external to the analyzer console while at least part of the plurality of blood processing and testing paths are positioned within the analyzer console.

16. The measuring system of claim 15, wherein each of the blood processing and testing paths comprises a conduit for transporting a mixture based on blood and reagent from the mixing chamber to the viscoelastic blood testing chamber.

17. The measuring system of claim 16, further comprising:

a valve associated with each conduit, the valve being configured to prevent flow of the mixture through the conduit when in a closed position and to allow the flow of the mixture through the third when in an open position.

18. The measuring system of claim 17, further comprising a pressure port to which pressure is applied to control transport of the mixture through the conduit from the mixing chamber to the viscoelastic blood testing chamber.

19. The measuring system of claim 15, wherein the disposable cartridge comprises pressure ports and vent ports that are selectively controllable to move fluid flows through fluid channels in the disposable cartridge following application of heat to at least part of the disposable cartridge.

20. The measuring system of claim 15, wherein the disposable cartridge further comprises vents and pressure ports; and wherein fluid flow into the blood sample volume measurement chamber is implemented by closing a vent and applying negative pressure to a vacuum port among the pressure ports.

21. The measuring system of claim 20, wherein fluid flow from the blood sample volume measurement chamber into the mixing chamber is implemented by changing a pressure at a pressure port among the pressure ports.

22. The measuring system of claim 20, wherein fluid flow from the mixing chamber into the viscoelastic blood testing chamber is implemented by changing a pressure at a pressure port among the pressure ports.

23. The measuring system of claim 14, wherein the one or more devices comprise one or more valves.

24. The measuring system of claim 14, wherein the disposable cartridge comprises pressure ports and vent ports that are selectively controllable to move fluid flows through fluid channels in the disposable cartridge following application of heat to at least part of the disposable cartridge.

25. The measuring system of claim 14, wherein the disposable cartridge further comprises vents and pressure ports; and wherein fluid flow into the measuring chamber is implemented by closing a vent and applying negative pressure to a vacuum port among the pressure ports.

26. The measuring system of claim 25, wherein fluid flow from the measuring chamber into the mixing chamber is implemented by changing a pressure at a pressure port among the pressure ports.

27. The measuring system of claim 25, wherein fluid flow from the mixing chamber into the testing chamber is implemented by changing a pressure at a pressure port among the pressure ports.

28. The measuring system of claim 1, wherein each measuring chamber in the plurality of blood processing and testing paths is part of a separate fluidic pathway connected to a respective mixing chamber and a respective testing chamber.

* * * * *